(12) United States Patent
Wong et al.

(10) Patent No.: US 8,816,050 B2
(45) Date of Patent: Aug. 26, 2014

(54) METHOD OF PREPARING GLYCOPEPTIDES

(75) Inventors: Chi-Huey Wong, La Jolla, CA (US);
Ashraf Brik, San Diego, CA (US);
Yu-Ying Yang, San Diego, CA (US);
Simon Ficht, San Diego, CA (US);
Richard Payne, San Diego, CA (US)

(73) Assignee: The Scripps Research Institute

( * ) Notice: Subject to any disclaimer, the term of this patent is extended or adjusted under 35 U.S.C. 154(b) by 1515 days.

(21) Appl. No.: 12/293,793

(22) PCT Filed: Mar. 22, 2007

(86) PCT No.: PCT/US2007/007142
§ 371 (c)(1),
(2), (4) Date: Nov. 18, 2010

(87) PCT Pub. No.: WO2007/111952
PCT Pub. Date: Oct. 4, 2007

(65) Prior Publication Data
US 2011/0060121 A1    Mar. 10, 2011

Related U.S. Application Data

(60) Provisional application No. 60/743,666, filed on Mar. 22, 2006.

(51) Int. Cl.
*C07K 1/00*     (2006.01)
*C07K 1/107*    (2006.01)

(52) U.S. Cl.
USPC ............................ 530/333; 530/395; 530/402

(58) Field of Classification Search
USPC ......................................... 530/333, 395, 402
See application file for complete search history.

(56) References Cited

PUBLICATIONS

Brik Ashraf, "Sugar-Assisted Glycopeptides Ligation." Journal of The American Chemical Society May 3, 2006 LNKD—PUBMED:16637616, vol. 128, No. 17, Apr. 8, 2006, pp. 5626-5627, XP009136142 ISSN: 0002-7863.

Brik Ashraf, "Sugar-Assisted Ligation of N-Linked Glycopeptides . . . " J. American Chemical Society, LNKD—DOI:10.1021/JA065601Q, vol. 128, No. 46, Nov. 1, 2006, pp. 15026-15033, XP009076648 ISSN Scheme : 0002-7863 1.

Liu Lei, "Advances in Glycoprotein Synthesis." Chemical Communications (Cambridge, England) Jan. 7, 2006 LNKD—PUBMED:16353085, No. 1, Jan. 7, 2006, pp. 21-33, XP009136147 ISSN: 1359-7345.

Brik Ashraf, "Sugar—Assisted Ligation for The Synthesis of Glycopeptides." Chemistry (Weinheim An Der Bergstrasse, Germany) 2007 LNKD—PUBMED:17508364, vol. 13, No. 20, Jul. 6, 2007, pp. 5670-5675, XP009136145 ISSN: 0947-6539.

*Primary Examiner* — David Lukton
(74) *Attorney, Agent, or Firm* — Wolf, Greenfield & Sacks, P.C.

(57) ABSTRACT

A method is provided for the synthesis of glycopeptides using a sugar assisted ligation strategy, wherein an N-terminal peptide portion in the form of a thioester is coopled with a C-terminal peptide portion bearing a carbohydrate moiety comprising a thiol group.

36 Claims, 8 Drawing Sheets

A

B

C

D

E

METHOD OF PREPARING GLYCOPEPTIDES

CLAIM OF PRIORITY TO PRIOR-FILED PATENT APPLICATION

This application is a national stage entry of PCT/US2007/007142, filed Mar. 22, 2007, which claims the benefit under 35 U.S.C. 119(e) of U.S. Provisional Application Ser. No. 60/743,666, filed Mar. 22, 2006, which is incorporated herein by reference in its entirety.

GOVERNMENT FUNDING STATEMENT

A portion of the work described herein was supported by grant number GM 44154, and GM 48870 from the National Institutes of Health. The United States Government has certain rights in this invention.

This application contains a sequence listing, submitted in both paper and a Computer Readable Form (CRF) on one CD-ROM. The CD-ROM contains one file called "37932_20101_ST25.txt" that is 18,335 bytes in size (measured in Windows XP) and created on Aug. 6, 2010, all of which are herein incorporated by reference.

FIELD OF THE INVENTION

The invention relates to a method of preparing peptides and glycopeptides through formation of a peptide bond via coupling of a peptide thioester and a glycopeptide bearing a thiol group on the sugar moiety.

BACKGROUND OF THE INVENTION

The chemical synthesis of peptides and proteins is a widely studied field, and methods have been developed for the syntheses of such compounds using sequential coupling reactions, particularly involving anchoring on solid phases such as polymers. However, sequential synthetic methods are not well suited for the preparation of larger peptides and proteins. For these, segment coupling methods have been developed whereby shorter peptides are joined in a controlled manner to produce larger molecules.

D. S. Kemp and co-workers developed a "thiol capture" strategy for the preparation of large peptides. ((a) Kemp, D. S. Biopolymers 1981, 20, 1793-1804. (b) Kemp D. S.; Carey, R. I. J. Org. Chem. 1993, 58, 2216-2222). This led to additional segment coupling approaches. Among them, the native chemical ligation methodology represents a useful tool for the chemical synthesis of proteins (Dawson, P. E.; Muir, T. W.; Clark-Lewis, I.; Kent, S. B. H. Science 1994, 266, 776-779). In this approach, an N-terminal cysteine residue is required for capturing a peptide thioester as a cysteine thioester of the peptide, which is followed by a spontaneous intramolecular S to N acyl transfer to form the amide (peptide) bond at the ligation junction.

To overcome the restriction imposed by the requirement for a cysteine residue at the ligation site, different strategies have been adopted to extend the repertoire of peptide conjugation techniques: ((a) Beligere, G. S.; Dawson, P. E. J. Am. Chem. Soc. 1999, 121, 6332-6333. (b) Yan, L. Z.; Dawson, P. E. J. Am. Chem. Soc. 2001, 123, 526-533. (c) Saxon, E.; Armstrong, J. I.; Bertozzi, C. R. Org. Lett. 2000, 2, 2141-2143. (d) Nilsson, B. L.; Kiessling, L. L.; Raines, R. T. Org. Lett. 2000, 2, 1939-1941). The use of removable thiol-based auxiliaries is an attractive approach to fulfill the same function as the thiol side chain of the cysteine. Peptides with $N^\alpha$-linked auxiliaries that can carry out a function analogous to that of cysteine, such as 1-phenyl-2-mercaptoethyl and 2-mercaptobenzyl groups, have been investigated and successfully applied to the synthesis of large peptides: ((a) Canne, L. E.; Bark, S. J.; Kent, S. B. H. J. Am. Chem. Soc. 1996, 118, 5891-5896. (c) Low, D. W.; Hill, M. G.; Carrasco, M. R.; Kent, S. B. H.; Botti, P. Proc. Natl. Acad. Sci. U.S.A. 2001, 98, 6554-6559. (d) Offer, J.; Boddy, C.; Dawson, P. E. J. Am. Chem. Soc. 2002, 124, 4642-4646. (e) Macmillan, D.; Anderson, D. W. Org. Len. 2004, 6, 4659-4662. (f) Lu, Y.-A.; Tam, J. P. Org. Lett. 2005, 7, 5003-5006).

The synthesis of glycopeptides from readily available materials represents an advantageous approach to the preparation of higher molecular weight peptides and glycopeptides for structural and functional studies. Therefore, there remains a need for improved methods for the preparation of larger peptides and proteins, glycopeptides, and other peptide derivatives.

SUMMARY OF THE INVENTION

An embodiment of the present invention concerns a method for forming a peptide bond between a peptide comprising a C-terminal carboxyl thioester and a sidechain-glycosyl peptide with a free N-terminal amino group wherein the sidechain-glycosyl includes a thiol group, comprising contacting the two reagents in an aqueous medium to form the coupled product via an intramolecular S to N shift of a acyl group from a thioester formed by a step of transthioesterification.

An embodiment of the present invention is directed to a method of preparing a compound of Formula (I):

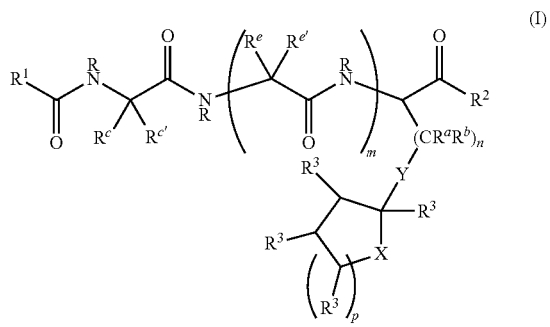

including any stereoisomers, tautomers, solvates, hydrates, or salts thereof;
wherein
m is 0 to about 10;
n is 1 to about 4;
$R^a$ and $R^b$ are each independently at each occurrence H or alkyl, or $R^a$ and $R^b$ together are oxo (=O);
p is 1, 2, or 3;
X is O or $CHR^3$;
each $R^3$ is independently at each occurrence hydrogen, $(C_1\text{-}C_3)$alkyl, hydroxy, or hydroxy$(C_1\text{-}C_3)$alkyl, wherein any hydroxy or hydroxyalkyl can be O-substituted with a monosaccharide, a disaccharide, an oligosaccharide, or a hydroxy-protecting group; provided that one $R^3$ comprises —OC(=O)(CH($R^s$))$_s$SH or —NHC(=O)(CH($R^s$))$_s$SH, wherein $R^s$ is independently at each occurrence hydrogen or $(C_1\text{-}C_6)$alkyl wherein any carbon atom of the $(C_1\text{-}C_6)$alkyl can be substituted with J, and s is 1 to about 6;
Y is $C(R^4R^5)$, O, NH or S;
$R^4$ and $R^5$ are each independently H, alkyl, or J;

the carbon atom bearing X and Y is in the R or the S configuration;

each NR is independently NH or N($C_1$-$C_3$)alkyl, or an NR, together with an $R^c$ or $R^e$ bonded to a carbon atom bearing the NR, can form a 4-7 membered ring, or each $R^c$, $R^{c_1}$, $R^e$, and $R^{e_1}$ is independently at each occurrence H, alkyl, aryl, heteroaryl, cycloalkyl, or heterocyclyl, or a sidechain of a naturally occurring amino acid which can be unblocked or blocked with a protecting group; or $R^c$ and $R^{c_1}$ or $R^e$ and $R^{e_1}$, or both, together with a carbon atom to which they are attached, form a cycloalkyl or heterocycloalkyl; wherein any alkyl, aryl, heteroaryl, cycloalkyl, or heterocyclyl is substituted with 0-3 J;

J is halogen, trifluoromethyl, cyano, nitro, ($C_{1-6}$)alkyl, ($C_{1-6}$)alkoxy, cycloalkyl, carboxy; acetamido, hydroxy, hydroxy($C_{1-6}$)alkyl, trifluoromethoxy, sulfamoyl, carbamoyl, sulfonamido, alkylsulfonyl, or arylsulfonyl; and $R^1$ and $R^2$ are each independently a peptide residue or a glycopeptide residue;

the method comprising:

contacting a compound of Formula (II):

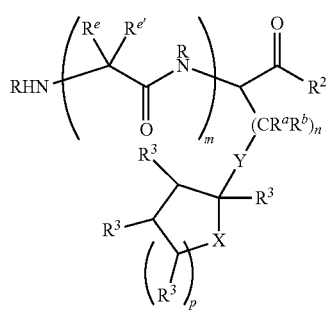

(II)

and a compound of Formula (III):

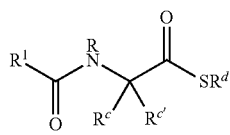

(III)

wherein $R^d$ is alkyl, aryl, aralkyl, carboxyalkyl or carboxamidoalkyl; to provide the compound of formula (I).

The method of the present invention offers significant advantages for the preparation of larger peptides and proteins and their derivatives. Large peptides and proteins, which can be difficult to prepare using either chemical or biological techniques, are of great importance for therapeutic and diagnostic use in medicine. Biological techniques for the synthesis of large peptides and proteins are generally limited to the essential amino acids, and specific derivatives are difficult to obtain through reaction of the final product. Thus, it is advantageous to have the versatility of a chemical approach which allows preparation of large peptides and proteins that contain non-natural amino acids or have non-amino acid groups attached to side chains, and so forth. Yet chemical synthesis using solid phase techniques is largely restricted to shorter peptides which, however, can include non-natural amino acids and other derivatives. Therefore, efficient techniques for assembling these shorter peptides into larger peptides are needed. The present invention provides such techniques, enabling the assembly of shorter peptides into larger ones in high yield and with good purity through an efficient segment ligation approach. Furthermore, the methods of the present invention enable the use of peptides largely without a requirement for having protecting groups on amino acid sidechains, which may assist the final product in achieving the proper folding and conformation, as the harsh deprotection conditions typically used in chemical synthesis of polypeptides may serve to denature the final product.

The method of the present invention has use in the synthesis of glycopeptides and glycoproteins without the need for a cysteine residue at the ligation site, which most of the present chemical synthetic methods rely on. It allows the selective ligation of two unprotected peptides in aqueous solution to furnish a larger glycopeptide. It further allows the synthesis of the backbone more complex glycopeptide structures, the sugar portion of which may be elaborated further through enzymatic methods to make a more complex glycopeptide of glycoprotein.

Alternatively, the modified sugar portion may be removed through either chemical or biological means to provide deglycosylated peptides and proteins.

The thiol group of the product can be removed to provide a glycosyl peptide or an acetamidoglycosyl peptide. Accordingly, an embodiment of the present invention is directed to the inventive method which further includes desulfurizing a compound of formula (I) wherein W is O or NH by contacting a compound of Formula (I) with a source of hydrogen in the presence of a catalyst. The thiol group is removed reductively to yield the acetamidoglycosyl peptide.

Another embodiment of the invention concerns the inventive method further including desulfurizing a compound of formula (I) wherein W is O, by contacting the compound with hydrazine or an alkaline solution. The thioacetyl ester group is cleaved by the alkaline conditions to yield an unprotected hydroxyl group at the position previously bearing the thioacetate, yielding the glycosyl peptide.

DETAILED DESCRIPTION OF THE INVENTION

Definitions

Figure 1:
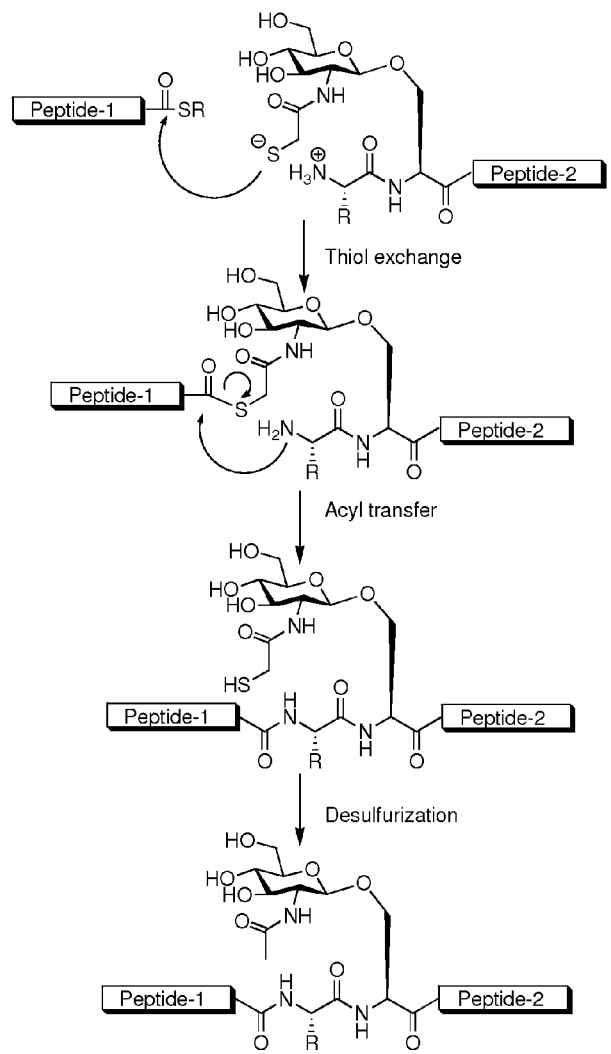
FIG. 1 shows a synthetic scheme for preparation of a glycopeptide according to the present invention.

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

References in the specification to "one embodiment", "an embodiment", "a preferred embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "amino acid," includes the ribosomal amino acids (e.g. Ala, Arg, Asn, Asp, Cys, Glu, Gln, Gly, His, Ile, Leu, Lys, Met, Phe, Pro, Ser, Thr, Trp, Tyr, and Val), with the proviso that each of these may be in the D or the L form, as well as naturally occurring but non-ribosomal amino acids (e.g. phosphoserine, phosphothreonine, phosphotyrosine, hydroxyproline, hydroxylysine, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). Further, the term encompasses α-amino acids that have not been found in nature, such as for example fluoro-substituted amino acids, as well as amino acids wherein the amino group is not in an α relationship with the carboxyl group, such as β-, γ-, and δ-amino acids.

The term "amino acid" also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide), as well as amino acids with sidechains such as carboxyl, carboxamide, amino, guanido, thio, hydroxyl, and other groups bearing protecting groups. Additional suitable protecting groups of all these types are known to those skilled in the art (See for example, Greene, T. W.; Wutz, P. G. M. *Protecting Groups In Organic Synthesis*, 2$^{nd}$ edition, John Wiley & Sons, Inc., New York (1991) and references cited therein).

The term "amino acid sidechain" as used herein refers to a monovalent radical bonded to a carbon atom of an amino acid, that is other than the carboxylic acid (COOH) group of the amino acid. In specific embodiments of the invention, the term "amino acid sidechain" can refer to the group R, as exemplified in the following structure of a ribosomal α-amino acid:

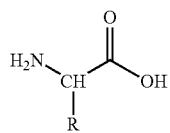

wherein R is methyl (Ala); R is 3-guanidopropyl (Arg); R is carboxamidomethyl (Asn); R is carboxymethyl (Asp); R is thiolmethyl (Cys); R is carboxyethyl (Glu); R is carboxamidoethyl (Gln); R is hydrogen (Gly); R is (4-imidazolyl)methyl (His); R is isobutyl (Ile); R is sec-butyl (Leu); R is 4-aminobutyl (Lys); R is 2-(methylthio)ethyl (Met); R is benzyl (Phe); R is hydroxymethyl (Ser); R is 1-hydroxyethyl (Thr,); R is 3-indolylmethyl (Trp); R is p-hydroxybenzyl (Tyr); and R is isopropyl (Val). It is understood that additional carbon atoms may exist between the carboxyl group and the amino group of an amino acid, and the R group may reside on any of those carbon atoms. In an α-amino acid, the structure is as shown above, but the "amino acid sidechain" may be disposed on a carbon atom other than the carboxyl carbon of a β-, γ-, or δ-amino acid.

The term "peptide" describes a sequence of 2 or more amino acids (e.g. as defined hereinabove) wherein the amino acids are sequentially joined together by amide (peptide) bonds. The sequence may be linear or cyclic. When the sequence is cyclic, the peptide may further comprise other bond types connecting the amino acids, such as an ester bond (a depsipeptide) or a disulfide bond. For example, a cyclic peptide can be prepared or may result from the formation of a disulfide bridge between two cysteine residues in a sequence. Peptide sequences specifically recited herein are written with the amino or N-terminus on the left and the carboxy or C-terminus on the right.

A "peptide residue" refers to a sequence of amino acids, that is, amino acids connected by amide bonds, wherein the N-terminus and the C-terminus are not necessarily in free form but may be further linked to additional amino acids or to other radicals. Thus a single peptide may include a large set of possible peptide residues as defined herein.

The term "carbohydrate" as used herein includes the class of compounds commonly known as sugars, in addition to compounds that are chemically related to sugars. The term thus includes simple monosaccharide sugars, disaccharide sugars as well as polymeric substances. The term encompasses a group of compounds including sugars, starches, gums, cellulose and hemicelluloses. The term further encompasses sugar derivatives such as amino-sugars, for example, 2-amino-2-deoxyglucose, as well as their oligomers and polymers; sulfated sugars; and sugars with hydroxyl, amino, and other groups bearing protecting groups.

A carbohydrate as defined herein comprises sugars or sugar derivatives with beta (β) or alpha (α) anomeric stereochemistry; moreover, the sugars can have (R) or (S) relative configurations, can exist as the (+) or (−) isomer, and can exist in the D or L configuration. The terms "anomer" and "anomeric" refer to the stereochemical configuration at the acetal, hemiacetal, or ketal carbon atom, as is well known in the art.

The term "glycopeptide" refers to a peptide that is covalently linked to a carbohydrate. Typically, the carbohydrate is linked via an amino acid sidechain that comprises a hydroxyl, amino, amido, or carboxyl group. The carbohydrate may be linked through an anomeric hydroxyl group, or via another hydroxyl group or through an amino group or other functional group on the carbohydrate moiety.

"Alkyl" refers to a $C_1$ to about a $C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), and so forth. The alkyl can be a monovalent radical, capable of bonding to a single radical as described and exemplified above, or it can be a divalent radical capable of bonding to two distinct monovalent radicals or to a single divalent radical.

The alkyl can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl or hydroxy. The alkyl can optionally be interrupted with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (-OC(=O)—), imine (C=NH), sulfinyl (SO) or sulfonyl (SO$_2$). Additionally, the alkyl can optionally be at least partially unsaturated, thereby providing an alkenyl.

The term "aryl" refers to an unsaturated aromatic carbocyclic group of from 6 to about 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

The aryl can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl or hydroxy.

The term "cycloalkyl" refers to cyclic alkyl groups of from 3 to 20 carbon atoms having a single cyclic ring or multiple condensed rings; e.g. bicyclo, tricyclo, and higher polycyclic entities. Such cycloalkyl groups include, by way of example, single ring structures such as cyclopropyl, cyclobutyl, cyclopentyl, cyclooctyl, and the like, or multiple ring structures such as adamantanyl, bicyclo structures such as pinanes, and the like.

The cycloalkyl can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl or hydroxy.

The cycloalkyl can optionally be at least partially unsaturated, thereby providing a cycloalkenyl.

The term "heterocycloalkyl" refers to a cycloalkyl group wherein one or more of the ring carbon atoms is replaced by a heteroatom, such as oxygen, nitrogen, phosphorus, or sulfur. The term encompasses structures wherein two or more carbon atoms are replaced, each by a different type of heteroatom.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted. Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, β-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-19], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl or hydroxy.

A "radical" as used herein refers to a molecular structural unit of any atomic composition. A "monovalent radical" is a molecular structural unit with a single unfilled valence that may form a single covalent bond to a single molecular entity. A "divalent radical" is a structural unit with two unfilled valences that may form a single covalent bond to each of two molecular entities, or a double covalent bond to a single molecular entity. A radical may be a single atom or a highly complex multiatomic structure.

The term "amino" refers to —NH$_2$, and the term "alkylamino" refers to —NR$_2$, wherein at least one R is alkyl and the second R is alkyl or hydrogen. The term "acylamino" refers to RC(=O)N, wherein R is alkyl or aryl.

The terms "carboxy" or "carboxyl" refer to a monovalent radical —CO$_2$H or —CON, wherein M is a cation and the —CO$_2$ portion bears a negative charge; both groups having a single additional valance to be filled by formation of a single bond to a substituent. A C(═O) radical is termed a "carbonyl" and is a divalent radical, having two valances that are filled by single bonding to two separate substituents or double bonding to a single substituent.

The term "thiol" or "mercapto" refers to the monovalent radical —SH. With a single unfilled valance, it may be bonded to a single substituent.

The terms "hydroxyl" or "hydroxy" as used herein refer to the monovalent —OH radical, typically bonded to a carbon atom, although the term encompasses an —OH group bonded to a heteroatom. A "hydroxyl protecting group" refers to any of the groups that may replace the hydrogen atom of the —OH group such as to render the group less reactive or unreactive under certain conditions. See, for example, Greene, T. W.; Wutz, P. G. M. *Protecting Groups In Organic Synthesis*, 2$^{nd}$ edition, John Wiley & Sons, Inc., New York (1991) and references cited therein. A "hydroxyl protecting group" as used herein thus encompasses esters such as acetates and benzoates, carbonates such as methyl carbonates, urethanes such as dimethylaminocarbamates, acetals such as tetrahydropyranyl ethers and methoxymethyl ethers, sulfonate esters such as p-toluenesulfonyl esters, and silyl ethers such as tert-butyldiphenylsilyl ethers.

The term "oxo" or "an oxo group" as used herein refers to a divalent radical of the formula ═O, wherein a single oxygen atom is bonded via a covalent double bond to another atom. When an oxo group is bonded to a carbon atom, that group is a carbonyl radical.

The carbohydrate-assisted glycopeptide ligation ("sugar-assisted ligation (SAL)") according to the present invention comprises the use of a thiol-bearing carbohydrate moiety covalently bonded to an amino acid sidechain of a peptide to direct the coupling of that peptide with another peptide bearing a C-terminal thioester group. As described herein, a sugar moiety, covalently linked to an amino acid residue, includes a thiol-bearing moiety such as a mercaptoacetate or mercaptoacetamide, which forms a thioester with the peptide thioester reagent, the internal thioester subsequently undergoing intramolecular S to N acyl migration. In a preferred embodiment, the coupling reaction is carried out in aqueous solution, and may be carried out largely without the use of amino acid sidechain protecting groups. Carbohydrate hydroxyl groups may also be present in unprotected form. A "native chemical ligation (NCL)" is a ligation that can be carried out between a peptide thioester and a peptide with the N-terminal amino acid being cysteine, wherein a thioester bond is first formed with the cysteine, which is followed by intramolecular S to N acyl migration.

The high coupling yield that is obtained due to the directing effect of the carbohydrate thiol group is an outstanding feature of the present invention. This simplifies the preparation of high molecular weight peptides when a fragment ligation strategy is employed relative to previously existing techniques.

Obviously, numerous modifications and variations of the present invention are possible in light of the above teachings. It is therefore to be understood that within the scope of the appended claims, the invention may be practiced otherwise than as specifically described herein.

Specific ranges, values, and embodiments provided below are for illustration purposes only and do not otherwise limit the scope of the invention, as defined by the claims.

Specific Ranges, Values, and Embodiments

An embodiment of the present invention concerns a method of preparing a compound of Formula (I):

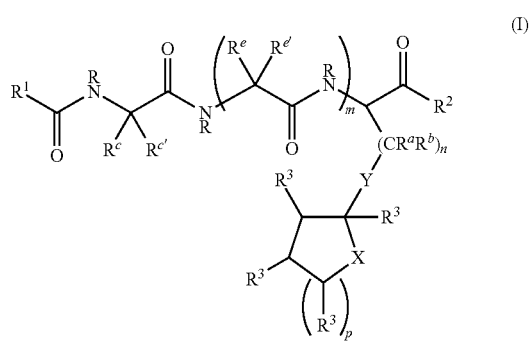

including any stereoisomers, tautomers, solvates, hydrates, or salts thereof;

wherein m is 0 to about 10;

n is 1 to about 4;

$R^a$ and $R^b$ are each independently at each occurrence H or alkyl, $R^a$ and $R^b$ together are oxo (═O);

p is 1, 2, or 3;

X is O or $CHR^3$;

each $R^3$ is independently at each occurrence hydrogen, $(C_1-C_3)$alkyl, hydroxy, or hydroxy$(C_1-C_3)$alkyl, wherein any hydroxy or hydroxyalkyl can be O-substituted with a monosaccharide, a disaccharide, an oligosaccharide, or a hydroxy-protecting group; provided that one $R^3$ comprises —OC(═O)(CH($R^s$))$_s$SH or —NHC(═O)(CH($R^s$))$_s$SH, wherein $R^s$ is independently at each occurrence hydrogen or $(C_1-C_6)$alkyl wherein any carbon atom of the $(C_1-C_6)$alkyl can be substituted with J, and s is 1 to about 6;

Y is $C(R^4R^5)$, O, NH or S;

$R^4$ and $R^5$ are each independently H, alkyl, or J;

the carbon atom bearing X and Y is in the R or the S configuration;

each NR is independently NH or N$(C_1-C_3)$alkyl, or an NR, together with an $R^c$ or $R^e$ bonded to a carbon atom bearing the NR, can form a 4-7 membered ring, or each $R^c$, $R^{c'}$, $R^e$, and $R^{e'}$ is independently at each occurrence H, alkyl, aryl, heteroaryl, cycloalkyl, or heterocyclyl, or a sidechain of a naturally occurring amino acid which can be unblocked or blocked with a protecting group; or $R^c$ and $R^{c'}$ or $R^e$ and $R^{e'}$, or both, together with a carbon atom to which they are attached, form a cycloalkyl or heterocycloalkyl; wherein any alkyl, aryl, heteroaryl, cycloalkyl, or heterocyclyl is substituted with 0-3 J;

J is halogen, trifluoromethyl, cyano, nitro, $(C_{1-6})$alkyl, $(C_{1-6})$alkoxy, cycloalkyl, carboxy; acetamido, hydroxy, hydroxy$(C_{1-6})$alkyl, trifluoromethoxy, sulfamoyl, carbamoyl, sulfonamido, alkylsulfonyl, or arylsulfonyl; and $R^1$ and $R^2$ are each independently a peptide residue or a glycopeptide residue;

the method comprising:
contacting a compound of Formula (II):

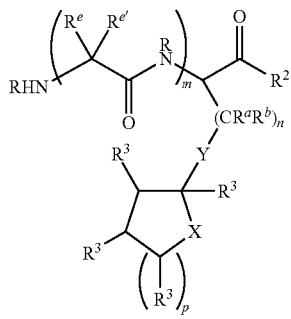

and a compound of Formula (III):

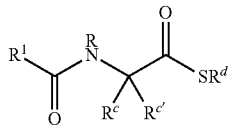

wherein $R^d$ is alkyl, aryl, aralkyl, carboxyalkyl or carboxamidoalkyl;
to provide the compound of formula (I).
For the compound of formula (I):
A specific value for m is 1, 2, 3, 4, 5, or 6.
A specific value for n is 1, 2, or 3.
A specific value for p is 1 or 2.
A specific value for $R^a$ is H or methyl.
A specific value for $R^b$ is H.
A specific value for each $R^3$ is OH.
A specific value for W is NH or O.
A specific value for X is O.
A specific value for Y is O.
A specific value for $R^c$ is an amino acid sidechain. Another specific value for $R^c$ is H, methyl or (4-imidazolyl)-methyl.
A specific value for $R^e$ is an amino acid sidechain. Another specific value is H.
A specific value for each R is H.
Another specific value for R and $R^c$ taken together is a pyrrolidine ring.
A specific value for $R^1$ is N-acetyl-Leu-Tyr-Arg-Ala. (SEQ ID NO:1 corresponds to unmodified amino acids).
A specific value for $R^2$ is phenylalaninamide. Another specific value is P—Y-G-S—$NH_2$. (SEQ ID NO:2 corresponds to unmodified amino acids).
For the compound of formula (II):
A specific value for m is 1, 2, 3, 4, 5, or 6.
A specific value for n is 1, 2, or 3.
A specific value for p is 1 or 2.
A specific value for $R^a$ is H or methyl.
A specific value for $R^b$ is H.
A specific value for each $R^3$ is OH.
A specific value for W is NH or O.
A specific value for X is O.
A specific value for Y is O.
A specific value for $R^c$ is an amino acid sidechain. Another specific value for $R^c$ is H, methyl or (4-imidazolyl)-methyl.
A specific value for $R^e$ is an amino acid sidechain. Another specific value is H.
A specific value for each R is H.
Another specific value for R and $R^c$ taken together is a pyrrolidine ring.
A specific value for $R^1$ is N-acetyl-Leu-Tyr-Arg-Ala. (SEQ ID NO:1 corresponds to unmodified amino acids).
A specific value for $R^2$ is phenylalaninamide. Another specific value is P—Y-G-S—$NH_2$. (SEQ ID NO:2 corresponds to unmodified amino acids).
For the compound of formula (III):
A specific value for $R^1$ is N-acetyl-Leu-Tyr-Arg-Ala.
A specific value for $R^d$ is phenyl or —$CH_2CH_2CONH_2$.

DETAILED DESCRIPTION

Referring to FIG. 1, a synthetic scheme of an embodiment according to the present invention is shown. The peptide referred to as "Peptide 1" that will form the N-terminal segment of the product is prepared with a C-terminal carboxy thioester, which serves to activate the segment for amide (peptide) bond formation. Peptide 1 may optionally be protected at its N-terminus, for example with an N-acetyl group, or may have a free amino group. Otherwise, there is no requirement for blocking or protection of sidechain moieties except when a cysteine residue is present in the sequence. Sidechains comprising free amino groups as in lysine, free hydroxyl groups as in tyrosine, serine and threonine, free guanido groups as in arginine, free carboxyl groups as in aspartate or glutamate, and free carboxamido groups as in asparagine and glutamine may be present during the coupling reaction in unprotected form. Cysteine residues, however, can be blocked during the coupling reaction, for instance as acetamidomethyl or tert-butyl derivatives.

To prepare the Peptide 1 thioester for use as a reactant in the method of the present invention, the C-terminal carboxyl group may be obtained in thioester form using any suitable method. Preferably, the C-terminal thioester group is provided using known solid phase peptide synthesis procedures, wherein the anchoring polymer is derivatized with a group that will yield the desired thioester upon final removal of the assembled peptide from the polymer. The group that will eventually yield the thioester is coupled to the polymer prior to solid phase synthesis of Peptide 1. For example, a β-mercaptopropionyl group may be preloaded onto a polymer, such as a p-methylbenzhydrylamine—(MBHA) substituted polystyrene, by attaching a 3-(tritylthio)propionate residue to the polymer followed by removal of the S-trityl group with acid. An MBHA resin preloaded with a 3-(tritylthio)propionyl residue is commercially available, for example as Novabiochem® catalog number 01-64-0449. The rest of the peptide is then synthesized, then cleaved from the resin under conditions that also result in deblocking of the sidechains and of the α-amino group if desired, providing Peptide 1 with the C-terminal carboxyl group as a β-mercaptopropionamide thioester.

The peptide segment shown as "Peptide 2" in FIG. 1 will form the C-terminal portion of the coupled glycopeptide. Peptide 2 comprises an amino acid bearing a sidechain to which a carbohydrate moiety is covalently bonded. Peptide 2 comprises an α-amino group which will be coupled with the carboxyl thioester of Peptide 1 by the method of the invention. In a preferred embodiment, the carbohydrate moiety comprises a 2-amino-2-deoxyglucose group covalently bonded to Peptide 2, wherein the 2-amino group of the sugar is covalently bonded to a mercaptoacetate group. Preferably, the carbohydrate moiety with the attached thiol group is bonded to the peptide via a glycosidic linkage with the hydroxyl group of a serine sidechain. Alternatively, the carbohydrate moiety may be bonded to Peptide 2 via the hydroxyl group of a threonine sidechain, or via a sidechain comprising an amino group, a carboxyl group, or a carboxamido group, for example of an asparagine residue, without departing from the principles of the invention. Similarly, the carbohydrate moiety may be provided with the thiol group in other ways than through formation of the mercaptoacetamide of 2-amino-2-deoxyglucose. For example, the thiol group can be bonded to the carbohydrate moiety as a mercaptoacetate ester of a sugar hydroxyl group.

It is understood that the linkage between the carbohydrate moiety and the amino acid sidechain may comprise a linkage of the β-anomeric configuration of the carbohydrate moiety. However, the linkage between the amino acid sidechain and the carbohydrate moiety may also be of the α-anomeric configuration.

As is illustrated in FIG. 1, it is believed that the mechanism by which the coupling to form the new peptide bond occurs is through an intermediate wherein the carboxyl thioester of Peptide 1 is exchanged to form a new carboxyl thioester of Peptide 1 with the thiol group borne by the carbohydrate moiety of Peptide 2. The β-thiopropionamide group of Peptide 1 is displaced by the carbohydrate thiol group to provide a coupled intermediate thioester, shown as the second molecular structure in FIG. 1. Evidence for the existence of such an intermediate thioester is provided in Example 28, at least for the case where the C-terminal residue of Peptide 1 is valine. As is shown in Example 23, the half life for the coupling reaction is substantially greater in the case where the C-terminal amino acid residue of Peptide 1 is valine, as compared to when the C-terminal amino acid residue is glycine, alanine or histidine. In Example 28, mass spectral analysis indicates the presence of a thioester bond between Peptide 1 and the thiol group of the carbohydrate moiety in the valine case, whereas when the C-terminal amino acid is glycine, alanine or histidine, the observed product comprises the coupled peptide product wherein an amide bond has been formed. Thus, it is believed that an intermediate of this type may be present in the other coupling reactions, wherein the intermediate thioester spontaneously is transformed under the reaction conditions to the coupled product, shown as the third structure in FIG. 1. However, the mechanism of the reaction may be different than as theorized herein without departing from the principles of the invention.

The final coupling product, shown as the third structure in FIG. 1, illustrates the newly-formed amide bond between Peptide 1 and Peptide 2 that results from the coupling reaction of the present invention. The coupling reaction is preferably is carried out in weakly alkaline aqueous solution; a pH of about 8.5 is preferred, although other pHs may be used without departing from the principles of the invention. Preferably a concentration of about 0.2 M phosphate buffer is used to buffer the aqueous solution at around pH 8.5. Additional reagents are preferably added to the aqueous solution; for example guanidine at a concentration of about 6M may be added. Also, to minimize oxidation of the thiol groups in the reactant, a thiol reagent is preferably added, such as thiophenol, benzyl mercaptan, or 2-mercaptoethanesulfonate. Preferably the coupling reaction is carried out in the absence of oxygen under an inert atmosphere.

The coupling reaction is preferably carried out at about 37° C., at which temperature it typically has a half-life ranging from a few hours to about 10 hours. The half life of the reaction is dependent upon the identity of the C-terminal amino acid residue of Peptide 1. As is shown in Example 23, an amino acid with a sterically more bulky sidechain in that position slows the rate and thus lengthens the half-life of the coupling reaction.

The progress of the coupling reaction is readily monitored using high pressure liquid chromatography (HPLC). Examples are provided in Examples 23 and 25. The coupled product is also readily purified by using preparative scale HPLC. In Example 23, the reaction was terminated after about 12 hours at 37° C., and a 76% yield of purified coupled glycopeptide was isolated by preparative HPLC. The purity of the product obtained after HPLC was in excess of 90%.

Once the coupled glycopeptide product is obtained, preferably in purified form, it may be desulfurized, although a coupled glycopeptide product still comprising a thiol group may be used or transformed in other ways without departing from the principles of the invention. In order to desulfurize the glycopeptide product as is illustrated in the final conversion shown in FIG. 1, the product is exposed to reductive conditions such that the sulfur atom of the thiol group is replaced by a hydrogen atom. The preferred mercaptoacetyl group is reductively converted to an acetyl group, as is shown in the fourth structure of FIG. 1. A preferred method of carrying out the desulfurization reaction is exposure of the thiol-containing glycopeptide to a source of hydrogen in the presence of a metal catalyst. A preferred source of hydrogen is hydrogen gas. Another preferred source of hydrogen is a borohydride salt such as sodium borohydride. The catalyst may be any suitable catalyst used for hydrogenation reactions, such as noble metal catalysts like palladium, platinum, or rhodium or nickel catalysts such as Raney nickel.

The desulfurization reaction may be carried out in any suitable solvent, but preferably an aqueous medium is used. Preferably, the aqueous medium is slightly acidic at a pH of about 5.8, being buffered at about that pH with about 0.1 M phosphate buffer. When a noble metal catalyst such as palladium is used, the reaction mixture is kept under hydrogen gas at about atmospheric pressure until the reaction is substantially complete, typically within a few hours. Again, the reaction is readily monitored using HPLC. Examples 24 and 25 provide details of a typical desulfurization reaction. The desulfurized product may be purified by preparative HPLC. Alternatively the desulfurization reaction can be carried out on a mercaptoacetyl ester of the sugar group by hydrazinolysis or alkaline saponification, as discussed below.

Examples 29-37 provide additional experimental details for another synthesis using a 2-aminoglycose bearing a mercaptoacetate group on the aminosugar nitrogen atom.

Example 38-40 provide experimental details of syntheses using a 3-mercaptoacetate ester of glucose as the thiol-containing group, as shown in the following scheme:

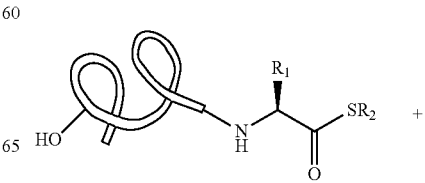

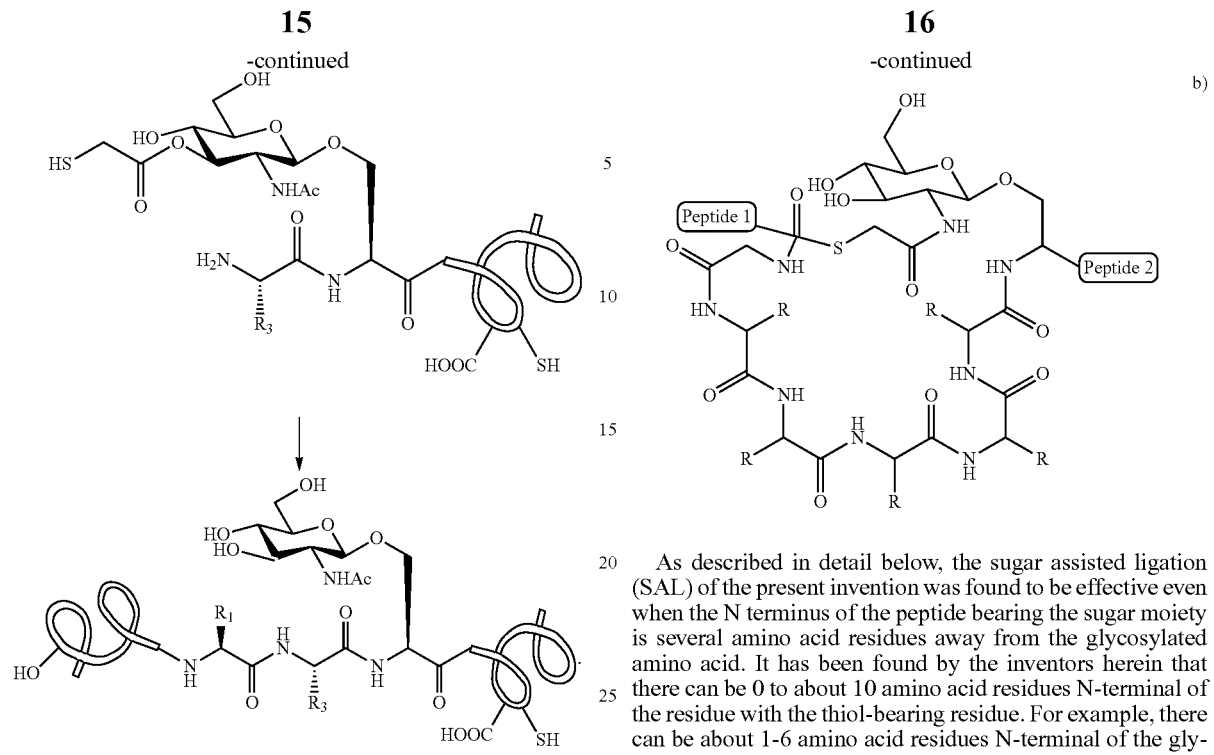

It has been found by the inventors herein that the thiol-containing group that forms the thioester intermediate that undergoes intramolecular S to N rearrangement to give the final product can be disposed by means of a different type of covalent bond, such that it can readily be removed without using hydrogenation. When the mercaptoacetamide of 2-aminoglucose provides the thio-containing group that catalyzes the ligation reaction, the thiol group is removed via hydrogenation, such as with palladium catalyst. However, in the series exemplified by Example 38-40, a mercaptoacetyl ester of a hydroxyl group, such as the 3-OH of a glucose moiety, can be used to bring about the ligation reaction. Due to the susceptibility of such ester groups to alkaline saponification, after the ligation reaction the thiol group can be removed by hydrolysis rather than by hydrogenation. Cleavage of the ester bond releases a free glucose hydroxyl group.

Examples 41-43 provide experimental details of syntheses wherein there are greater numbers of amino acid residues N-terminal of the residue bearing the sugar moiety. The below scheme shows proposed transition states of a) SAL (14 membered ring) and b) SAL with six amino acid extensions N-terminal to the glycosylated residue (29 membered ring), R=amino acid side chain functionality.

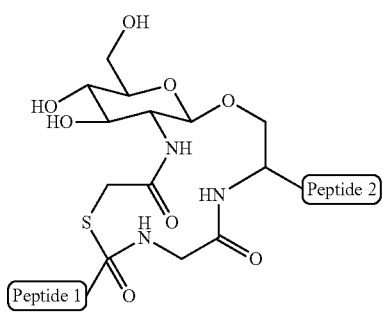

As described in detail below, the sugar assisted ligation (SAL) of the present invention was found to be effective even when the N terminus of the peptide bearing the sugar moiety is several amino acid residues away from the glycosylated amino acid. It has been found by the inventors herein that there can be 0 to about 10 amino acid residues N-terminal of the residue with the thiol-bearing residue. For example, there can be about 1-6 amino acid residues N-terminal of the glycosylated residue, and coupling yields remain relatively high. It is believed that formation of large, cyclic transition states such as are illustrated above can account for this effect. Example 44 is an example of a coupling reaction wherein the sugar is attached to the amide nitrogen atom of an asparagine sidechain.

Any patent, patent document, or reference disclosed herein is incorporated into reference into this invention and forms part of this invention. The present invention can be illustrated by the following non-limiting examples.

EXAMPLES

Abbreviations

Boc tert-butoxycarbonyl
DCM dichloromethane
DIEA di-isopropylethylamine
DMF N,N-dimethylformamide
EA ethyl acetate
ESI-TOF electrospray ionization—time of flight
Fmoc 9-fluorenylmethoxycarbonyl
HBTU O-(benzotriazol-1-yl)-1,1,3,3,-tetramethyluronium $PF_6$
Hex hexanes
HOBt N-hydroxybenzotriazole
HRMS high resolution mass spectrometry
MALDI-TOF mass-assisted laser desorption ionization-time of flight
MBHA methylbenzhydrylamine
MS molecular sieves
NMA N-methylaniline
NMM N-methylmorpholine
PMB p-methoxybenzyl
PyBOP 1-(7-azabenztriazolyloxy)tris(dimethylamino)phosphonium $PF_6$
rt room temperature
Tf trifluoromethanesulfonate
TFA trifluoroacetic acid
THF tetrahydrofuran
TMS trimethylsilyl
Trt trityl

Example 1

Synthetic Scheme for Glycopeptide 2

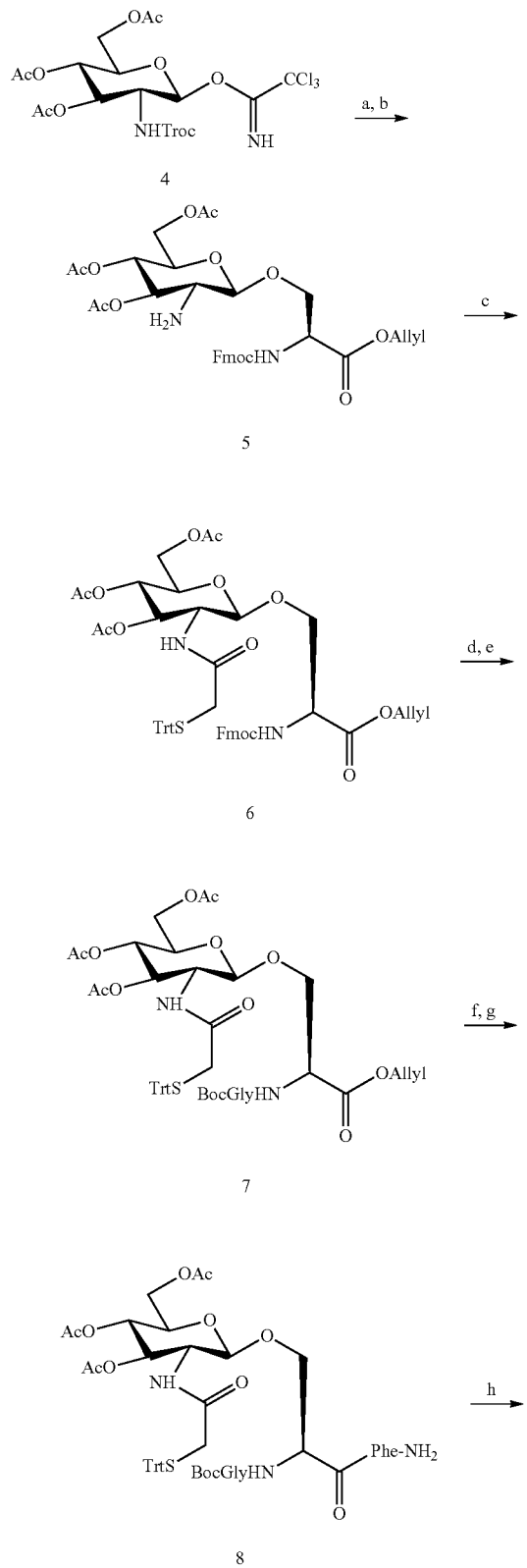

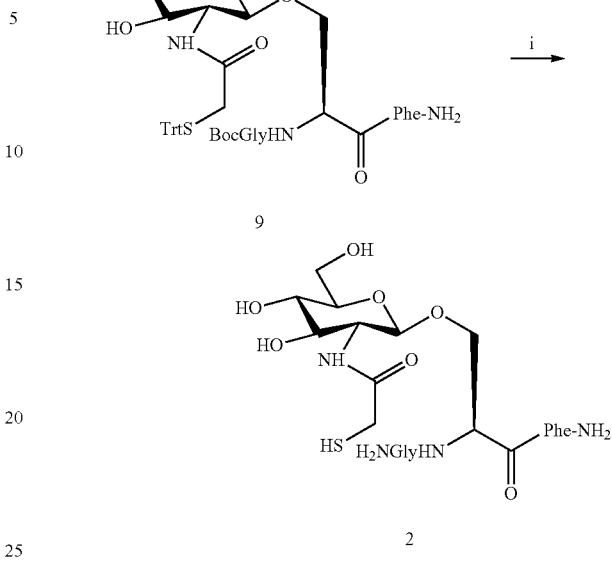

(a) FmocSer-OAllyl, TMSOTf, $CH_2Cl_2$, Molecular Sieves, −78° C.; (b) Zn, AcOH; (c) TrtS-$CH_2$—COOH, HBTU, DIEA, DMF; (d) 20% piperidine in DMF; (e) Boc-Gly-OH, HBTU, HOBt, DIEA, DMF; (f) Pd(PPh$_3$)$_4$, NMA, THF, (g) H-Phe-NH$_2$, HBTU, HOBt, DIEA, DMF; (h) 0.05N NaOH, MeOH, pH~10; (i) TFA/Et3SiH/H$_2$O (9/0.5/0.5).

Example 2

Compound 5: Compound 4 (5.54 g, 8.92 mmol) was added to Fmoc-Ser-OAllyl (3.92 g, 10.70 mmol) and MS (AW-300, 5 g) in dry $CH_2Cl_2$ (30 mL). The reaction was kept under argon at room temperature for 1 h. The reaction mixture was then brought to −78° C. and TMSOTf (174 μL, 0.89 mmol) was added slowly. The reaction mixture was stirred at −78° C. for 1.5 h and quenched with addition of DIEA (155.3 μL, 0.89 mmol). The reaction mixture was filtered and filtrate was diluted with 20 mL of $CH_2Cl_2$ and washed with water. The organic layer was dried over MgSO$_4$ and concentrated for flash column chromatography (EA/Hex, 1:2). The purified product (6.28 g, 85%) was then suspended in 20 mL of AcOH, and then Zn dust was added. The reaction mixture was stirred at rt for 8 h. After filtration the solvent was removed under vacuum, the residue was applied on flash column chromatography (EA/Hex, 3:1) to give compound 5 (4.36 g, 88%).

Example 3

Compound 6: Compound 5 (1.0 g, 1.4 mmol) was added to preactivated S-trityl-2-mercaptoactic acid (932.4 mg, 2.8 mmol) with HBTU (1.06 g, 2.8 mmoL) and DIEA (1 mL, 5.6 mmoL) in dry DMF (10 mL). The reaction mixture was stirred under argon at rt for 2 h. The reaction solution was diluted with 80 mL of ethylacetate and washed with water, then brine. The organic layer was dried over MgSO$_4$ and concentrated for flash column chromatography (EA/Hex 1:2). Compound 6 (1.0 g, 90%) was obtained as a white solid. $^1$H-NMR (CDCl$_3$, 500 MHz): δ 7.76 (d, 2H, J=7.7 Hz), 7.60 (t, 2H, J=7.3 Hz), 7.13-7.42 (m, 20H), 5.87 (d, 1H, J=7.7 Hz), 5.67 (d, 1H, J=8.0 Hz), 5.31 (d, 1H, J=16.9 Hz), 5.21 (d, 1H, J=10.2 Hz), 5.16 (t, 1H, J=9.5 Hz), 4.96 (t, 1H, J=9.5 Hz), 4.64 (d, 1H, J=5.1 Hz), 4.56 (d, 1H, J=7.7 Hz), 4.50 (m, 1H), 4.36 (dd, 1H, J=9.2, 6.2 Hz), 4.20-4.25 (m, 2H), 4.06-4.12 (m, 3H), 3.80 (dd, 1H, J=10.6, 3.3 Hz), 3.60-3.66 (m, 2H), 3.01 (d, 1H, J=15.1 Hz), 3.07 (d, 1H, J=15.1 Hz), 2.05 (s, 1H), 2.00 (s, 1H), 1.97 (s, 1H); $^{13}$C-NMR (CDCl$_3$, 500 MHz): δ 170.61, 170.32, 169.40, 169.29, 169.17, 156.07, 143.90, 143.74, 141.23, 131.50, 129.41, 128.25, 128.18, 127.67, 127.12, 127.09, 127.06, 125.37, 125.25, 119.87, 118.51, 100.62, 71.91, 71.22, 69.03, 68.48, 68.06, 67.17, 66.18, 62.03, 54.44, 54.28, 47.03, 36.33, 20.68, 20.64, 20.57; HRMS (ESI-TOF) calcd for $C_{54}H_{54}N_2O_{13}S$ [M+Na]$^+$ 993.3239. Found: 993.3244.

Example 4

Compound 7: Compound 6 was dissolved in 20% piperidine in DMF and stirred at rt for 45 min. After removing all the solvents under vacuum, the residue was subjected to flash column chromatography (EA/Hex 4:1, and then MeOH/CH$_3$Cl 1:9). The purified product (1.30 g, 1.74 mmol), BocGly-OH (913 mg, 5.21 mmol), HBTU (1.32 g, 3.48 mmol), and HOBt (533 mg, 3.48 mmol) were dissolved in DMF (15 mL) under Ar and then DIEA (3.03 mL, 17.4 mmol) was added. This reaction mixture was stirred at rt for 2 h. After removing all the solvents, the residue was subjected to flash column chromatography (EA/Hex 1:1) to give compound 7 (1.42 g, 90%). HRMS (ESI-TOF) calcd for $C_{46}H_{55}N_3O_{14}S$ [M+H]$^+$ 906.3477. Found: 906.3480.

Example 5

Compound 8: Compound 7 (660 mg, 0.73 mmol) was suspended in THF (10 mL), N-methylaniline (792 μL, 7.3 mmol) and (PPh$_3$)$_4$Pd were added subsequently. The reaction mixture was stirred at rt for 45 min. After removing the solvent, the residue was subjected to flash column chromatography (EA/Hex 4:1, then MeOH/CH$_3$C$_{1-8:1}$) to give the product (545 mg, 86%). The purified product (520 mg, 0.60 mmol), NH$_2$Phe-NH$_2$ (361 mg, 1.8 mmol), HBTU (456 mg, 1.20 mmol), and HOBt (184 mg, 1.20 mmol) were dissolved in DMF (15 mL) under argon and then DIEA (1.04 mL, 6.01 mmol) was injected. The reaction mixture was stirred at rt for 2 h. After removing all the solvents, the residue was subjected to flash column chromatography (EA/Hex 4:1 then MeOH/CHCl$_3$ 1:9) to furnish compound 8 (395 mg, 65%). HRMS (ESI-TOF) calcd for $C_{52}H_{61}N_5O_{14}S$ [M+H]$^+$ 1012.4008. Found: 1012.4001.

Example 6

Compound 9: Compound 8 (250 mg, 0.24 mmol) was dissolved in MeOH, 0.05 N NaOH was added dropwise until pH reached around 10. The reaction mixture kept stirred at rt for 1 h. The reaction was neutralized with the acidic resin to pH 7 and then was concentrated under vacuum. The residue was subjected to flash column chromatography (MeOH/CHCl$_3$ 1:9 then 1:5) to furnish compound 9 (178 mg, 82%). $^1$H-NMR (CDCl$_3$/MeOD, 500 MHz): δ 7.18-7.40 (m, 20H), 4.56-4.45 (m, 1H), 4.47 (brs, 1H), 4.28 (d, 1H, J=8.1 Hz), 3.78-3.86 (m, 2H), 3.70-3.78 (m, 2H), 3.59-3.65 (m, 2H), 3.45 (dd, 1H, J=9.9, 8.4 Hz), 3.33-3.41 (m, 3H), 2.95-3.02 (m, 3H), 1.44 (s, 9H); $^{13}$C-NMR (CDCl$_3$/MeOD, 500 MHz): δ 173.97, 170.85, 170.10, 169.63, 156.38, 143.75, 136.84, 129.12, 128.71, 128.09, 127.73, 126.64, 126.35, 101.14, 79.82, 75.96, 73.83, 70.25, 68.27, 66.97, 61.02, 55.66, 54.50, 53.20, 43.47, 36.49, 36.34, 27.80; HRMS (ESI-TOF) calcd for $C_{46}H_{55}N_5O_{11}S$ [M+Na]$^+$ 908.3511. Found: 908.3508.

Example 7

Compound 2: 10 mL of TFA/Et$_3$SiH/CHCl$_3$ (9:0.5:0.5) were added under Ar to compound 9. The reaction was stirred at rt for 40 min. After removing most of TFA, the deprotected glycopeptide was precipitated by adding cold Et$_2$O. The white precipitate was collected and re-suspended in a small amount of H$_2$O. The crude product was filtered through 0.45 μm syringe filter and then it was subjected to HPLC for purification. After lyophilization, the pure compound 2 as a white powder was ready for the next ligation step. HRMS (ESI-TOF) calcd for $C_{22}H_{33}N_5O_9S$ [M+Na]$^+$ 566.1891. Found: 566.1875.

Example 8

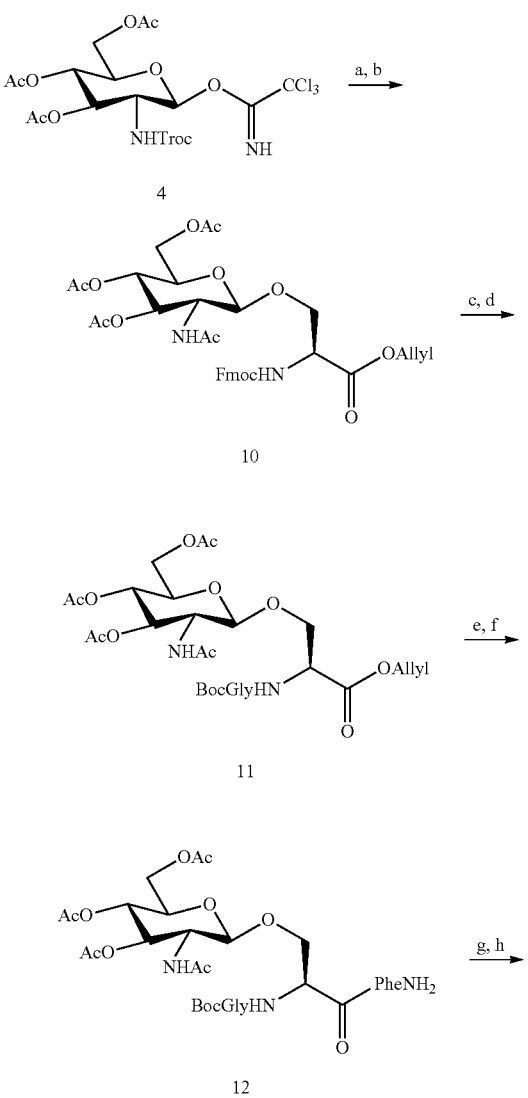

Synthetic Scheme for glycopeptide 3

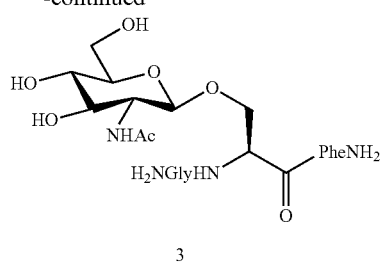

3

(a) FmocSer-OAllyl, TMSOTf, CH₂Cl₂, Molecular Sieves, −78° C.; (b) Zn, Ac₂O; (c) 20% piperidine in DMF; (d) Boc-Gly-OH, HBTU, HOBt, DIEA, DMF; (e) Pd(PPh₃)₄, NMA, THF, (f) H-Phe-NH₂, HBTU, HOBt, DIEA, DMF; (g) 0.05N NaOH, MeOH, pH-10; (h) 95% TFA in H₂O.

Example 9

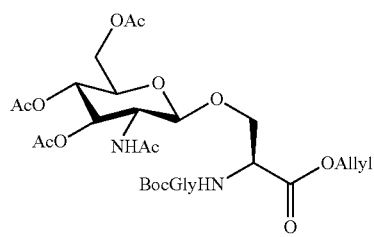

Compound 11: HRMS (ESI-TOF) calcd for $C_{27}H_{41}N_3O_{14}$ [M+Na]⁺654.2481. Found: 654.2473.

Example 10

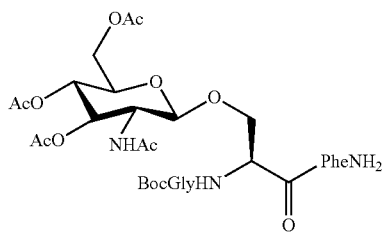

Compound 12: ¹H-NMR (CDCl₃/MeOD, 500 MHz): δ 7.57 (s, 1H), 7.22-7.32 (m, 5H), 5.19 (t, 1H, J=9.5 Hz), 4.98 (t, 1H, J=9.5 Hz), 4.60-4.64 (m, 2H), 4.47 (m, 1H), 4.26 (dd, 1H, J=12.4, 5.1 Hz), 4.10-4.16 (m, 1H), 3.70-3.88 (m, 5H), 3.38 (s, 1H), 3.24-3.30 (m, 1H), 3.01 (dd, 1H, J=14.3, 9.1 Hz), 2.07 (s, 3H), 2.04 (s, 3H), 2.02 (s, 3H), 1.93 (s, 3H), 1.46 (s, 9H); ¹³C-NMR (CDCl₃/MeOD, 500 MHz): δ 173.77, 171.80, 170.86, 170.78, 170.20, 169.51, 169.10, 156.50, 136.40, 128.51, 127.93, 126.27, 100.49, 79.57, 77.19, 72.03, 71.29, 68.14, 68.02, 61.50, 54.16, 54.02, 53.25, 52.96, 48.77, 43.18, 36.47, 27.47, 21.80, 19.72, 19.62, 19.56; HRMS (ESI-TOF) calcd for $C_{33}H_{47}N_5O_{14}$ [M+Na]⁺738.3192. Found: 738.3180.

Example 11

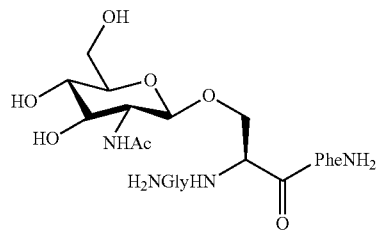

Compound 3: HRMS (ESI-TOF) calcd for $C_{22}H_{33}N_5O_9$ [M+H]⁺512.2351. Found: 512.2373.

Example 12

Synthetic Scheme for glycopeptide 1

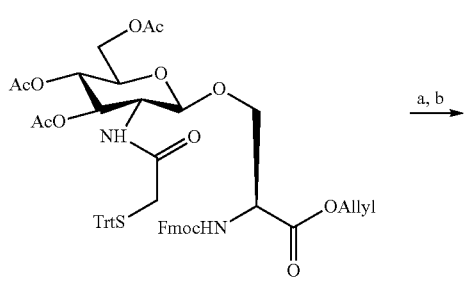

6

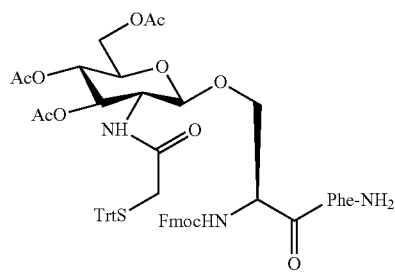

13

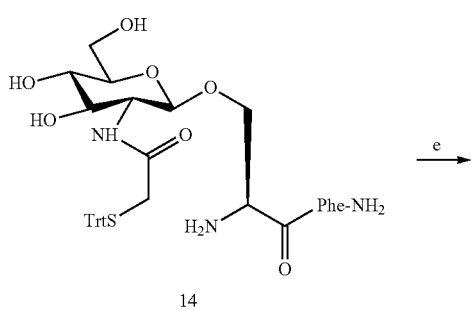

14

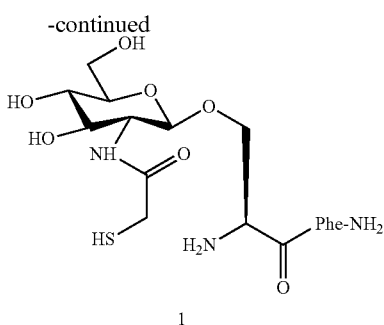

(a) Pd(PPh$_3$)$_4$, NMA, THF; (b) H-Phe-NH$_2$, HBTU, HOBt, DIEA, DMF; (c) 20% piperidine in DMF; (d) 0.05 N NaOH, MeOH, pH~10; (e) TFA/Et3SiH/H$_2$O (9/0.5/0.5).

Example 13

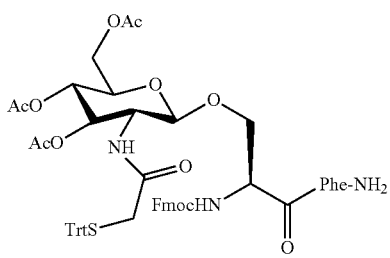

Compound 13: HRMS (ESI-TOF) calcd for C$_{60}$H$_{60}$N$_4$O$_{13}$S [M+H]$^+$1077.3950. Found: 1077.3932.

Example 14

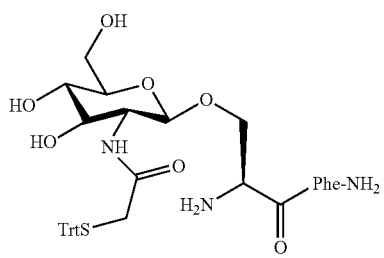

Compound 14: HRMS (ESI-TOF) calcd for C$_{45}$H$_{50}$N$_4$O$_{11}$S [M+H]$^+$855.3269. Found: 855.3269.

Example 15

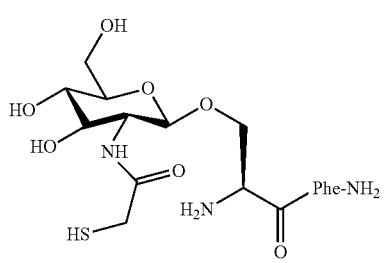

Compound 1: HRMS (ESI-TOF) calcd for C$_{20}$H$_{30}$N$_4$O$_8$S [M+H]$^+$487.1857 Found: 487.1852.

Example 16

Solid Phase Peptide Synthesis

General Methods.

Tetrahydrofuran (THF) was distilled over sodium/benzophenone, and methylene chloride (CH$_2$Cl$_2$) was distilled over calcium chloride. Reagents of commercial quality were purchased and used without further purification. Glycosylation experiments were performed by using molecular sieves (AW 300), which were flame-dried right before the reaction under high vacuum. Analytical thin-layer chromatography (TLC) was performed using silica gel 60 F$_{254}$ glass plates, compound spots were visualized by UV light (254 nm) and by staining with citric ammonium molybdate. Flash chromatography was performed on silica gel 60 Geduran® (35-75 µm, EM Science). $^1$H, $^{13}$C-NMR spectra were recorded on a Bruker AMX-500 MHz spectrometer. Coupling constants (J) are reported in hertz, and chemical shifts are reported in parts per million (ppm) relative to tetramethylsilane (TMS, 0.0 ppm).

Preloading of 3-(Tritylthio)Propanoic Acid onto the MBHA-Linker:

Resin loadings were aimed at approximately 300 µmol/g by adding the resin in excess. First, the resin was washed (5×DCM, 3 min 5% DIEA/DCM, 5×DCM, 5×DMF). For preactivation of the 3-(tritylthio)propanoic acid, PyBOP (1 eq.) was added to a 0.1 M solution of the 3-(tritylthio)propanoic acid in DMF containing 2 eq. NMM. After 5 min of preactivation, the mixture was added to the resin. After 2 h the resin was washed (5×DMF, 5×DCM, 3 min 5% DIPEA/DCM, 5×DCM, 5×DMF). For capping the resin was treated with acetic anhydride/pyridine (1:9) (2×10 min), washed (5×DMF, 10×DCM) and finally dried in vacuo.

Solid-phase chemistry was carried out in syringes, equipped with teflon filters, purchased from Torviq. Unless otherwise described, all reactions were carried out at room temperature. Preparative HPLC was performed on a Hitachi (D-7000 HPLC system) instrument using a preparative Column (Varian Dynamax 250×21.4 mm, S/N 3059 Microsorb 60-8 C18) and a flow rate of 8 mL/min. DMF was purchased in biotech grade. Commercial regents were used without further purification. Resins, protected amino acids and PyBOP were purchased from Novabiochem.

Example 17

Solid-Phase Synthesis According to Boc-Strategy

Boc Cleavage: After treatment with 5% m-Cresol/TFA (2×4 min, 4 mL), the resin was washed with DCM (8×4 mL) and with DMF (5×4 mL). Coupling: After preactivation of 4 eq protected amino acid (final concentration 0.1 M in DMF) for 5 min using 4 eq PyBOP and 8 eq NMM, the solution was added to the resin. After 30 min, the resin was washed with DMF (5×4 mL), DCM (5×4 mL) and DMF (5×4 mL). Capping: Acetic anhydride/pyridine (1:9, 4 mL) was added to the resin. After 5 min the resin was washed with DMF (5×4 mL) and DCM (5×4 mL). Terminal capping: Acetic anhydride/pyridine (1:9, 4 mL) was added to the resin. After 10 min the resin was washed with DMF (5×4 mL) and DCM (8×4 mL). Cleavage: A mixture of TFMSA/TFA/thioanisol (2:8:1) was added to the resin. After 3 h, the resin was washed with TFA (4×4 mL) Work-up: The combined solutions were concentrated in vacuo. The residue was dissolved in water, purified by preparative HPLC and analyzed by MALDI-TOF/MS (matrix: α-Cyano-4-hydroxycinnamic acid).

Example 18

Ac-Leu-Tyr-Arg-Ala-Gly-S(CH$_2$)$_2$CONH$_2$ 15. (SEQ ID NO:3 corresponds to unmodified amino acids): Starting from 400 mg (100 μmol) of MBHA-resin preloaded with 3-(tritylthio) propanoic acid, the linear assembly was performed following the Boc strategy. Yield: 50.6 mg (71.5 μmol, 72%). MALDI-TOF/MS (m/z): 708.8 ([M+H]$^+$, calcd 708.8); C$_{31}$H$_{49}$N$_9$O$_8$S (707.84).

Example 19

Ac-Leu-Tyr-Arg-Ala-Ala-S(CH$_2$)$_2$CONH$_2$ 16. (SEQ ID NO:4 corresponds to unmodified amino acids): Starting from 400 mg (100 μmol) of MBHA-resin preloaded with 3-(tritylthio) propanoic acid, the linear assembly was performed following the Boc strategy. Yield: 39 mg (54 μmol, 54%). MALDI-TOF/MS (m/z): 723.0 ([M+H]$^+$, calcd 722.9); C$_{32}$H$_{51}$N$_9$O$_8$S (721.87).

Example 20

Ac-Leu-Tyr-Arg-Ala-Val-S(CH$_2$)$_2$CONH$_2$ 17. (SEQ ID NO:5 corresponds to unmodified amino acids): Starting from 400 mg (100 μmol) of MBHA-resin preloaded with 3-(tritylthio) propanoic acid, the linear assembly was performed following the Boc strategy.

MALDI-TOF/MS (m/z): 750.6 ([M+H]$^+$, calcd 750.9); C$_{34}$H$_{55}$N$_9$O$_8$S (749.92).

Example 21

Ac-Leu-Tyr-Arg-Ala-His-S(CH$_2$)$_2$CONH$_2$ 18. (SEQ ID NO:6 corresponds to unmodified amino acids): Starting from 400 mg (100 μmol) of MBHA-resin preloaded with 3-(tritylthio) propanoic acid, the linear assembly was performed following the Boc strategy. Yield: 31 mg (39.3 μmol, 39%). MALDI-TOF/MS (m/z): 789.4 ([M+H]$^+$, calcd 788.9); C$_{35}$H$_{53}$N$_{11}$O$_8$S (787.93).

Example 22

Figure 2:
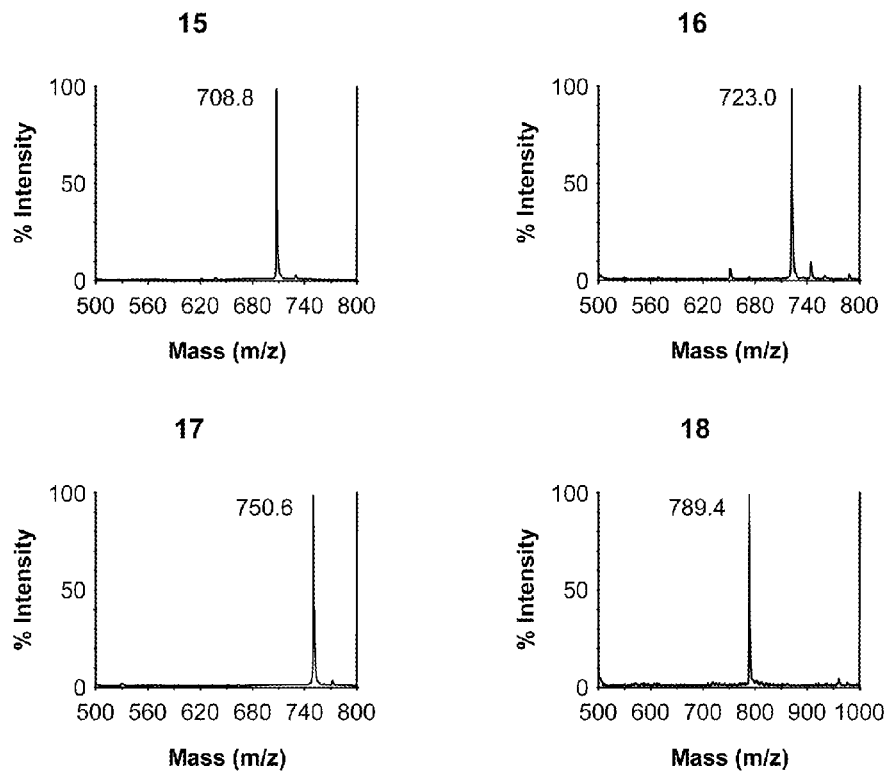
FIG. 2 shows MALDI-TOF spectra of the thioester peptides 15-18 as indicated.

MALDI-TOF spectra of the thioester peptides 15-18. FIG. 2.

Example 23

Chemical Ligation

The ligation of unprotected synthetic peptide segments was performed as follows: 0.2 M phosphate buffer (pH 8.5) containing 6 M guanidine was degassed with argon for 10 minutes before use. Peptides were dissolved at final concentration of 10 mM followed by the addition of 2% thiophenol. The ligation reaction was performed in a heating block at 37° C. and was vortexed periodically to equilibrate the thiol additive. The reaction was monitored by using LCMS (Agilent 1100 LC coupled to an Agilent 1100 single quadrapole mass spectrometer, column is an Agilent SB C8 50×4.6 mm) and/or HPLC {ton a Hitachi D-7000 HPLC system instrument using a analytical Column (XTeraMS, C18 3.5 μm, 4.6×100 mm) and a flow rate of 1 mL/min}.

A typical example for glycopeptide ligation and preparative purification as follows: 2.8 mg glycopeptide 2 was added to a solution of 4.4 mg (1.1 eq) thioester peptide Ac-LYRAG-C(O)S—(CH$_2$)$_2$—CONH$_2$ 15 (SEQ ID NO:3 corresponds to unmodified amino acids) in 600 μL 0.2 M phosphate buffer (pH 8.5) containing 6 M guanidine and 12 μL thiophenol. The ligation reaction was performed in a heating block at 37° C. and was vortexed periodically to equilibrate the thiol additive. After 12 h, TCEP (tris(2-carboxethyl) phosphate hydrochloride; 50 mM) was added to reduce any disulfide bond formation. The reaction was then purified using reversed phase HPLC {on a Hitachi D-7000 HPLC system instrument using a semipreparative Column, Vydac C-18 10 μm, 10×250 mm) and a flow rate of 5 mL/min. Linear gradients of acetonitrile in water/0.1% TFA were used to elute the bound peptides. The fraction possessed the expected mass were collected and lyophilized to give 4.4 mg of pure glycopeptide 19 corresponds to 76% yield.

Different ligation conditions at different pH (pH 7-9) and varying the thiol additives such as 2-mercaptoethansulfonate (MES), Benzyl mercaptan, thiophenol and without thiol were tested. Surprisingly, the reaction proceeded well in most of these conditions, however we found that the use of 2% thiophenol in 200 mM phosphate buffer (pH 8.5) containing 6 M guanidine gave the cleanest reaction by HPLC analysis. The use of MES (1 mg/ml) was superior in term of rate acceleration as the reaction was completed in less than 5 h, however we observed a higher rate hydrolysis of the peptide thioester. We also prepared peptide-α-phenyl thioester with glycine at the C-terminal, which was used directly in the ligation mixture without other thiol additives. In this model peptide, the reaction was completed within 4 h.

The effect of the C-terminal amino acid of peptide thioester on the ligation rate:

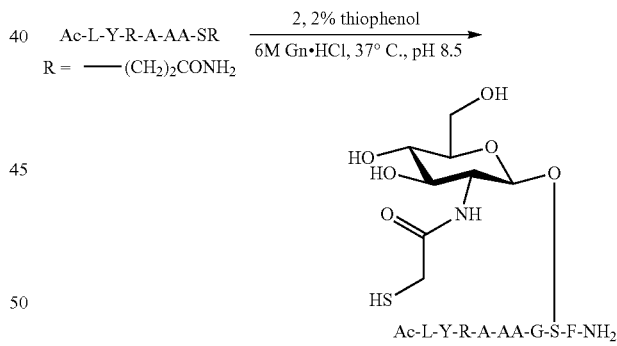

| Entry | -AA- | Ligation Junction | t$_{1/2}$(h) | Obsd Mass$^a$/Calcd(Da) |
|---|---|---|---|---|
| 1 | Gly | Gly-Gly | ~5 | 1146.4 ± 0.2 (1146.52) |
| 2 | His | His-Gly | ~5 | 1226.5 ± 0.2 (1226.55) |
| 3 | ALa | Ala-Gly | ~10 | 1160.4 ± 0.2 (1160.53) |
| 4 | Val | Val-Gly | >48 | 1188.5 ± 0.2 (1188.56) |

(LYRA-AA corresponds to SEQ ID NO:7 which represents the unmodified amino acids).

(LYRA-AA-GSF corresponds to SEQ ID NO:8 which represents the unmodified amino acids).

$^a$ Characterized by ESI-MS.

Example 24

General Procedure for Desulfurization

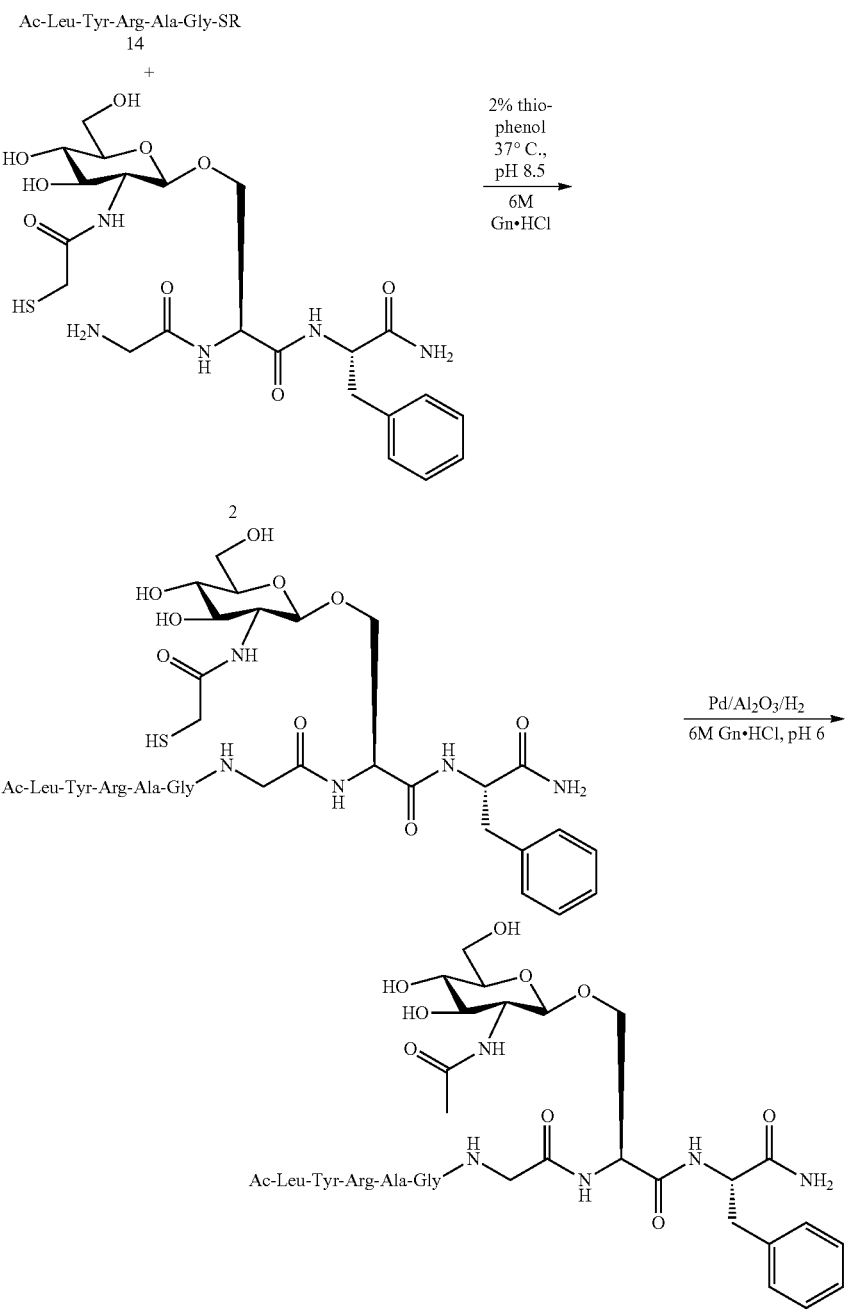

(Leu-Tyr-Arg-Ala-Gly corresponds to SEQ ID NO:3 which represents the unmodified amino acids).

(Leu-Tyr-Arg-Ala-Gly-Gly-Ser-Phe corresponds to SEQ ID NO:79 which represents the unmodified amino acids).

Desulfurization reactions were performed in 0.1 M phosphate buffer containing 6.0 M guanidine at pH 5.8, 10 mM TCEP at room temperature. The buffer was normally degassed by bubbling argon through for 10 min before each use. Pd/Al$_2$O$_3$ was added (10-20 times the weight of peptide) and the reaction was kept under hydrogen. The desulfurization reaction was followed analytical HPLC {on a Hitachi D-7000 HPLC system instrument using a analytical Column (XTeraMS, C18 3.5 µm, 4.6×100 mm) and a flow rate of 1 mL/min}.

The desulfurization was also done using Raney nickel, which was used in 10 times the peptide weight. Raney nickel was prepared as follows: Nickel acetate (600 mg) was dissolved in 15 mL of H$_2$O, and then sodium borohydride (100 mg) was slowly added with stirring. The black amorphous nickel precipitate was filtered and washed with distilled water until the washing became neutral. The nickel was then transferred into a closed bottle and stored in H$_2$O. In the case of Raney nickel, no hydrogen gas was needed for the reaction, however the reaction was usually slower (12 h) than the reduction with Pd/Al$_2$O$_3$.

Example 25

Figure 3:
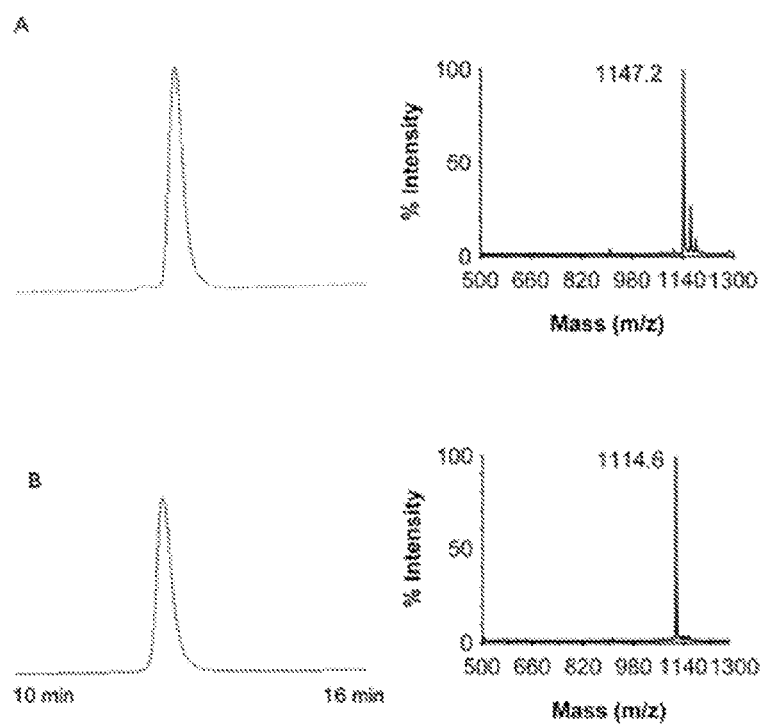
FIG. 3 shows analysis of purified ligation products. A: HPLC and MALDI-TOF analysis of the purified ligation product 19 from ligation of 2 and thioester peptide 15. B: HPLC and MALDI-TOF analysis of the crude desulfurization reaction product 20 of the ligated product 19 between 2 and thioester peptide 15, using Pd/Al2O-3 under hydrogen.

A) HPLC and MALDI-TOF analysis of the purified ligation product 19 from ligation of 2 and thioester peptide 15. The product was monitored at 214 nm on a Hitachi D-7000 HPLC system using a analytical Column (XTeraMS, C18 3.5 mm, 4.6×100 mm) and a flow rate of 1 mL/min. B) HPLC and MALDI-TOF analysis of the crude desulfurization reaction product 20 of the ligated product 19 between 2 and thioester peptide 15, using Pd/Al$_2$O$_3$ under hydrogen. The reaction was monitored and 214 nm on a Hitachi D-7000 HPLC system using analytical Column (XTeraMS, C18 3.5 mm, 4.6×100 mm) and a flow rate of 1 mL/min. See FIG. 3.

Example 26

Figure 4:
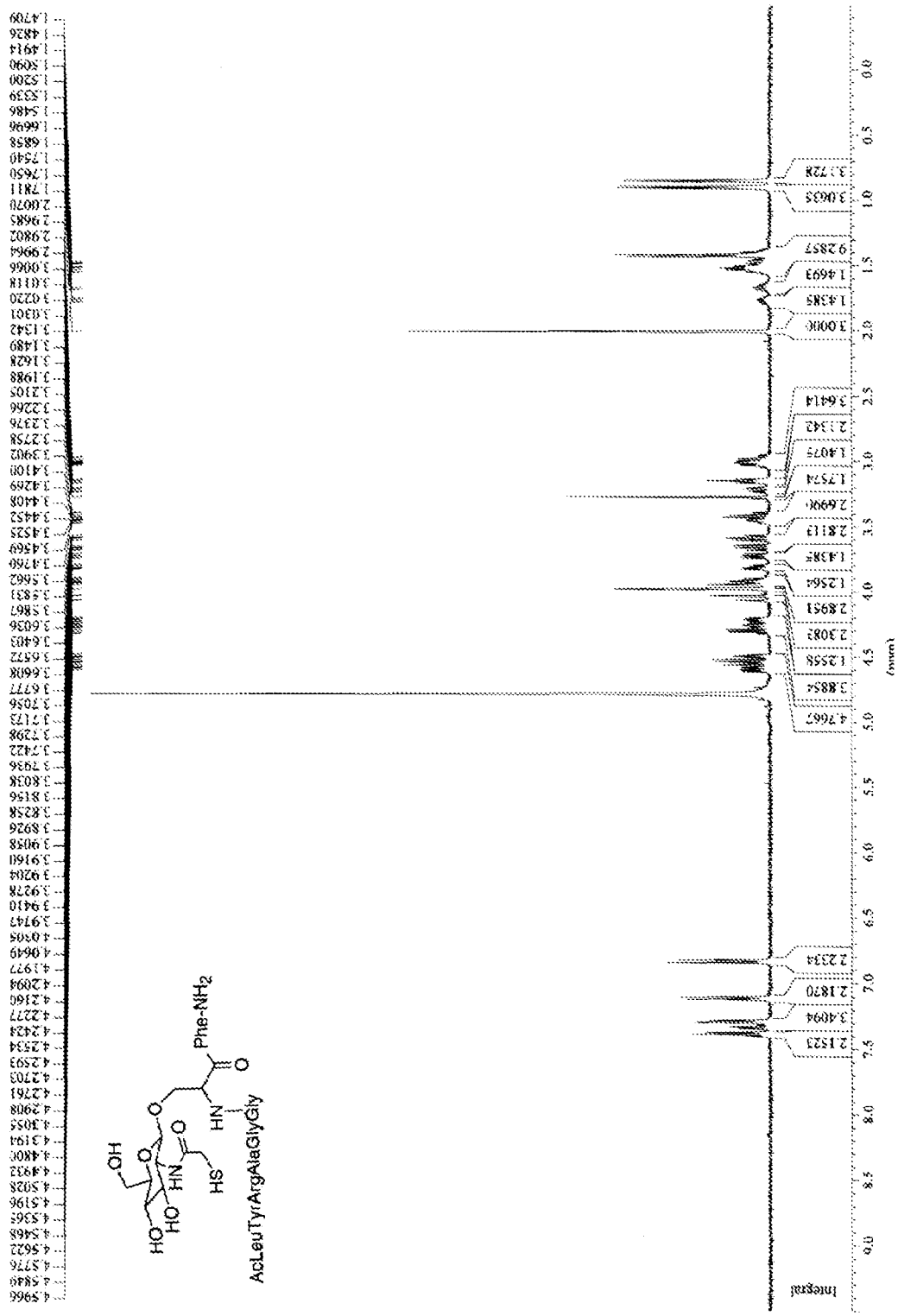
FIG. 4 shows $^1$H-NMR Spectrum of the ligation product 19.

$^1$H-NMR Spectrum of the ligation product 19 (D$_2$O, Bruker MAX-500 MHZ). (Leu-Tyr-Arg-Ala-Gly-Gly corresponds to SEQ ID NO:9 which represents the unmodified amino acids). FIG. 4.

Example 27

Figure 5:
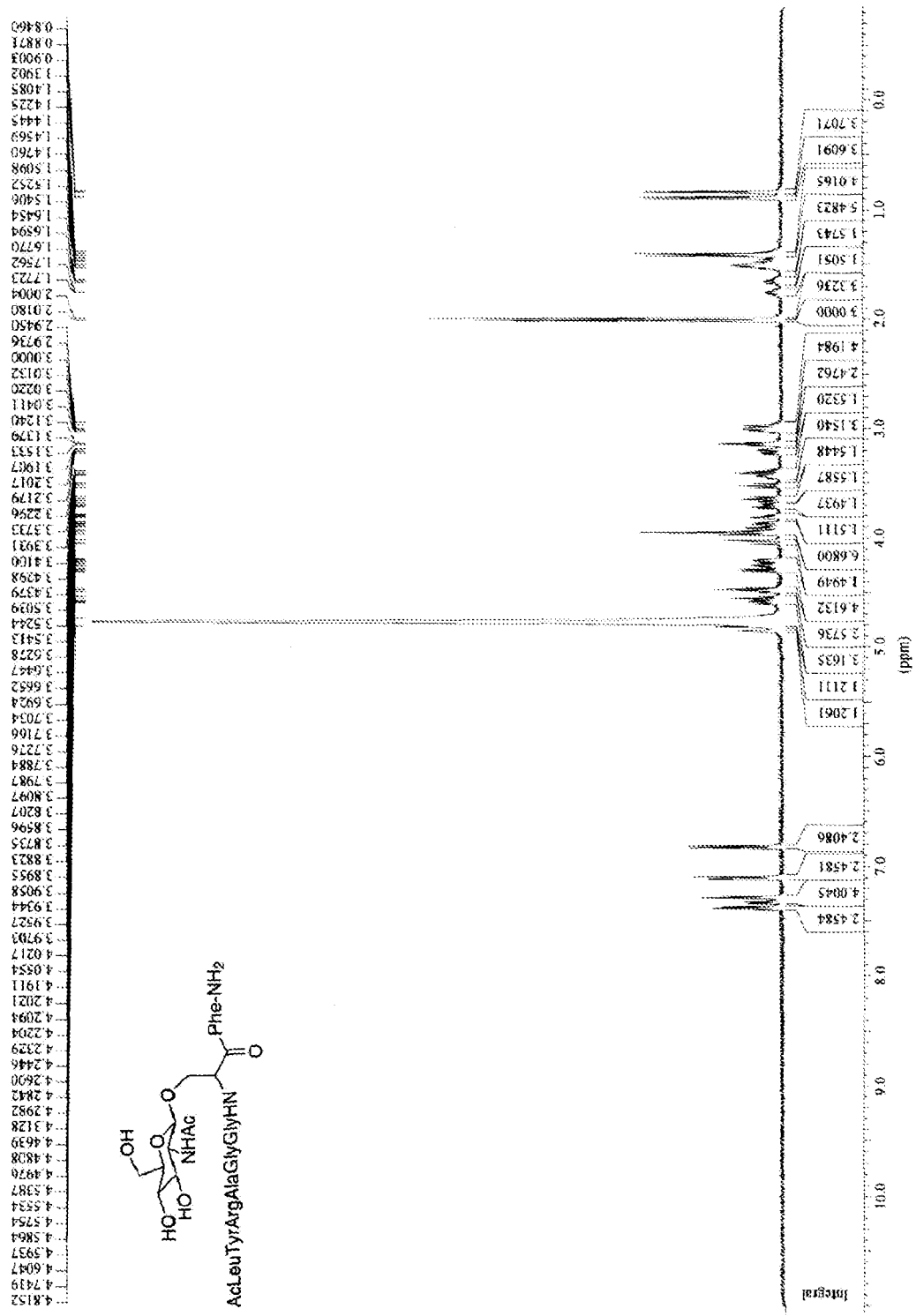
FIG. 5 shows $^1$H-NMR spectra of the desulfurization product 20.

$^1$H-NMR spectra of the desulfurization product 20 (D$_2$O, Bruker MAX-500 MHZ). (Leu-Tyr-Arg-Ala-Gly-Gly corresponds to SEQ ID NO:9 which represents the unmodified amino acids). FIG. 5.

Example 28

Analysis of Thioester Intermediate Versus Ligation Product by Mass Spectrometry

During analysis of the of the different ligation reactions by LCMS, it was observed that fragmentation occurred as is shown below. If the ligation product was formed, the fragmentation would yield the entire ligated peptide without the sugar part. However, if the ligation intermediate is formed but no peptide bond formation

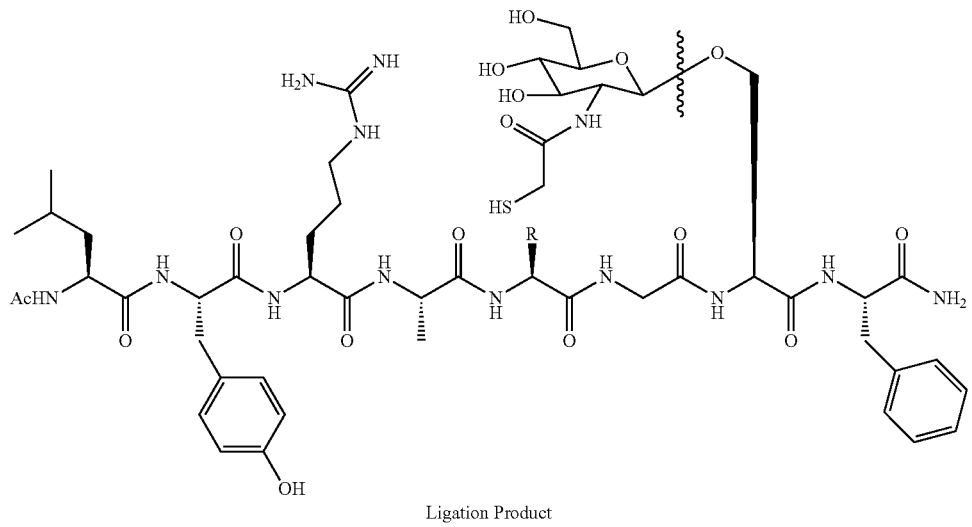

Ligation Product

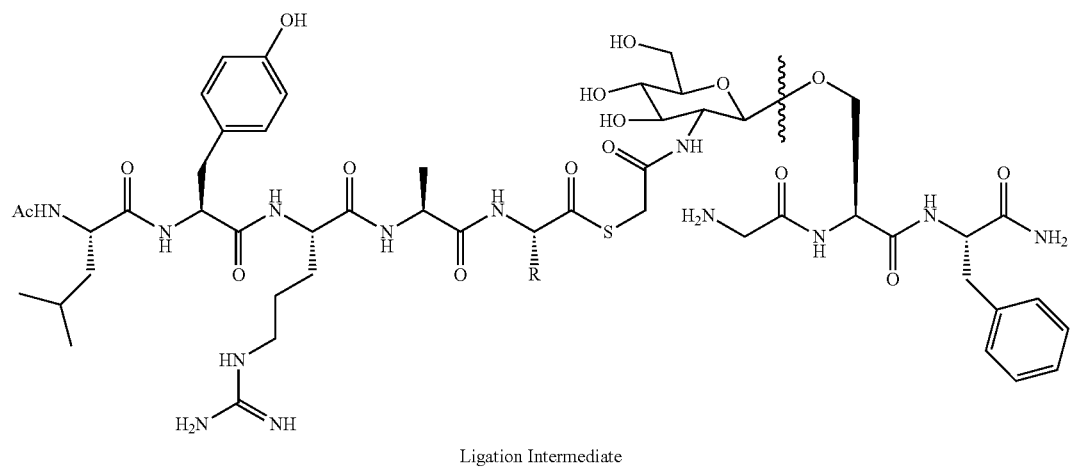

Ligation Intermediate occurs, the fragmentation yields the starting peptide thioester with the mercaptoacetamido-sugar attached.

(Leu-Tyr-Arg-Ala-X-Gly-Ser-Phe corresponds to SEQ ID NO:80 which represents the unmodified amino acids.)

(Leu-Tyr-Arg-Ala-X corresponds to SEQ ID NO:81 which represents the unmodified amino acids.)

Fragmentation at the anomeric center on the sugar part of the glycopeptides product and the intermediate from the ligation reaction.

| Entry | Amino acid side chain (R) | Observered mass of ligation pordcut/ intermediate | Calculated mass (Da) of the fragmentation at the anomeric center Product | Intermediate | Observered mass (Da) from fragmentation |
|---|---|---|---|---|---|
| 1 | Gly | 1146.4 ± 0.2 | 911.4 | 839.38 | 911.3 ± 0.2 |
| 2 | His | 1226.5 ± 0.2 | 991.5 | 919.4 | 991.5 ± 0.2 |
| 3 | Ala | 1160.4 ± 0.2 | 925.5 | 853.4 | 925.4 ± 0.2 |
| 4 | Val | 1188.5 ± 0.2 | 953.5 | 880.4 | 880.3 ± 0.2 |

The masses of the ligation products and the different fragments observed by the mass spectrometry. Entry 1, 2, 3 correspond to the formation of the desired ligation product. However, in the case of the valine thioester (Entry 4) the ligation intermediate was observed as the major product after 24 h. In this case, rasing the pH of the ligation mixture to pH 11 caused the disappearance of this intermediate and the appearance of the hydrolyzed thioester. Also, the addition of excess MES thiol additive caused transthioesterification which resulted into the formation MES thioester peptide. None of these changes occurred in the cases of entries 1, 2, 3.

Figure 6:
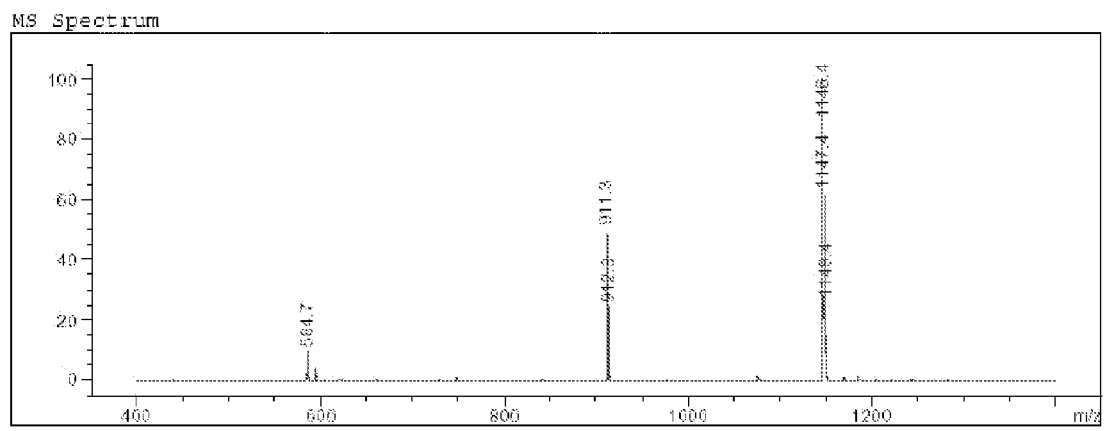
FIG. 6 includes charts showing MS spectrum results. A: Corresponds to Entry 1; B: Corresponds to Entry 2; C: Corresponds to Entry 3; D: Corresponds to Entry 4; E: Corresponds to the desulfurization product 20 from glycopeptide 2 and thioester peptide 15.
Figure 6:
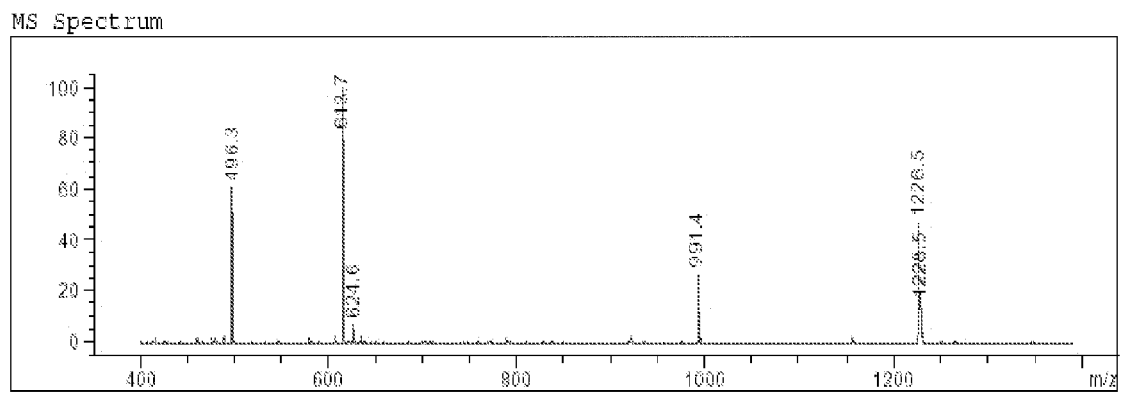
Figure 6:
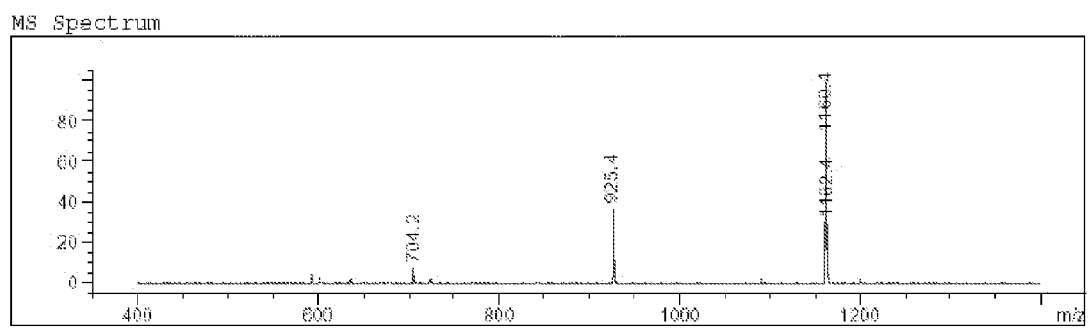
Figure 6:
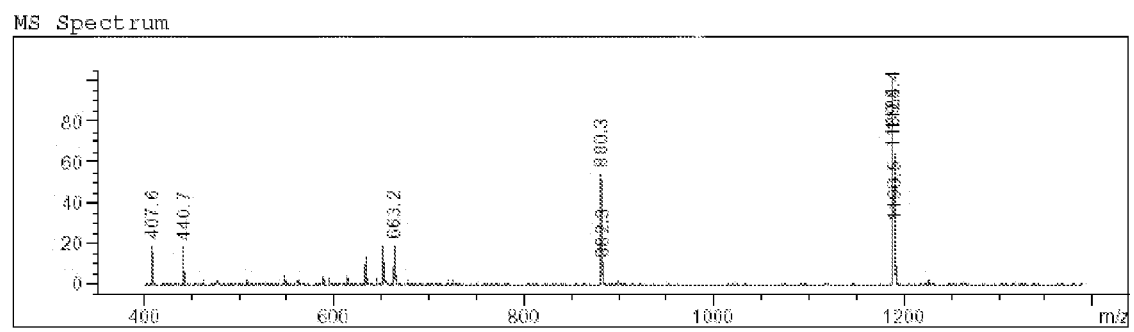
Figure 6:
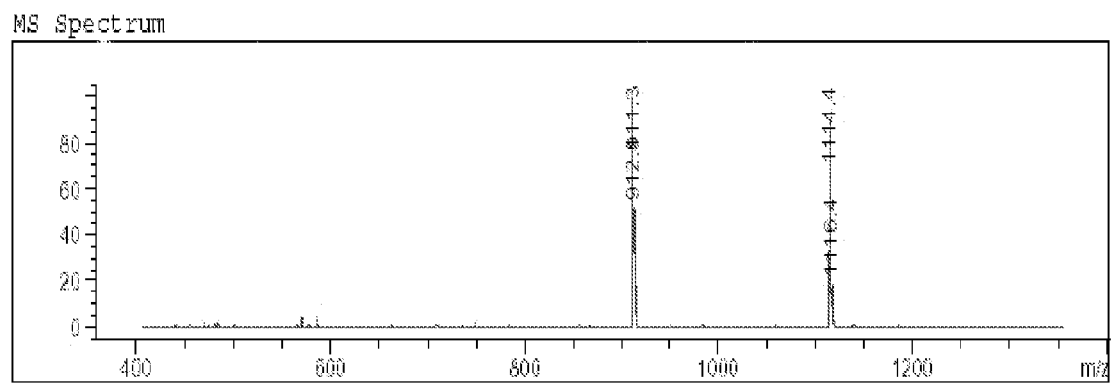

The observed fragmentation at the anomeric center on the sugar part of the glycopeptides product and the ligation intermediate. Measurements were done using Agilent 1100 LC coupled to an Agilent 1100 single quadrapole mass spectrometer, column is an Agilent SB C8 50×4.6 mm. See FIG. 6. A: Corresponds to Entry 1; B: Corresponds to Entry 2; C: Corresponds to Entry 3; D: Corresponds to Entry 4; E: Corresponds to the desulfurization product 20 from glycopeptide 2 and thioester peptide 15.

Example 29

Synthesis of the Building Blocks 24a and 24b

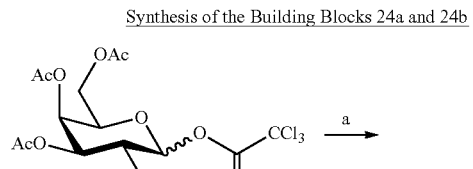
21

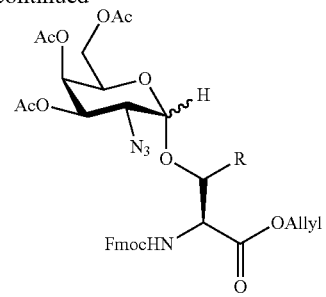
(22a) R = CH₃
(22b) R = H

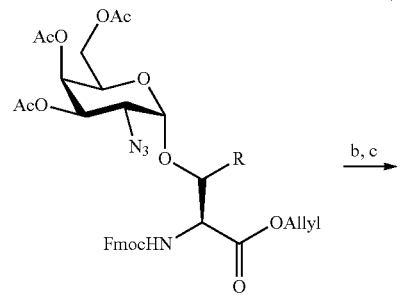
22aα (R = CH₃)
22bβ (R = H)

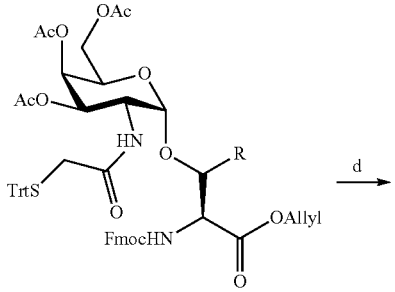
23a (R = CH₃)
23b (R = H)

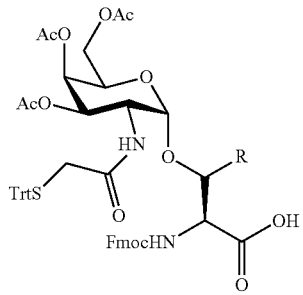
24a (R = CH₃)
24b (R = H)

Reagents and Conditions: (a) Fmoc-Thr-OAllyl (R=CH₃ for 22a) or Fmoc-Ser-OAllyl (R=H for 22b), TMSOTf, molecular sieves AW 300, CH₂Cl₂, −70° C., 78-83%, α/β=4/3;
(b) Zn/AcOH; (c) TrtS-CH₂COOH, HBTU, DIEA, DMF, 84% (2 steps); (d) Pd(PPh₃)₄, NMA, THF, 95%.

Compound 22aα. Compound 21 (5.0 g, 10.5 mmol) and Fmoc-Thr-OAllyl (4.83 g, 12.7 mmol) were mixed and dried under high vacuum overnight prior to the reaction. The mixture was then dissolved in anhydrous CH₂Cl₂ (30 mL) under N₂. 3.0 g of fresh flame-dried molecule sieves were added and the mixture was stirred at room temperature for 1 h. Afterwards, it was cooled down to −78° C., followed by adding TMSOTf (203.9 µL, 1.066 mmol) slowly to the reaction solution. Then the mixture was kept at −78° C. and stirred for 45 min. Once the reaction was down, it was quenched by adding Et₃N and the temperature was allowed to rise to room temperature. Molecule sieves were removed by filtration through Celite, and the filtrate was concentrated under vacuum. The crude product was purified by flash column chromatography (20-50% EtOAc in hexane) to give the pure α product (3.31 g, 4.77 mmol, 45.4%). $^1$H-NMR (CDCl₃, 500 MHz): δ 7.76 (d, 2H, J=7.4 Hz), 7.62-7.64 (m, 2H), 7.36-7.41 (m, 2H), 7.30-7.34 (m, 2H), 5.90-5.99 (m, 1H), 5.68 (d, 1H, J=9.6 Hz), 5.46 (brs, 1H), 5.26-5.39 (m, 3H), 5.05 (d, 1H, J=3.3 Hz), 4.69 (d, 1H, J=5.2 Hz), 4.41-4.48 (m, 3H), 4.36 (dd, 1H, J=10.3, 7.3 Hz), 4.26-4.29 (m, 2H), 4.09 (d, 1H, J=6.6 Hz), 3.67 (dd, 1H, J=11.4, 3.7 Hz), 2.14 (s, 3H), 2.07 (s, 3H), 2.03 (s, 3H), 1.36 (d, 3H, J=6.2 Hz); $^{13}$C-NMR (CDCl₃, 125 MHz):δ170.2, 169.9, 169.7, 156.7, 143.7, 143.6, 141.2, 141.1, 131.2, 127.6, 127.0, 125.2, 125.1, 119.9, 119.8, 119.2, 99.3, 76.9, 68.1, 67.4, 67.3, 66.9, 66.4, 61.7, 58.7, 57.6, 47.0, 20.6, 20.5, 20.4, 18.4; HRMS (ESI-TOF) calcd for $C_{34}H_{38}N_4O_{12}$ [M+H]⁺: 695.2559. Found: 695.2553.

Compound 23a. Compound 22aα (2.68 g, 3.86 mmol) was dissolved in AcOH (25 mL), followed by adding Zinc (15.0 g). The reaction mixture was stirred for 4 h at room temperature. Once the reaction was done, Zinc was filtered off through Celite and washed with CH₂Cl₂. The filtrate was concentrated under vacuum. The concentrated residue was then purified by flash column chromatography (20% hexane in EtOAc) to give the pure amine product (2.40 g, 3.62 mmole, 94%). $^1$H-NMR (CDCl₃, 500 MHz): δ 7.76 (d, 2H, J=7.4 Hz), 7.64 (d, 2H, J=5.9 Hz), 7.38-7.41 (m, 2H), 7.30-7.35 (m, 2H), 5.90-5.98 (m, 1H), 5.77 (d, 1H, J=9.2 Hz), 5.34-5.38 (m, 2H), 5.27 (d, 1H, J=10.7 Hz), 4.97 (d, 1H, J=3.0 Hz), 4.88-4.92 (m, 1H), 4.65-4.74 (m, 2H), 4.41-4.49 (m, 3H), 4.23-4.33 (m, 3H), 4.08-4.10 (m, 2H), 3.15 (dd, 1H, J=10.7, 3.0 Hz), 2.11 (s, 3H), 2.04 (s, 3H), 2.03 (s, 3H), 1.35 (d, 3H, J=6.2 Hz); $^{13}$C-NMR (CDCl₃, 125 MHz):δ170.5, 170.3, 170.2, 170.1, 156.5, 143.8, 143.7, 141.2, 131.3, 127.6, 127.0, 125.1, 125.1, 119.9, 119.9, 119.3, 101.8, 77.3, 71.8, 67.4, 67.3, 67.2, 66.4, 62.1, 58.6, 49.7, 47.0, 20.7, 20.6, 20.5, 18.1; HRMS (ESI-TOF) calcd for $C_{34}H_{40}N_2O_{12}$ [M+H]⁺: 669.2654. Found: 669.2641. The amine (650 mg, 0.973 mmol) was dissolved in DMF (15 mL). TrtS-CH₂COOH (651 mg, 1.95 mmol), HBTU (740 mg, 1.95 mmol) and DIPEA (678 µL, 3.89 mmol) were added to the amine subsequently. The reaction was stirred at room temperature for 2 h. Once the reaction was done, the reaction solution was concentrated under vacuum. The concentrated residue was then purified by flash column chromatography (20-40% EtOAc in hexane) to give pure compound 23a (877.7 mg, 0.892 mmol, 91%). $^1$H-NMR (CDCl₃, 500 MHz): δ 8.00 (brs, 1H), 7.77 (d, 2H, J=7.3 Hz), 7.63 (d, 2H, J=7.3 Hz), 7.16-7.47 (m, 19H), 5.95-6.01 (m, 1H), 5.72-5.82 (m, 2H), 5.39 (brs, 1H), 5.20-5.25 (m, 2H), 5.03-5.08 (m, 1H), 4.86-4.89 (m, 1H), 4.37-4.50 (m, 6H), 4.19-4.28 (m, 3H), 4.04-4.13 (m, 2H), 2.14 (s, 3H), 2.03 (s, 3H), 1.95 (s, 3H), 1.28 (d, 3H, J=6.2 Hz); $^{13}$C-NMR (CDCl₃, 125 MHz):δ 171.2, 170.7, 170.6, 170.4, 169.2, 163.0, 156.9, 144.5, 144.2, 144.1, 141.7, 131.4, 129.9, 128.4, 128.1, 127.5, 127.3, 125.5, 125.4, 120.5, 120.4, 120.1, 99.8, 68.6, 67.7, 67.6, 67.6, 66.6, 62.5, 58.8, 48.2, 47.6, 39.0, 37.1, 36.9, 31.8, 21.2, 21.1, 21.0, 18.5; HRMS (ESI-TOF) calcd for $C_{55}H_{56}N_2O_{13}S$ [M+Na]⁺: 1007.3395. Found: 1007.3390.

Compound 24a. Compound 23a (750 mg, 0.762 mmol) was dissolved in THF (20 mL). Pd (PPh₃)₄ (88.0 mg, 0.076 mmol) and N-methylaniline (827 µL, 7.62 mmol) were added, and then the reaction mixture was stirred at room temperature for 45 min. Once the reaction was done, the solution was concentrated under vacuum. The crude product was purified by flash column chromatography (50% EtOAc in hexane then 10% MeOH in CH₂Cl₂) to give pure compound 24a (690 mg, 0.731 mmol, 95%). $^1$H-NMR (MeOD, 500 MHz): δ 7.75 (d, 2H, J=7.7 Hz), 7.57-7.63 (m, 3H), 7.47-7.50 (m, 1H), 7.31-7.33 (m, 6H), 7.12-7.26 (m, 11H), 5.38 (brs, 1H), 5.09 (dd, 1H, J=11.4, 2.9 Hz), 4.96 (brs, 1H), 4.24-4.45 (m, 6H), 4.13-4.16 (m, 2H), 4.03-4.09 (m, 3H), 2.99 (d, 1H, J=13.2 Hz), 2.91 (d, 1H, J=13.2 Hz), 2.10 (s, 3H), 1.96 (s, 3H), 1.91 (s, 3H), 1.19 (d, 3H, J=7.0 Hz); $^{13}$C-NMR (MeOD, 125 MHz):δ172.2, 172.1, 171.9, 171.9, 158.9, 145.7, 145.5, 145.1, 142.7, 142.7, 133.8, 133.8, 133.2, 133.1, 130.8, 130.1, 130.0, 129.1, 128.9, 128.3, 128.1, 126.2, 126.1, 121.1, 121.1, 100.3, 77.6, 69.7, 68.9, 68.3, 68.2, 67.8, 63.4, 61.6, 60.3, 37.6, 21.0, 21.0, 20.7, 20.7, 19.2, 14.6; HRMS (ESI-TOF) calcd for $C_{52}H_{52}N_2O_{13}S$ [M+Na]⁺: 967.3082. Found: 967.3059.

Compound 22bα. Compound 21 (1.33 g, 2.81 mmol) and Fmoc-Ser-OAllyl (858.8 mg, 2.34 mmol) were mixed together and dried under high vacuum overnight prior to the reaction. The mixture was then dissolved in anhydrous CH₂Cl₂ (15 mL) under N₂. 1.5 g of fresh flame-dried molecule sieves were added and the reaction mixture was stirred at room temperature for 1 h. Afterwards, the reaction mixture was cooled down to −78° C., followed by adding TMSOTf (54.3 µL, 0.281 mmol) slowly to the reaction solution. The reaction was kept at −78° C. and stirred for 45 min. Once the reaction was done, it was quenched by adding Et₃N and the temperature was allowed to rise to room temperature. Molecule sieves were then filtered off through Celite, and the filtrate was concentrated under vacuum. The crude product was purified by flash column chromatography (20-50% EtOAc in hexane) to give pure α product (872 mg, 1.28 mmol, 45%). $^1$H-NMR (CDCl₃, 500 MHz): δ 7.76 (d, 2H, J=7.7 Hz), 7.62 (dd, 2H, J=7.0, 3.7 Hz), 7.40 (dd, 2H, J=7.7, 7.7 Hz), 7.32 (td, 2H, J=7.7, 3.3 Hz), 5.94 (m, 2H), 5.44 (brs, 1H), 5.28-5.38 (m, 3H), 4.94 (d, 1H, J=3.3 Hz), 4.69-4.71 (m, 2H), 4.59-4.60 (m, 1H), 4.41 (d, 2H, J=7.0 Hz), 4.25 (t, 1H, J=7.3 Hz), 4.19 (t, 1H, J=6.6 Hz), 4.13 (dd, 1H, J=10.6, 2.9 Hz), 4.00-4.04 (m, 2H), 3.63 (dd, 1H, J=11.0, 3.3 Hz), 2.14 (s, 3H), 2.06 (s, 3H), 1.97 (s, 3H); $^{13}$C-NMR (CDCl₃, 125 MHz): δ 170.3, 169.8, 169.6, 169.1, 155.7, 143.7, 141.2, 131.2, 127.7, 127.6, 127.0, 125.0, 119.9, 119.2, 99.2, 69.7, 67.8, 67.4, 67.2, 67.1, 66.5, 61.6, 57.3, 54.4, 47.0, 20.5, 20.5, 20.4; HRMS (ESI-TOF) calcd for $C_{33}H_{36}N_4O_{12}$ [M+Na]⁺: 703.2222. Found: 703.2208.

Compound 23b. The amine (822 mg, 1.26 mmol) [HRMS (ESI-TOF) calcd for $C_{33}H_{38}N_2O_{12}$ [M+H]⁺: 655.2497. Found: 655.2499] was dissolved in DMF (10 mL). TrtS-CH₂COOH (840 mg, 2.51 mmol), HBTU (953 mg, 2.51 mmol) and DIPEA (875 µL, 5.03 mmol) were added to the amine subsequently. The reaction was stirred at room temperature for 2 h. Once the reaction was done, the solution was concentrated under vacuum. The concentrated residue was then purified by flash column chromatography (20-40% EtOAc in hexane) to give pure compound 23b (1.03 g, 1.06 mmol, 84%). $^1$H-NMR (CDCl₃, 500 MHz): δ 7.76 (d, 2H, J=7.3 Hz), 7.60 (d, 2H, J=5.2 Hz), 7.36-7.41 (m, 8H), 7.25-7.32 (m, 8H), 7.19-7.22 (m, 3H), 5.90-5.96 (m, 2H), 5.78-5.86 (m, 1H), 5.35 (d, 1H, J=2.9 Hz), 5.27 (d, 1H, J=17.3 Hz), 5.23 (d, 1H, J=10.3 Hz), 4.98 (dd, 1H, J=11.4, 2.6 Hz), 4.71 (brs, 1H), 4.41-4.56 (m, 6H), 4.22 (t, 1H, J=6.6 Hz), 4.06-4.11 (m, 2H), 3.98-4.01 (m, 2H), 3.85-3.87 (m, 1H), 2.13 (s, 3H), 1.96 (s, 3H), 1.93 (s, 3H); $^{13}$C-NMR (CDCl₃, 125 MHz): δ 170.4, 170.2, 170.0, 169.2, 168.5, 155.6, 143.8, 143.6, 141.2, 131.0, 129.3, 128.0, 127.6, 127.0, 124.9, 119.9, 119.3, 98.8, 69.8, 68.0, 67.6, 67.2, 67.0, 66.2, 61.8, 54.3, 47.6, 46.9, 38.5, 36.3, 20.6, 20.5, 20.4; HRMS (ESI-TOF) calcd for $C_{54}H_{54}N_2O_{13}S$ [M+Na]⁺: 993.3239. Found: 993.3240.

Compound 24b. Compound 23b (420 mg, 0.433 mmol) was dissolved in THF (10 mL), followed by adding Pd(PPh₃)₄ (50.0 mg, 0.043 mmol) and N-methylaniline (470 µL, 4.33 mmol) subsequently. The reaction mixture was stirred at room temperature for 45 min. Once the reaction was done, the reaction solution was concentrated under vacuum. The crude product was purified by flash column chromatography (50% EtOAc in hexane then 10% MeOH in CH$_2$Cl$_2$) to give pure compound 24b (390 mg, 0.420 mmol, 96%). $^1$H-NMR (MeOD, 500 MHz): δ 7.76-7.78 (m, 2H), 7.60-7.65 (m, 2H), 7.16-7.41 (m, 19H), 5.36 (dd, 1H, J=2.6 Hz), 5.11-5.14 (m, 1H), 4.82 (brs, 1H), 4.35 (dd, 1H, J=11.4, 3.3 Hz), 4.27-4.32 (m, 3H), 4.22 (t, 1H, J=6.6 Hz), 4.17 (t, 1H, J=6.6 Hz), 4.05 (dd, 1H, J=11.0, 6.3 Hz), 3.99 (dd, 1H, J=11.0, 7.0 Hz), 3.91-3.93 (m, 1H), 3.82 (dd, 1H, J=10.3, 5.1 Hz), 2.82-2.93 (m, 2H), 2.13 (s, 3H), 1.92 (s, 3H), 1.89 (s, 3H); $^{13}$C-NMR (MeOD, 125 MHz): δ 172.3, 172.2, 171.9, 171.8, 158.4, 146.0, 145.7, 145.4, 145.3, 142.7, 133.9, 133.2, 133.1, 130.8, 130.1, 130.0, 129.9, 129.2, 129.1, 128.9, 128.8, 128.3, 128.1, 128.0, 126.3, 121.1, 99.8, 70.4, 69.8, 68.8, 68.4, 68.2, 68.1, 63.0, 57.2, 37.5, 20.9, 20.7; HRMS (ESI-TOF) calcd for C$_{51}$H$_{50}$N$_2$O$_{13}$S [M+Na]$^+$: 953.2926. Found: 953.2892.

Example 30

Synthesis of α-O-Linked Glycopeptides Using Sugar-Assisted Ligation (SAL)

To check the ligation efficiency of sugar-assisted ligation (SAL), four model α-O-linked glycopeptides 25a-b and 26a-b as well as thioester peptide Cys(Acm)$^{37}$-Gly$^{52}$ were prepared based on the sequence of diptericin, which exhibits Gly-Val ligation junction. The ligation conditions used here are similar to the conditions we used in our previous studies, however thiophenol was excluded.

SAL of α-linked Glycopeptides

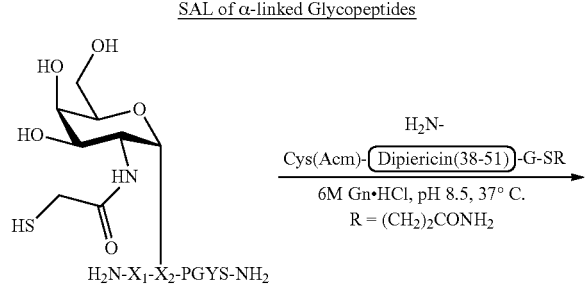

H$_2$N-Cys(Acm)-[Diptericin(38-51)]-G-SR
6M Gn·HCl, pH 8.5, 37° C.
R = (CH$_2$)$_2$CONH$_2$ H$_2$N-X$_1$-X$_2$-PGYS-NH$_2$
(SEQ ID NO: 10 corresponds to the unmodified amino acids.)

25a: X$_1$ = Gly, X$_2$ = Ser
25b: X$_1$ = Val, X$_2$ = Ser
26a: X$_1$ = Gly, X$_2$ = Thr
26b: X$_1$ = Val, X$_2$ = Thr

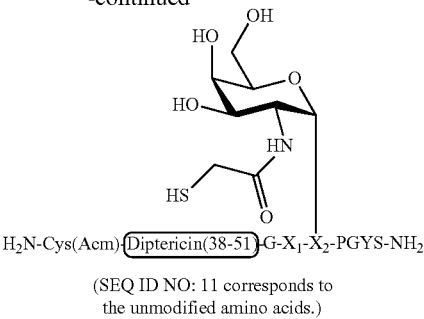

H$_2$N-Cys(Acm)-[Diptericin(38-51)]-G-X$_1$-X$_2$-PGYS-NH$_2$
(SEQ ID NO: 11 corresponds to the unmodified amino acids.)

| Entry | -X$_1$- | -X$_2$- | Ligation Junction | Thioester$^c$ $t_{1/2}$(h)$^a$ | (eqlv.) | Reaction Medium | Product Mass (Da) obsd$^b$ | calcd |
|---|---|---|---|---|---|---|---|---|
| 1 | Gly | Ser | Gly-Gly | ~4 | 1.2 | 0.2 M phosphate buffer | 2677.4 | 2677.4 |
| 2 | Val | Ser | Gly-Val | ~11 | 1.2 | 0.2 M phosphate buffer | 2720.4 | 2719.5 |
| 3 | Gly | Thr | Gly-Gly | ~4 | 1.2 | 0.2 M phosphate buffer | 2691.5 | 2691.4 |
| 4 | Val | Thr | Gly-Val | ~11 | 1.2 | 0.2 M phosphate buffer | 2733.6 | 2733.5 |
| 5 | Val | Thr | Gly-Val | ~14 | 1.2 | 0.2 M phosphate buffer + 2% PhSH | 2733.6 | 2733.5 |
| 6 | Val | Thr | Gly-Val | ~14 | 1.2 | 0.1 M phosphate buffer | 2733.6 | 2733.5 |
| 7 | Val | Thr | Gly-Val | ~9 | 1.5 | 0.2 M phosphate buffer | 2733.6 | 2733.5 |
| 8 | Val | Thr | Gly-Val | ~7 | 2.0 | 0.2 M phosphate buffer | 2733.6 | 2733.5 |

$^a$t$_{1/2}$ indicates the required reaction time for the reactant glycopeptide to reach 50% consumption.
$^b$Characterized by LCMS.
$^c$The concentration of the reactant glycopeptide in each reaction is 6 mM.

As shown above, α-O-linked glycopeptides can be successfully synthesized by SAL in an efficiency similar to β-O-linked and N-linked glycopeptides (entries 1-4). Notably, glycopeptides containing GalNAc(SH)-Thr reacted in similar rates as the glycopeptides containing GalNAc(SH)-Ser, despite the additional steric factor from the methyl group of threonine (entries 1-4). As expected, the ligation rate in the case of Gly-Val junction was faster in the absence of thiophenol (entries 4 and 5). Several conditions were also screened using glycopeptide 26b and thioester peptide Cys(Acm)$^{37}$-Gly$^{52}$ to optimize the ligation condition for the synthesis of diptericin. Measuring the reaction pH by microelectrode showed that the ideal reaction pH for SAL is 7.2~7.4. As shown above in the table "SAL of α-linked Glycopeptides", superior ligation efficiency was achieved by using more concentrated phosphate buffer that endows better pH stability (entries 4 and 6). In this pH range, the ligation reached its highest efficiency while giving a minimum amount of hydrolyzed thioester. Under the same conditions, the addition of 2 equivalents of peptide thioester, to compensate for the hydrolyzed thioester in this slow ligation, gave optimal ligation results (entries 4, 7 and 8).

Example 31

(A) Synthesis of the Building Block 30. (B) Synthesis of Glycopeptide Thioester Asp$^1$-Asn$^{36}$ Using the Side-Chain Anchoring Strategy.

(A)

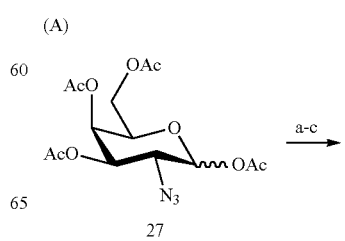

27

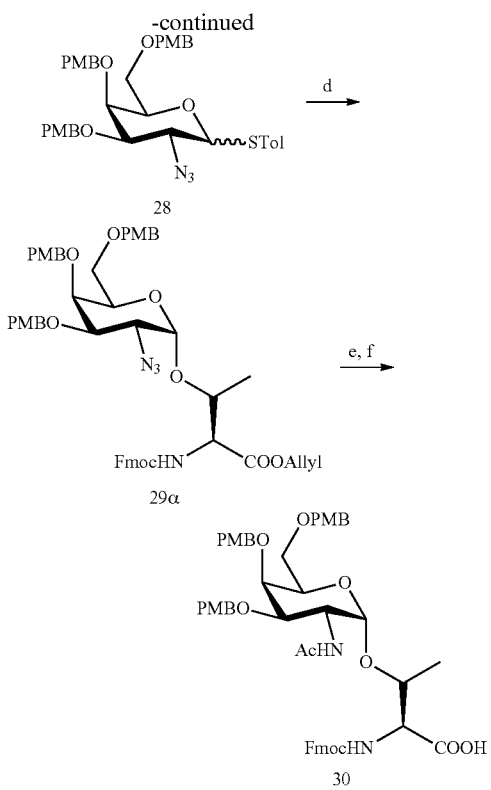

(B)

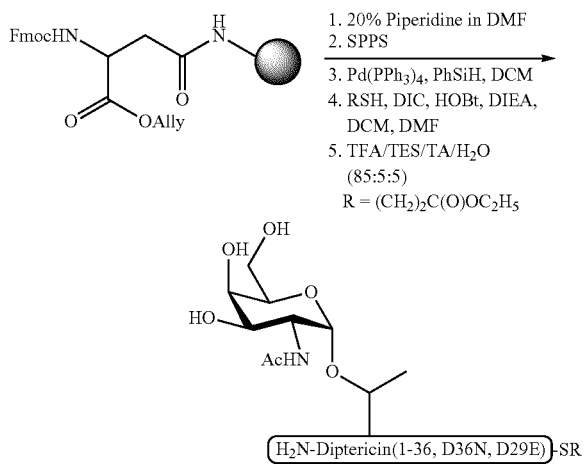

Reagents and Conditions: (a) BF$_3$·OEt$_2$, TolSH, CH$_2$Cl$_2$, 0° C. then rt; (b) NaOMe, MeOH, pH~11; (c) PMBCl, NaH, DMF, 0° C. then rt, 68% (3 steps); (d) Fmoc-Thr-OAllyl, NIS, cat. TfOH, molecular sieves AW 300, CH$_2$Cl$_2$, −15° C., 83%, α/β=3/2; (e) AcSH, pyridine, 86%; (f) Pd(PPh$_3$)$_4$, NMA, THF, 95%. TolSH=p-thiocresol, NIS=N-iodosuccinimide Compound 28α. Compound 27 (10.28 g, 27.55 mmol) and p-thiocresol (5.1 g, 41.3 mmol) were dissolved in CH$_2$Cl$_2$ (40 mL) under N$_{2(g)}$. The reaction solution was cooled down to 0° C. in ice bath. To this solution, BF$_3$·OEt$_2$ (6.92 mL, 55.1 mmol) was added slowly. Afterwards, the reaction temperature was allowed to gradually increase to room temperature. After 8 h, the reaction was quenched by slowly adding saturated NaHCO$_3$ and diluted with CH$_2$Cl$_2$. The product was washed with saturated NaHCO$_3$ and extracted with CH$_2$Cl$_2$. The organic layers were collected and concentrated under vacuum. The concentrated residue was then purified by flash column chromatography (20-40% EtOAc in hexane) to give the pure product (α and β mixtures, 10.3 g, 23.6 mmol, 85%). The purified thioglycoside were dissolved in MeOH. NaOMe (25% wt in MeOH) was added drop wisely to the reaction solution until the pH reached around 11-12. The reaction mixture was stirred at room temperature for 1 h and neutralized with acidic resin (Dowex 50WX2-200(H)). The resin was then filtered off and washed with CH$_2$Cl$_2$. The filtrate was concentrated under vacuum. The concentrated residue was then purified by flash column chromatography (5-10% MeOH in CH$_2$Cl$_2$). The pure thioglycoside (7.83 g, 25.2 mmol) was then dissolved in 60 mL of dry DMF at 0° C. and fully protected with PMB groups by adding PMBCl (20.5 mL, 151 mmol) and NaH (3.62 g, 151 mmol). The reaction mixture was stirred at room temperature for 2 h and quenched with MeOH. After removing MeOH, it was concentrated under vacuum. Then the product was extracted with EtOAc and washed with H$_2$O. The organic layers were collected and washed again with brine. After concentrating the organic layer under vacuum, the crude residue was purified by flash column chromatography (10-40% EtOAc in hexane) to give the pure PMB protected thioglycoside 28α and 28β, respectively. [15.5 g, 23.2 mmol (α+β), 92%]. $^1$H-NMR (CDCl$_3$, 500 MHz): δ 7.37 (d, 2H, J=8.1 Hz), 7.33 (d, 2H, J=8.8 Hz), 7.19 (d, 2H, J=8.5 Hz), 7.18 (d, 2H, J=8.8 Hz), 7.02 (d, 2H, J=7.8 Hz), 6.90 (d, 2H, J=8.4 Hz), 6.86 (d, 2H, J=8.5 Hz), 6.81 (d, 2H, J=8.5 Hz), 5.50 (d, 1H, J=5.5 Hz), 4.80 (d, 1H, J=11.0 Hz), 4.63-4.67 (m, 2H), 4.32-4.47 (m, 5H), 3.98 (brs, 1H), 3.80 (s, 3H), 3.79 (s, 3H), 3.77 (s, 3H), 3.74 (dd, 1H, J=10.6, 2.6 Hz), 3.55 (dd, 1H, J=9.2, 7.0 Hz), 3.47 (dd, 1H, J=9.2, 5.9 Hz), 2.29 (s, 3H); $^{13}$C-NMR (CDCl$_3$, 125 MHz): δ 159.4, 159.3, 159.2, 137.6, 132.7, 130.4, 129.9, 129.8, 129.7, 129.6, 129.5, 129.4, 129.3, 113.9, 113.7, 113.6, 87.9, 78.7, 74.4, 73.1, 73.0, 72.0, 70.4, 68.3, 60.3, 55.3, 55.2, 55.1, 21.0; HRMS (ESI-TOF) calcd for C$_{37}$H$_{41}$N$_3$O$_7$S [M+Na]$^+$: 694.2557. Found: 694.2556

Compound 28β. $^1$H-NMR (CDCl$_3$, 500 MHz): δ 7.43 (d, 2H, J=7.7 Hz), 7.27 (d, 2H, J=8.4 Hz), 7.18 (d, 2H, J=8.4 Hz), 7.13 (d, 2H, J=8.4 Hz), 6.96 (d, 2H, J=7.7 Hz), 6.80-6.87 (m, 6H), 4.75 (d, 1H, J=11.0 Hz), 4.60 (d, 1H, J=11.0 Hz), 4.54 (d, 1H, J=11.3 Hz), 4.43 (d, 1H, J=11.0 Hz), 4.40 (d, 1H, J=11.3 Hz), 4.33 (d, 1H, J=11.8 Hz), 4.31 (d, 1H, J=10.3 Hz), 3.86 (d, 1H, J=1.8 Hz), 3.73-3.78 (m, 11H), 3.57 (d, 1H, J=6.6 Hz), 3.49 (dd, 1H, J=6.3, 6.3 Hz), 3.34 (dd, 1H, J=9.5, 2.2 Hz), 2.26 (s, 3H); $^{13}$C-NMR (CDCl$_3$, 125 MHz): δ 159.2, 159.1, 158.8, 137.7, 133.0, 130.5, 129.7, 129.4, 129.3, 129.2, 129.1, 128.0, 113.7, 113.6, 113.3, 86.3, 82.0, 77.2, 73.8, 73.0, 71.7, 71.5, 68.0, 61.3, 55.0, 20.9; HRMS (ESI-TOF) calcd for C$_{37}$H$_{41}$N$_3$O$_7$S [M+Na]$^+$: 694.2557. Found: 694.2556.

Fmoc-Thr-O-Allyl.

Cesium carbonate (2.28 g, 7.0 mmol) was added to a suspension of Fmoc-Thr-OH (4.75 g, 13.9 mmol) in dry MeOH (40 mL) under N$_{2(g)}$. The reaction mixture was stirred at room temperature for 2 h and then evaporated to dryness under vacuum. The concentrated residue was further dried under high vacuum for another 2 h. Afterwards, the dried mixture was re-dissolved in dry DMF (40 mL) under $N_2$ and added with allylbromide (1.45 mL, 16.7 mmol). The reaction mixture was stirred at room temperature for 8 h. The white precipitate was filtered off through Celite and washed with $CH_2Cl_2$. The filtrate was concentrated under vacuum, and then was purified by flash column chromatography (25-50% EtOAc in hexane) to give the pure white powder (4.64 g, 12.2 mmol, 87%). $^1$H-NMR (CDCl$_3$, 500 MHz): δ 7.72 (d, 2H, J=7.4 Hz), 7.59 (d, 1H, J=5.9 Hz), 7.58 (d, 1H, J=5.9 Hz), 7.36 (d, 1H, J=7.3 Hz), 7.35 (d, 11-1, J=7.7 Hz), 7.27 (d, 1H, J=7.3 Hz), 7.25 (d, 1H, J=7.4 Hz), 5.92 (d, 1H, J=9.2 Hz), 5.82-5.89 (m, 1H), 5.29 (d, 1H, J=17.2 Hz), 5.20 (d, 1H, J=10.3 Hz), 4.62-4.64 (m, 2H), 4.36-4.41 (m, 4H), 4.20 (t, 1H, J=7.0 Hz), 1.23 (d, 3H, J=5.9 Hz); $^{13}$C-NMR (CDCl$_3$, 125 MHz): δ 170.8, 156.7, 143.6, 143.5, 141.1, 131.2, 127.5, 126.9, 125.0, 119.8, 118.7, 67.7, 67.0, 66.0, 59.1, 46.9, 19.7; HRMS (ESI-TOF) calcd for $C_{22}H_{23}NO_5$ [M+Na]$^+$: 404.1468. Found: 404.1468.

Compound 29α. Compound 28 (917 mg, 1.366 mmol) and Fmoc-Thr-OAllyl (624.7 mg, 1.639 mmol) were mixed and dried under high vacuum overnight prior to the reaction. Then, the reaction mixture was dissolved in dry $CH_2Cl_2$ under $N_2$. The fresh flame-dried molecular sieves (AW 300) (3 g) was added to the reaction mixture and stirred for about 2 h, afterwards, the reaction was cooled to −20° C., followed by adding N-iodosuccinimide (338.1 mg, 1.503 mmol). To this mixture, freshly prepared TfOH (0.05 equiv) was slowly added at −20° C. The reaction was stirred at −15° C. for 1 h. Once the reaction was done, it was quenched by adding saturated $Na_2S_2O_3$ $_{(aq)}$ and saturated $NaHCO_3$ $_{(aq)}$. The molecular sieves was filtered off through Celite and washed with $CH_2Cl_2$. The filtrate was extracted with $CH_2Cl_2$ and washed with saturated $Na_2S_2O_3$ $_{(aq)}$ and saturated $NaHCO_3$ $_{(aq)}$. After drying over $Na_2SO_4$, the filtrate was evaporated to dryness under vacuum. The concentrated residue was purified by flash column chromatography (25-50% EtOAc in hexane) to give a product (506.7 mg, 0.546 mmol, 40%). $^1$H-NMR (CDCl$_3$, 600 MHz): δ 7.76 (d, 2H, J=7.9 Hz), 7.64 (d, 1H, J=7.4 Hz), 7.63 (d, 1H, J=7.4 Hz), 7.39 (d, 1H, J=7.4 Hz), 7.38 (d, 1H, J=7.4 Hz), 7.33 (d, 2H, J=8.3 Hz), 7.31 (d, 1H, J=7.4 Hz), 7.30 (d, 1H, J=7.4 Hz), 7.20 (d, 2H, J=8.3 Hz), 7.17 (d, 2H, J=8.3 Hz), 6.90 (d, 2H, J=8.3 Hz), 6.86 (d, 2H, J=8.3 Hz), 6.81 (d, 2H, J=8.3 Hz), 5.89-5.96 (m, 1H), 5.74 (d, 1H, J=9.2 Hz), 5.35 (d, 1H, J=17.1 Hz), 5.25 (d, 1H, J=10.1 Hz), 4.90 (d, 1H, J=3.5 Hz), 4.78 (d, 1H, J=10.9 Hz), 4.66-4.68 (m, 2H), 4.61 (d, 1H, J=11.0 Hz), 4.39-4.49 (m, 5H), 4.31-4.36 (m, 2H), 4.28 (dd, 1H, J=7.0, 7.0 Hz), 4.01 (brs, 1H), 3.95 (dd, 1H, J=6.6, 6.6 Hz), 3.88 (dd, 1H, J=10.5, 2.2 Hz), 3.79 (s, 3H), 3.78 (s, 3H), 3.77 (s, 3H), 3.53 (dd, 1H, J=9.2, 7.5 Hz), 3.48 (dd, 1H, J=8.8, 5.7 Hz), 1.30 (d, 3H, J=5.5 Hz); $^{13}$C-NMR (CDCl$_3$, 150 MHz): δ169.9, 163.1, 159.4, 159.3, 159.2, 156.7, 143.9, 143.6, 141.2, 131.3, 130.3, 129.8, 129.7, 129.5, 129.4, 129.3, 127.6, 127.1, 127.0, 125.2, 125.1, 119.9, 119.3, 113.8, 113.7, 113.6, 99.5, 76.0, 74.7, 73.4, 73.1, 71.8, 69.9, 68.5, 67.3, 66.5, 59.5, 58.8, 55.1, 47.0, 18.7; HRMS (ESI-TOF) calcd for $C_{52}H_{56}N_4O_{12}$ [M+H]$^+$: 929.3967. Found: 929.3954.

Compound 30. Compound 29α (200 mg, 0.215 mmol) was dissolved in pyridine (1.2 mL) at 0° C., followed by adding AcSH (1.2 mL). The reaction temperature was then allowed to rise to room temperature. The reaction mixture was stirred for 4 h. Once the reaction was done, the mixture was evaporated to dryness under vacuum. The concentrated residue was purified by flash column chromatography (20%-50% EtOAc in hexane then 30% hexane in EtOAc) to give pure product for next allyl removal step. (174.7 mg, 0.185 mmol, 86%). $^1$H-NMR (CDCl$_3$, 600 MHz): δ 7.77 (d, 2H, J=7.4 Hz), 7.63 (d, 1H, J=6.5 Hz), 7.61 (d, 1H, J=6.1 Hz), 7.40 (d, 1H, J=7.9 Hz), 7.38 (d, 1H, J=7.9 Hz), 7.33 (d, 1H, J=7.9 Hz), 7.30 (d, 1H, J=7.4 Hz), 7.20-7.25 (m, 8H), 6.80-6.87 (m, 4H), 5.81 (m, 1H), 5.23-5.32 (m, 4H), 4.88 (d, 1H, J=11.0 Hz), 4.80 (d, 1H, J=3.5 Hz), 4.55-4.64 (m, 4H), 4.43-4.53 (m, 4H), 4.33-4.39 (m, 2H), 4.27 (dd, 1H, J=6.6, 6.6 Hz), 4.16 (m, 1H), 3.94 (brs, 1H), 3.87 (dd, 1H, J=6.6, 6.6 Hz), 3.79 (s, 3H), 3.77 (s, 3H), 3.73 (s, 3H), 3.47-3.55 (m, 2H), 1.94 (s, 3H), 1.22 (d, 3H, J=6.5 Hz); $^{13}$C-NMR (CDCl$_3$, 150 MHz): δ 170.5, 169.8, 162.9, 159.2, 159.1, 158.9, 156.2, 143.7, 143.4, 141.2, 141.1, 130.8, 130.5, 129.9, 129.8, 129.7, 129.6, 129.2, 129.1, 127.6, 127.0, 124.8, 124.7, 119.9, 119.8, 119.6, 113.7, 113.6, 113.4, 76.4, 76.3, 73.8, 73.1, 72.0, 71.0, 70.2, 68.5, 66.7, 66.0, 58.5, 55.1, 48.8, 47.1, 23.3, 18.3; HRMS (ESI-TOF) calcd for $C_{54}H_{60}N_2O_{13}$ [M+Na]$^+$: 967.3987. Found: 967.3984. In the allyl removal step, the product from previous step (720 mg, 0.762 mmol) was dissolved in THF (10 mL), followed by adding Pd(Ph$_3$P)$_4$ (88.1 mg, 0.076 mmol) and N-methylaniline (827 μL, 7.62 mmol) subsequently. The reaction mixture was stirred at room temperature for 45 min. Once the reaction was done, the reaction solution was evaporated to dryness under vacuum. The concentrated residue was then purified by flash column chromatography (50% EtOAc in hexane, then 10% MeOH in $CH_2Cl_2$) to give the pure compound 10 (655 mg, 0.724 mmol, 95%) $^1$H-NMR (d$^6$-DMSO, 600 MHz): δ 7.87 (d, 2H, J=7.5 Hz), 7.71 (d, 2H, J=7.0 Hz), 7.39 (d, 1H, J=7.0 Hz), 7.37 (d, 1H, J=7.0 Hz), 7.29 (t, 2H, J=7.0 Hz), 7.20-7.25 (m, 4H), 7.14 (d, 2H, J=8.3 Hz), 6.87-6.89 (m, 4H), 6.83 (d, 2H, J=8.3 Hz), 4.64 (dd, 2H, J=19.7, 11.0 Hz), 4.33-4.46 (m, 6H), 4.17-4.27 (m, 3H), 3.92-3.96 (m, 3H), 3.71 (s, 9H), 3.66-3.70 (m, 2H), 3.42-3.50 (m, 2H), 1.90 (s, 3H), 1.09 (d, 3H, J=6.1 Hz); $^{13}$C-NMR (d$^6$-DMSO, 125 MHz): δ 172.8, 170.1, 158.7, 158.6, 158.6, 156.2, 143.9, 143.8, 140.8, 130.9, 130.9, 130.1, 129.3, 129.2, 128.8, 127.6, 127.0, 125.2, 125.2, 124.9, 120.1, 113.6, 113.5, 113.4, 98.7, 79.3, 79.0, 78.8, 77.2, 75.2, 73.5, 72.0, 71.0, 69.4, 68.8, 65.4, 59.3, 55.0, 54.9, 48.7, 46.8, 23.1, 18.4; HRMS (ESI-TOF) calcd for $C_{51}H_{56}N_2O_{13}$ [M+Na]$^+$: 927.3674. Found: 927.3680.

Example 32

Solid-Phase Synthesis of Glycopeptide Val$^{53}$-Phe$^{82}$

The synthesis of the C-terminal glycopeptide segment (53-82) was started with H$_2$N-Phe-2-ClTrt-resin and carried out by using Fmoc strategy. For coupling the glycosylated amino acid onto the resin, we used 2 equivalents of building block 24a and left the reaction to shake for 24 h. Once the SPPS was completed, the acetate groups on the sugar were removed on the solid support by treating with hydrazine/MeOH (1/6) for 6 h. After this acetate removal step, the resin was washed with MeOH, DMF and $CH_2Cl_2$. The resulting glycopeptide was deprotected and cleaved from the resin by treating with TFA/H$_2$O/Et$_3$SiH/thioanisole (17/1/1/1) for 50 min at room temperature. The crude glycopeptide solution was evaporated to remove all the cleavage cocktail solution, and then the dried residue was re-dissolved in $H_2O/CH_3CN$ (1/1) for HPLC purification. The purified glycopeptide was lyophilized to give pure glycopeptide. (18% yield). ESI-MS: 3528 Da. (the peptide mass was reconstructed from the experimental mass-to-charge (m/z) ratios from all of the observed protonation states of the peptide).

Example 33

Synthesis of Thioester Peptide $Cys(Acm)^{37}$-$Gly^{52}$

The synthesis of the thioester peptide was begun with the preloading of 3-(tritylthio) propanoic acid onto MBHA resin LL. The detailed preloading procedure can be found in *J. Am. Chem. Soc.* 2006, 128, 5626-5627, which is incorporated herein by reference.

Solid-phase peptide synthesis was carried out by using Boc strategy. After the full sequence was completed on the solid support, we removed the N-terminal Boc group to minimize side reactions during HF cleavage. The resin was then dried under high vacuum for 4 h prior to the final cleavage by HF with 10% (v/v) of anisole. The crude thioester peptide was purified by HPLC to give the pure product in 43% yield. ESI-MS: 1982 Da. (the peptide mass was reconstructed from the experimental mass-to-charge (m/z) ratios from all of the observed protonation states of the peptide).

Example 34

Synthesis of Glycopeptide Thioester $Asp^1$-$Asn^{36}$

The synthesis was based on the procedure published by Wang et al. in *Int. J. Pept. Res. Therap.* 2005, 11, 117-123, which is incorporated herein by reference. The synthesis started with Rink amide resin. After removing Fmoc group by treatment with 20% piperidine (in DMF) for 20 min (×2), the resin was loaded with Fmoc-Asp-OAllyl (4 equiv) by mixing together with the coupling solution containing HBTU (4 equiv) and DIEA (10 equiv) in DMF for 2 h. Afterwards, the resin was washed with DMF (4 mL×4), followed by acetylation of free amines on the resin with $Ac_2O$/DIEA/DMF (1:2: 17) for 20 min. Afterwards, the resin was washed with DMF (4 mL×4), DCM (4 mL×4), and DMF (4 mL×4). Fmoc-SPPS was performed using HBTU/DIEA coupling condition. To couple the glycosylated amino acid, 2 equivalents of building block 16 was used in the synthesis, and the coupling time was elongated to 1 day. Once the full sequence of the glycopeptide was completed on the resin, the allyl group was removed by treating with $Pd(PPh_3)_4$ (25 mg/0.1 mmol resin) and $PhSiH_3$ (10 equiv) in DCM for 30 min (×2). After washing with DCM (4 mL×4), DMF (4 m×4), and then DCM (4 mL×4), we transformed the free acid to thioester by mixing the resin with the reaction solution containing ethyl 3-mercaptopropionate (24 equiv), DIEA (37.5 equiv), anhydrous HOBt (30 equiv), DIC (30 equiv) and DCM/DMF (1/4) for 6 h (×2). Afterwards, the resin was washed with DCM (4 mL×4), DMF (4 m×4), and then DCM (4 mL×4). The glycopeptide was cleaved from the resin with concomitant full deprotection by treatment with $TFA/H_2O$/thioanisole/TES (17/1/1/1). The crude product was subjected to HPLC purification to give the pure product in 9% yield. ESI-MS: 3977 Da. (the peptide mass was reconstructed from the experimental mass-to-charge (m/z) ratios from all of the observed protonation states of the peptide)

Example 35

General Procedure for Sugar-Assisted Ligation (SAL)

The ligation of unprotected peptide segments was performed as follows: Prior to the reaction, the ligation solution (6 M Gn.HCl, 0.2 M phosphate buffer, pH 8.5) was degassed for 10 min. Subsequently, glycopeptide and thioester peptide were dissolved in the ligation solution under Ar. The reaction was performed at 37° C. and was vortexed periodically to equilibrate the reaction mixture. Before HPLC or LC/MS analysis, TCEP (60 mM) or 10% (v/v) of 2-mercaptoethanol was added to reduce any formed disulfide bonds.

Example 36

General Procedure for Desulfurization

Desulfurization reactions were performed at room temperature in 6 M Gn.HCl, 0.2 M phosphate buffer, pH 5.8 containing 15 mM TCEP. The buffer was degassed by bubbling Ar through the solution for 10 min prior to use. Following the addition of $Pd/Al_2O_3$ (15 times of the weight of glycopeptide), the reaction mixture was kept under $H_2$ using $H_2$ balloon. The desulfurization reaction was monitored by analytical HPLC chromatography and LC/MS. Once the reaction was complete, $Pd/Al_2O_3$ was spun down by centrifuge, and the supernatant was collected for HPLC purification.

Example 37

Removing Acm Group from Diptericin Glycopeptide Segment $Cys(Acm)^{37}$-$Phe^{82}$ $Cys(Acm)^{37}$-$Phe^{82}$ (3 mg) was dissolved in 1 mL of 10% AcOH (pH 4.0) containing 30 equivalents of $Hg(OAc)_2$. The reaction mixture was mixed well and left to sit at room temperature for 1 h. Once the reaction was done, 120 equivalents of DTT were added and the mixture was allowed to react for 12 h to precipitate all $Hg(OAc)_2$. The black precipitate was spun down afterwards, and the supernatant was collected for HPLC purification.

Example 38

Native Chemical Ligation (NCL) of Diptericin Glycopeptide $Cys^{37}$-$Phe^{82}$ and Diptericin Glycopeptide Thioester $Asp^1$-$Asn^{36}$ The ligation of glycopeptide segment $Cys^{37}$-$Phe^{82}$ (2.9 mM) and glycopeptide thioester segment $Asp^1$-$Asn^{36}$ (4.4 mM) was carried out in a solution of 6M Gn.HCl, 200 mM phosphate buffer, pH 7.9 containing 2% (v/v) of thiophenol and 2% (v/v) benzylmercaptan at 37° C. After 16 h, we observed that the ligation reaction was complete and the ligation product was confirmed by ESI-MS. After HPLC purification, the pure product was obtained in 47%.

Example 39

Synthesis of 3-O-mercaptoacetyl serine reagent 35

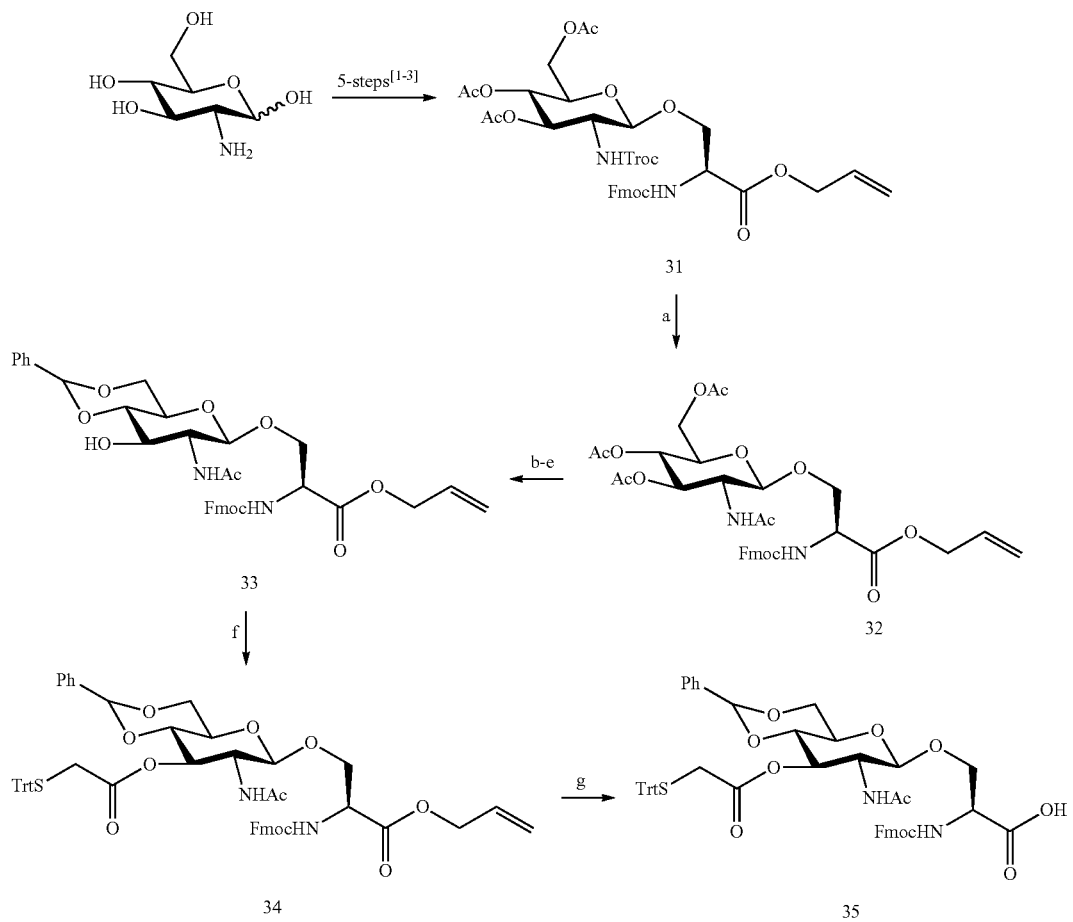

Synthesis of 3-O-Tritylmercaptoacetyl Serine Reagent 35 from (D)-Glucosamine a) Ac$_2$O, AcOH, Zn dust, 91%; b) Pd(PPh$_3$)$_4$, NMA, THF; c) NaOMe, MeOH, pH 9; d) allyl bromide, DIEA, DMF; e) benzaldehyde dimethyl acetal, p-TsOH, MeCN, 51% from 32; f) TrtSCH$_2$COOH, DIC, DMAP, CH$_2$Cl$_2$, 0° C., 91%; g) Pd(PPh$_3$)$_4$, NMA, THF, 91%. AcOH=acetic acid, NMA=N-methylaniline, DIEA=N,N-diisopropylethylamine, p-TsOH=p-toluene-4-sulfonic acid, Troc=2,2,2-trichloroethyl carbamate, Trt=trityl, DIC=N,N'-Diisopropylcarbodiimide, DMAP=4-dimethylaminopyridine.

(3S,4R,5S,6R)-6-((R)-2-(((9H-fluoren-9-yl)methoxy)carbonylamino)-3-(allyloxy)-3-oxopropoxy)-5-acetamido-2-(acetoxymethyl)tetrahydro-2H-pyran-3,4-diyl diacetate 32

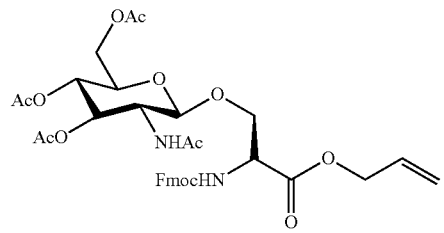

Troc protected glycosyl amino acid 31 (1.07 g, 1.29 mmol) was dissolved in acetic anhydride (16 ml) and the reaction cooled to 0° C. Pre-activated Zn dust [5 g, activated by washing with 1 M HCl (100 ml), water (2×100 ml), diethyl ether (2×100 ml)] was added followed by acetic acid (4.8 ml) and the reaction stirred at rt for 90 min. The reaction was filtered through a plug of celite, washed with dichloromethane and the solvent removed in vacuo. Purification by column chromatography (eluent: 3:1 v/v ethyl acetate/hexane) gave the desired product 32 as a white solid (0.82 g, 91%).

R$_f$(3:1 v/v ethyl acetate/hexane)=0.23; $^1$H- and $^{13}$C-NMR spectroscopic data was consistent to that reported in the literature[23]; HRMS (ESI-TOF) calcd for C$_{35}$H$_{40}$N$_2$O$_{13}$ [M+H]$^+$ 697.2603. Found: 697.2602.

(2R)-allyl 2-(((9H-fluoren-9-yl)methoxy)carbonylamino)-3-((6R,7S,8R,8aS)-7-acetamido-8-hydroxy-2-phenylhexahydropyrano[3,2-d][1,3]dioxin-6-yloxy)propanoate 33

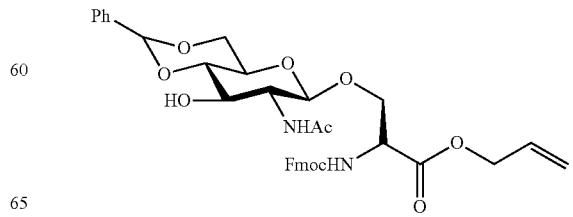

Glycosyl amino acid 32 (1.83 g, 2.63 mmol) was suspended in THF (37 ml). N-methylaniline (2.86 ml, 26.3 mmol) and Pd(PPh$_3$)$_4$ (303 mg, 0.26 mmol) were added and the reaction stirred at rt for 30 min. The solvent was removed in vacuo and the product purified by column chromatography (eluent: 9:1 v/v dichloromethane/methanol+1% AcOH) to give the acid as a cream solid [1.7 g, 95%, R$_F$ (9:1 v/v dichloromethane/methanol)=0.07]. The resulting acid was dissolved in dry methanol (55 ml) and a solution of sodium methoxide in methanol (0.5 M solution) added until the pH reached 9.0. The reaction was stirred at rt for 2 h before neutralizing by the addition of dowex 50H$^+$ resin. The reaction was filtered and the solvent removed in vacuo to give the desired triol which was used in the next step without further purification. The triol was dissolved in DMF (16 ml) and cooled to 0° C. DIEA (0.90 ml, 5.18 mmol) and allyl bromide (0.45 ml, 5.18 mmol) were added dropwise and the reaction stirred at rt for 6 h. The solvent was removed in vacuo and the product purified by column chromatography (eluent: 9:1 v/v dichloromethane/methanol) to give the allyl-protected compound as a white solid (0.77 g). The resulting triol (0.77 g, 1.35 mmol) was dissolved in MeCN (33 ml). Benzaldehyde dimethyl acetal (0.41 ml, 2.70 mmol) and p-toluenesulfonic acid (26 mg, 0.13 mmol) were added and the reaction stirred at rt for 3 h. The solvent was removed in vacuo and the product purified by column chromatography (eluent: 4:1 v/v ethyl acetate/hexane) to give the desired alcohol 33 as a white solid (0.87 g, 98% and 51% from 32).

$^1$H NMR (CDCl$_3$, 600 MHz) δ 7.73 (d, J=7.8 Hz, 2H), 7.61 (dd, J=6.8, 6.9 Hz, 2H), 7.45 (d, J=5.4 Hz, 2H), 7.41 (m, 2H), 7.36 (m, 2H), 7.33-7.26 (m, 3H), 5.85 (m, 1H), 5.50 (s, 1H), 5.30 (d, J=16.8 Hz, 1H), 5.20 (d, J=10.8 Hz, 1H), 4.62 (br. s, 1H), 4.55 (d, J=7.8 Hz, 1H), 4.45 (m, 2H), 4.30 (m, 2H), 4.25 (m, 1H), 4.18 (m, 1H), 3.85-3.77 (m, 2H), 3.69 (m, 1H), 3.58 (m, 1H), 3.46 (m, 1H), 3.39 (m, 1H), 1.90 (s, 3H); $^{13}$C NMR (CDCl$_3$, 150 MHz) δ 172.6, 169.5, 156.5, 143.3, 140.9, 136.7, 131.1, 128.8, 127.8, 127.4, 126.7, 125.9, 124.6, 119.5, 118.0, 101.5, 101.0, 81.1, 70.6, 68.5, 68.1, 66.7, 66.0, 65.8, 56.5, 54.0, 46.7, 22.3; HRMS (ESI-TOF) calcd for C$_{36}$H$_{38}$N$_2$O$_{10}$ [M+H]$^+$659.2599. Found: 659.2597.

(2R)-allyl 2-(((9H-fluoren-9-yl)methoxy)carbonylamino)-3-((6R,7S,8R,8aS)-7-acetamido-2-phenyl-8-(2-(tritylthio)acetoxy)hexahydropyrano[3,2-d][1,3]dioxin-6-yloxy)propanoate 34

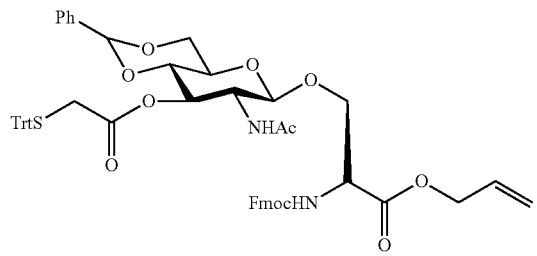

Alcohol 33 (142 mg, 0.22 mmol) was dissolved in dry dichloromethane (7.5 ml). S-Trityl-mercaptoacetic acid (110 mg, 0.32 mmol) was added and the reaction cooled to 0° C. DIC (50 µl, 0.32 mmol) and DMAP (1.3 mg, 0.01 mmol) was added and the reaction stirred at 0° C. for 15 min. The solvent was removed in vacuo and the product purified by column chromatography (eluent: 2:1 hexane/ethyl acaetate—1:1 v/v hexane/ethyl acetate) to afford 34 as a white solid (190 mg, 91%).

R$_f$(1:1 v/v hexane/ethyl acetate)=0.57; $^1$H NMR (CDCl$_3$, 600 MHz) δ 7.87 (dd, J=Hz, 2H), 7.74 (dd, J=Hz 2H), 7.54-7.26 (m, 24H), 5.95 (m, 1H), 5.82 (d, J=10.2, 1H), 5.68 (d, J=10.8 Hz, 1H), 5.56 (s, 1H), 5.41 (dd, J=1.2, 20.4 Hz, 1H), 5.34-5.29 (m, 2H), 4.74 (d, J=6.6 Hz, 2H), 4.56 (m, 3H), 4.51 (d, J=10.8 Hz, 1H), 4.39 (dd, J=6.0, 12.6 Hz, 1H), 4.33-4.26 (m, 2H), 4.00 (dd, J=10.2, 21.0 Hz, 1H), 3.80 (m, 2H), 3.69 (m, 1H), 3.55 (m, 1H), 3.08 (d, J=16.2 Hz, 1H), 2.86 (d, J=16.2 Hz, 1H), 1.89 (s, 3H); $^1$H NMR (CDCl$_3$, 600 MHz) δ 170.5, 170.0, 169.4, 156.0, 143.9, 143.7, 141.4, 136.7, 131.5, 129.5, 128.2, 128.1, 127.8, 127.2, 127.0, 126.1, 125.2, 120.0, 119.4, 118.5, 102.0, 101.3, 78.3, 72.0, 69.1, 68.4, 67.3, 66.6, 66.3, 66.2, 54.4, 54.1, 47.3, 34.6, 23.0; HRMS (ESI-TOF) calcd for C$_{57}$H$_{54}$N$_2$O$_{11}$S [M+H]$^+$975.3521. Found: 935.3526.

(2R)-2-(((9H-fluoren-9-yl)methoxy)carbonylamino)-3-((6R,7S,8R,8aS)-7-acetamido-2-phenyl-8-(2-(tritylthio)acetoxy)hexahydropyrano[3,2-d][1,3]dioxin-6-yloxy)propanoic acid 35

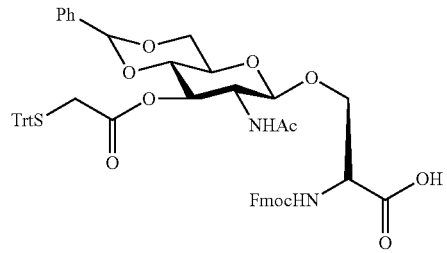

Allyl protected glycosyl amino acid 34 (135 mg, 0.14 mmol) was suspended in THF (6 ml). N-methylaniline (0.15 ml, 1.38 mmol) and Pd(PPh$_3$)$_4$ (16 mg, 0.01 mmol) were added and the reaction stirred at rt for 20 min. The solvent was removed in vacuo and the product purified by column chromatography (eluent: 95:5 v/v dichloromethane/methanol—9:1 v/v dichloromethane/methanol) to give the desired acid 35 as a pale yellow solid (123 mg, 95%).

R$_f$ (95:5 v/v dichloromethane/methanol)=0.26; $^1$H-NMR (1:1 v/v CDCl$_3$/MeOD, 600 MHz): δ 7.73 (d, J=6.6 Hz, 2H), 7.59 (d, J=7.2 Hz 2H), 7.39 (d, J=6.6 Hz 2H), 7.35 (m, 2H), 7.30-7.13 (m, 20H), 5.45 (br. s, 1H), 5.17 (d, J=10.2 Hz, 1H), 4.50 (d, J=7.8 Hz, 1H), 4.42 (dd, J=6.6, 10.2 Hz, 1H), 4.36 (dd, J=6.6, 10.2 Hz, 1H), 4.26 (dd, J=4.8, 10.2 Hz, 1H), 4.22 (br. s, 1H), 4.15 (m, 2H), 3.88 (m, 1H), 3.79 (d, J=8.4 Hz, 1H), 3.68 (m, 1H), 3.59 (m, 1H), 3.44 (m, 1H), 2.90 (d, J=13.8 Hz, 1H), 2.86 (d, J=13.8 Hz, 1H), 1.56 (s, 3H); $^{13}$C-NMR (CDCl$_3$, 150 MHz) δ 172.0, 169.5, 169.0, 156.2, 143.4, 143.3, 140.8, 136.3, 128.9, 128.5, 127.5, 127.4, 127.2, 126.5, 126.4, 125.6, 124.4, 119.3, 101.3, 100.8, 78.2, 71.6, 69.3, 67.8, 66.7, 66.1, 65.6, 53.5, 46.6, 34.0, 29.0, 21.8; LC-MS R$_t$=10.5 min, MH$^+$=935.4; HRMS (ESI-TOF) calcd for C$_{54}$H$_{50}$N$_2$O$_{11}$S [M+H]$^+$935.3208. Found: 935.3211.

Example 40

Solid Phase Peptide Synthesis of an 3-O-Mercaptoacetyl-2-acetamidoglucosyl

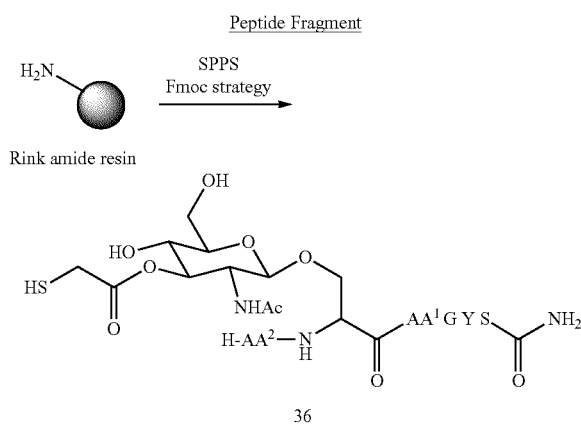

36

(X-Ser-X-Gly-Tyr-Ser corresponds to SEQ ID NO:82 which represents the unmodified amino acids.)

General Procedures

Analytical HPLC was run on a Hitachi (D-7000 HPLC system) instrument using an analytical column (Grace Vydac "Protein &Peptide C18", 150×4.6 mm, 10 µm particle size, flow rate 1.5 ml/min). Semi preparative HPLC was run on a Hitachi (D-7000 HPLC system) instrument using a semi preparative column (Grace Vydac "Protein & Peptide C18", 250×10 mm, 10-15 µm particle size, flow rate 4 mL/min). Preparative HPLC was run on a Hitachi (D-7000 HPLC system) instrument using a preparative Column (Grace Vydac "Protein & Peptide C18", 250×22 mm, 10-15 µm particle size, flow rate 8 mL/min). Detection of the signal was achieved with a photodiode array detector at a wavelength of λ=280 nm. Eluents A (0.1% TFA in water) and B (0.1% TFA in acetonitrile) were used in a linear gradient at 50° C. Gradient A: 0% B→80% B in 30 min.

Materials

Water was taken from a Milli-Q ultra pure water purification system (Millipore corp.). DMF was purchased in biotech grade. Commercial regents were purchased from Sigma-Aldrich or Acros Organics and were used without further purification. Tetrahydrofuran (THF) was distilled over sodium/benzophenone and dichloromethane (CH$_2$Cl$_2$) was distilled over calcium chloride. Other anhydrous-grade solvents were purchased from Sigma-Aldrich and used directly. Molecular sieves (AW 300) were freshly ground and flame-dried directly prior to glycosylation experiments. Analytical thin-layer chromatography (TLC) was performed using silica gel 60 F$_{254}$ glass plates. Compound spots were visualized by UV light (254 nm) and by staining with acidic ceric ammonium molybdate. Flash chromatography was performed on silica gel 60 Geduran (35-75 µm, EMD Science). Resins, protected amino acids and PyBOP were purchased from Novabiochem. Deuterated solvents were purchased from Cambridge Isotope Laboratories Inc.

NMR Spectroscopy $^1$H-NMR and $^{13}$C-NMR were recorded on a Bruker DRX-600 spectrometer equipped with a CryoProbe operating at 600 MHz and 150 MHz respectively. Coupling constants (J) are reported where possible in Hertz (Hz), and chemical shifts are reported in parts per million (ppm) relative to tetramethylsilane (TMS, 0.00 ppm).

Mass Spectrometry

MALDI-TOF mass spectra were measured on a Voyager-DE Pro biospectrometry workstation of PerSeptive Biosystems. A solution of 10 mg/ml α-cyano-4-hydroxy cinnamic acid containing 0.1% TFA was used for generating the probe-matrix mixture.

High resolution mass spectrometra were measured on an Agilent 6210 Time of Flight mass spectrometer.

Peptide Synthesis

Solid-phase chemistry was carried out in syringes, equipped with teflon filters, purchased from Torviq.

Preloading of 3-(Tritylthio) Propanoic Acid onto the MBHA-Linker:

Resin loadings were aimed at approximately 300 µmol/g by adding the resin in excess. First, the resin was washed (5×DCM, 3 min 5% DIPEA/DCM, 5×DCM, 5×DMF). For preactivation of the 3-(tritylthio) propanoic acid, PyBOP (1 eq.) was added to a 0.1 M solution of the 3-(tritylthio) propanoic acid in DMF containing 2 eq. NMM. After 5 min of preactivation, the mixture was added to the resin. After 2 h the resin was washed (5×DMF, 5×DCM, 3 min 5% DIPEA/DCM, 5×DCM, 5×DMF). For capping the resin was treated with acetic anhydride/pyridine (1:9) (2×10 min), washed (5×DMF, 10×DCM) and finally dried in vacuo.

Solid-Phase Synthesis According to Boc-Strategy:

Boc. Cleavage: After treatment with 5% m-Cresol/TFA (2×4 min) the resin was washed with DCM (8×) and with DMF (5×). Coupling: After preactivation of 4 eq. protected amino acid (final concentration 0.1 M in DMF) for 5 min using 4 eq. PyBOP and 8 eq. NMM, the solution was added to the resin. After 30 min, the resin was washed with DMF (5×), DCM (5×) and DMF (5×). Capping: Acetic anhydride/pyridine (1:9) was added to the resin. After 5 min the resin was washed with DMF (5×) and DCM (5×). Terminal capping: Acetic anhydride/pyridine (1:9) was added to the resin. After 10 min the resin was washed with DMF (5×) and DCM (8×). Cleavage: A mixture of TFMSA/TFA/thioanisol (2:8:1) was added to the resin. After 2 h, the resin was washed with TFA (4×) Work-up: The combined solutions were concentrated in vacuo. The residue was dissolved in water, purified by preparative HPLC and analyzed by MALDI-TOF/MS (matrix: α-Cyano-4-hydroxycinnamic acid).

Preloading of the Rink Amide Resin:

First, the resin was washed (5×DCM, 5×DMF), followed by removal of the Fmoc group by treating it with 10% piperidine/DMF (2×5 min) and another washing step (5×DMF, 5×DCM, 5×DMF). For preactivation of the first protected amino acid, 4 eq. of PyBOP and 8 eq. of NMM were added to a solution of the building block (0.1 M) in DMF. After 5 min of preactivation, the mixture was added to the resin. After 2 h the resin was washed (5×DMF, 5×DCM, 5×DMF), capped with acetic anhydride/pyridine (1:9) (2×5 min) and washed (5×DMF, 5×DCM, 5×DMF).

Glycopeptide Solid-Phase Synthesis According to the Fmoc-Strategy:

Fmoc Cleavage: After treatment with 10% piperidine/DMF (2×5 min) the resin was washed (5×DMF, 5×DCM, 5×DMF). Coupling: After preactivation of 4 eq. protected amino acid (final concentration 0.1 M in DMF) for 5 min using 4 eq. PyBOP and 8 eq. NMM, the solution was added to the resin. After 30 min, the resin was washed with DMF (5×), DCM (5×) and DMF (5×). Capping: Acetic anhydride/pyridine (1:9) was added to the resin. After 5 min the resin was washed with DMF (5×), DCM (5×) and DMF (5×). Coupling of the sugar containing monomer: After preactivation of 1 eq. of building block (final concentration 0.1 M in DMF) for 5 min using 1 eq. PyBOP and 2 eq. NMM, the solution was added to the resin. After 6 h, the resin was washed with DMF (5×), DCM (5×) and DMF (5×). Cleavage: A mixture of TFA, thioanisole, triisopropylsilane and water (17:1:1:1) was added. After 2 h, the resin was washed with TFA (4×4 mL) Work-up: The combined solutions were concentrated in vacuo. The residue was dissolved in water, purified by preparative HPLC and analyzed by MALDI-TOF/MS (matrix: α-Cyano-4-hydroxycinnamic acid).

Glycopeptides Prepared by Solid Phase Peptide Synthesis (SPPS)

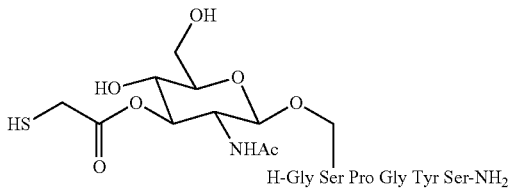
H-Gly Ser Pro Gly Tyr Ser-NH$_2$ (SEQ ID NO:12 corresponds to the unmodified amino acids).
Starting from 100 μmol Fmoc-Ser-Rink Amide-resin, the linear assembly was performed following the Fmoc-strategy. Yield: 36 mg (43 μmol, 43%). ESI-TOF high-acc. (m/z): 843.3181 ([M+H]$^+$, theor. 843.3189). HPLC: $t_R$: 6.6 min (Gradient A); C$_{34}$H$_{50}$N$_8$O$_{15}$S (842.3116).

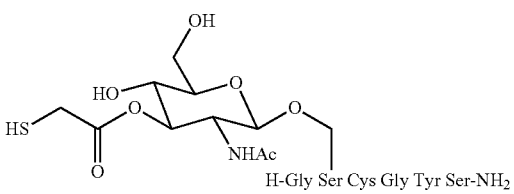
H-Gly Ser Cys Gly Tyr Ser-NH$_2$ (SEQ ID NO:13 corresponds to the unmodified amino acids).
Starting from 100 μmol Fmoc-Ser-Rink Amide-resin, the linear assembly was performed following the Fmoc-strategy. Yield: 35 mg (41 μmol, 41%). ESI-TOF high-acc. (m/z): 849.2737 ([M+H]$^+$, theor. 849.2753). HPLC: $t_R$: 5.6 min (Gradient A); C$_{32}$H$_{48}$N$_8$O$_{15}$S$_2$ (848.2680).

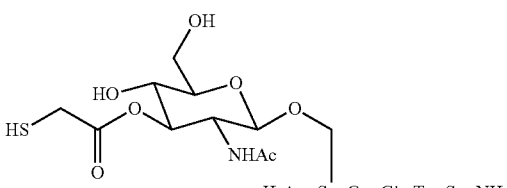
H-Asp Ser Cys Gly Tyr Ser-NH$_2$ (SEQ ID NO:14 corresponds to the unmodified amino acids).
Starting from 66.5 μmol Fmoc-Ser-Rink Amide-resin, the linear assembly was performed following the Fmoc-strategy. Yield: 21.5 mg (24 μmol, 36%). ESI-TOF high-acc. (m/z): 907.2796 ([M+H]$^+$, theor. 907.2808). HPLC: $t_R$: 5.7 min (Gradient A); C$_{34}$H$_{50}$N$_8$O$_{17}$S$_2$ (906.2735).

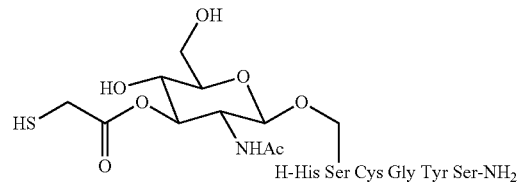
H-His Ser Cys Gly Tyr Ser-NH$_2$

SEQ ID NO:15 corresponds to the unmodified amino acids).
Starting from 66.5 μmol Fmoc-Ser-Rink Amide-resin, the linear assembly was performed following the Fmoc-strategy. Yield: 25 mg (27 μmol, 41%). ESI-TOF high-acc. (m/z): 929.3123 ([M+H]$^+$, theor. 929.3128). HPLC: $t_R$: 5.9 min (Gradient A); C$_{36}$H$_{52}$N$_{10}$O$_{15}$S$_2$ (928.3055).

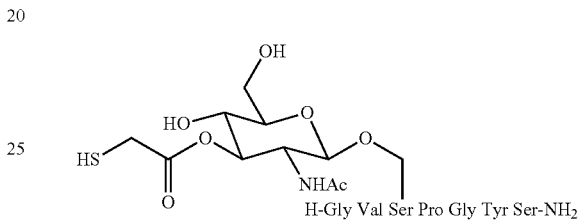
H-Gly Val Ser Pro Gly Tyr Ser-NH$_2$ (SEQ ID NO:16 corresponds to the unmodified amino acids).
Starting from 100 μmol Fmoc-Ser-Rink Amide-resin, the linear assembly was performed following the Fmoc-strategy. Yield: 20 mg (21 μmol, 21%). ESI-TOF high-acc. (m/z): 942.3860 ([M+H]$^+$, theor. 942.3873). HPLC: $t_R$: 6.7 min (Gradient A); C$_{39}$H$_{59}$N$_9$O$_{16}$S (941.3800).

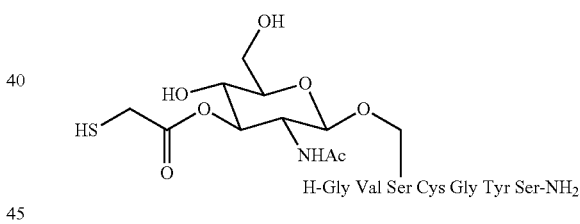
H-Gly Val Ser Cys Gly Tyr Ser-NH$_2$ (SEQ ID NO:17 corresponds to the unmodified amino acids).
Starting from 66.5 μmol Fmoc-Ser-Rink Amide-resin, the linear assembly was performed following the Fmoc-strategy. Yield: 11 mg (12 μmol, 18%). ESI-TOF high-acc. (m/z): 948.3421 ([M+H]$^+$, theor. 948.3437). HPLC: $t_R$: 6.6 min (Gradient A); C$_{37}$H$_{57}$N$_9$O$_{16}$S$_2$ (947.3365).

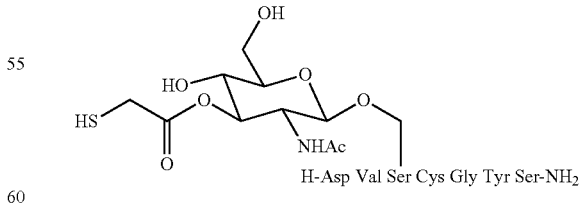
H-Asp Val Ser Cys Gly Tyr Ser-NH$_2$ (SEQ ID NO:18 corresponds to the unmodified amino acids).
Starting from 66.5 μmol Fmoc-Ser-Rink Amide-resin, the linear assembly was performed
following the Fmoc-strategy. Yield: 12 mg (12 μmol, 18%). ESI-TOF high-acc. (m/z): 1006.3484 ([M+H]$^+$, theor. 1006.3492). HPLC: $t_R$: 6.6 min (Gradient A); C$_{39}$H$_{59}$N$_9$O$_{18}$S$_2$ (1005.3419).

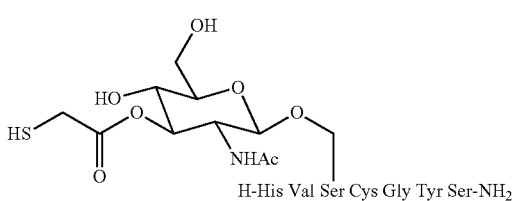

H-His Val Ser Cys Gly Tyr Ser-NH$_2$ (SEQ ID NO:19 corresponds to the unmodified amino acids).

Starting from 66.5 μmol Fmoc-Ser-Rink Amide-resin, the linear assembly was performed following the Fmoc-strategy. Yield: 10 mg (10 μmol, 14%). ESI-TOF high-acc. (m/z): 1028.3804 ([M+H]$^+$, theor. 1028.3812). HPLC: $t_R$: 6.5 min (Gradient A); $C_{41}H_{61}N_{11}O_{16}S_2$ (1027.3739).

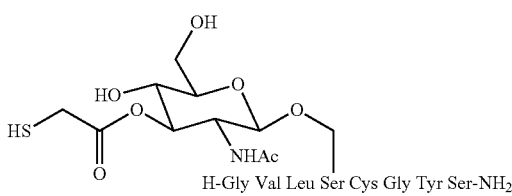

H-Gly Val Leu Ser Cys Gly Tyr Ser-NH$_2$ (SEQ ID NO:20 corresponds to the unmodified amino acids).

Starting from 66.5 μmol Fmoc-Ser-Rink Amide-resin, the linear assembly was performed following the Fmoc-strategy. Yield: 12 mg (11 μmol, 17%). ESI-TOF high-acc. (m/z): 1061.4271 ([M+H]$^+$, theor. 1061.4278). HPLC: $t_R$: 9.0 min (Gradient A); $C_{43}H_{68}N_{10}O_{17}S_2$ (1060.4205).

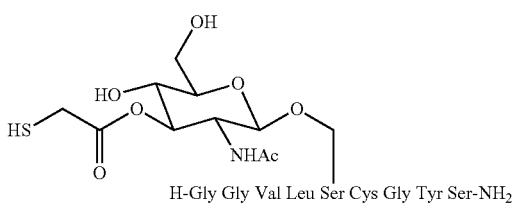

H-Gly Gly Val Leu Ser Cys Gly Tyr Ser-NH$_2$ (SEQ ID NO:21 corresponds to the unmodified amino acids).

Starting from 66.5 μmol Fmoc-Ser-Rink Amide-resin, the linear assembly was performed following the Fmoc-strategy. Yield: 3 mg (3 μmol, 4%). ESI-TOF high-acc. (m/z): 1118.4488 ([M+H]$^+$, theor. 1118.4493). HPLC: $t_R$: 8.8 min (Gradient A); $C_{45}H_{71}N_{11}O_{18}S_2$ (1117.4420).

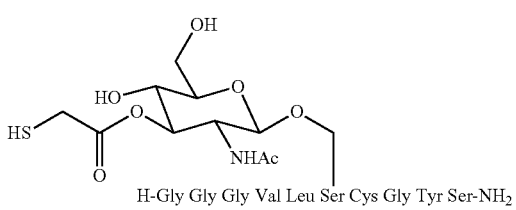

H-Gly Gly Gly Val Leu Ser Cys Gly Tyr Ser-NH$_2$ (SEQ ID NO:22 corresponds to the unmodified amino acids).

Starting from 66.5 μmol Fmoc-Ser-Rink Amide-resin, the linear assembly was performed following the Fmoc-strategy. Yield: 7 mg (6 μmol, 9%). ESI-TOF high-acc. (m/z): 1175.4706 ([M+H]$^+$, theor. 1175.4707). HPLC: $t_R$: 8.4 min (Gradient A); $C_{47}H_{74}N_{12}O_{19}S_2$ (1174.4634).

Peptide Thioesters Prepared by SPPS

Ac-Leu Tyr Arg Ala Gly-S(CH$_2$)$_2$CONH$_2$ (SEQ ID NO:23 corresponds to the unmodified amino acids).

Starting from 100 μmol MBHA-resin preloaded with 3-(tritylthio)propanoic acid, the linear assembly was performed following the Boc-strategy. Yield: 50.6 mg (72 μmol, 72%). ESI-TOF high-acc. (m/z): 708.3499 ([M+H]$^+$, theor. 708.3497). HPLC: $t_R$: 8.4 min (Gradient A); $C_{31}H_{49}N_9O_8S$ (707.3425).

Ac-Leu Tyr Arg Ala Ala-S(CH$_2$)$_2$CONH$_2$ (SEQ ID NO:24 corresponds to the unmodified amino acids).

Starting from 100 μmol MBHA-resin preloaded with 3-(tritylthio)propanoic acid, the linear assembly was performed following the Boc-strategy. Yield: 39 mg (52 μmol, 52%). ESI-TOF high-acc. (m/z): 722.3644 ([M+H]$^+$, theor. 722.3654). HPLC: $t_R$: 8.8 min (Gradient A); $C_{32}H_{51}N_9O_8S$ (721.3581).

Ac-Leu Tyr Arg Ala Tyr-S(CH$_2$)$_2$CONH$_2$ (SEQ ID NO:25 corresponds to the unmodified amino acids).

Starting from 100 μmol MBHA-resin preloaded with 3-(tritylthio)propanoic acid, the linear assembly was performed following the Boc-strategy. Yield: 33.3 mg (41 μmol, 41%). ESI-TOF high-acc. (m/z): 814.3901 ([M+H]$^+$, theor. 814.3916). HPLC: $t_R$: 9.3 min (Gradient A); $C_{38}H_{55}N_9O_9S$ (813.3843).

Ac-Leu Tyr Arg Ala His-S(CH$_2$)$_2$CONH$_2$ (SEQ ID NO:26 corresponds to the unmodified amino acids).

Starting from 100 μmol MBHA-resin preloaded with 3-(tritylthio)propanoic acid, the linear assembly was performed following the Boc-strategy. Yield: 31 mg (39 μmol, 39%). ESI-TOF high-acc. (m/z): 788.3863 ([M+H]$^+$, theor. 788.3872). HPLC: $t_R$: 8.0 min (Gradient A); $C_{35}H_{53}N_{11}O_8S$ (787.3799).

Ac-Leu Tyr Arg Ala Phe-S(CH$_2$)$_2$CONH$_2$ (SEQ ID NO:27 corresponds to the unmodified amino acids).

Starting from 100 μmol MBHA-resin preloaded with 3-(tritylthio)propanoic acid, the linear assembly was performed following the Boc-strategy. Yield: 8.7 mg (11 μmol, 11%). ESI-TOF high-acc. (m/z): 798.3963 ([M+H]$^+$, theor. 798.3967). HPLC: $t_R$: 9.5 min (Gradient A); $C_{38}H_{55}N_9O_8S$ (797.3894).

Peptide Ligation Reactions

Glycopeptides (1.5 equiv, approx. 3 μmol) were dissolved in 150 μl of deoxygenated ligation buffer (4:1 v/v N-methyl-2-pyrrolidinone: 6M guanidine hydrochloride, 1 M HEPES, pH=8.5). This solution was transferred to an Eppendorf tube containing the peptide thioester (approx. 2 μmol). Thiophenol (2% by volume, 3 μl) was added and the reaction mixed gently. The ligation mixture was incubated at 37° C. with gentle mixing every 12 h until the reaction was shown to be complete by LC-MS.

Ligation Products

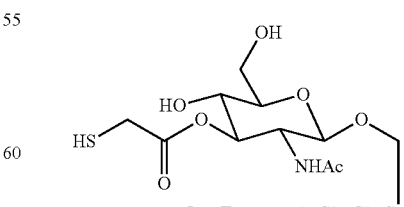

Ac-Leu Tyr Arg Ala Gly-Gly Ser Pro Gly Tyr Ser-NH$_2$ (SEQ ID NO:28 corresponds to the unmodified amino acids). Yield: 69%. MALDI-TOF (m/z): 1446.2 ([M+H]$^+$, theor. 1446.6). HPLC: $t_R$: 8.7 min (Gradient A); $C_{62}H_{92}N_{16}O_{22}S$ (1445.6).

[Structure: sugar moiety attached to peptide]
Ac-Leu Tyr Arg Ala Gly-Gly Ser Pro Gly Tyr Ser-NH$_2$ (SEQ ID NO:28 corresponds to the unmodified amino acids).
Yield: >95%. MALDI-TOF (m/z): 1371.8 ([M+H]$^+$, theor. 1372.5). HPLC: $t_R$: 7.8 min (Gradient A); $C_{60}H_{90}N_{16}O_{21}$ (1371.5).

[Structure: sugar moiety with thiol attached to peptide]
Ac-Leu Tyr Arg Ala Gly-Gly Ser Cys Gly Tyr Ser-NH$_2$ (SEQ ID NO:29 corresponds to the unmodified amino acids).
Yield: 84%. MALDI-TOF (m/z): 1451.7 ([M+H]$^+$, theor. 1452.6). HPLC: $t_R$: 8.7 min (Gradient A); $C_{60}H_{90}N_{16}O_{22}S_2$ (1451.6).

[Structure: sugar moiety attached to peptide]
Ac-Leu Tyr Arg Ala Gly-Gly Ser Cys Gly Tyr Ser-NH$_2$ (SEQ ID NO:29 corresponds to the unmodified amino acids).
Yield: >95%. MALDI-TOF (m/z): 1378.3 ([M+H]$^+$, theor. 1378.5). HPLC: $t_R$: 8.1 min (Gradient A); $C_{58}H_{88}N_{16}O_{21}S$ (1377.5).

[Structure: sugar moiety with thiol attached to peptide]
Ac-Leu Tyr Arg Ala Gly-His Ser Cys Gly Tyr Ser-NH$_2$ (SEQ ID NO:30 corresponds to the unmodified amino acids).
Yield: 28%. MALDI-TOF (m/z): 1533.1 ([M+H]$^+$, theor. 1532.7). HPLC: $t_R$: 8.9 min (Gradient A); $C_{64}H_{94}N_{18}O_{22}S_2$ (1531.7).

[Structure: sugar moiety attached to peptide]
Ac-Leu Tyr Arg Ala Gly-His Ser Cys Gly Tyr Ser-NH$_2$ (SEQ ID NO:30 corresponds to the unmodified amino acids).
Yield: >95%. MALDI-TOF (m/z): 1458.0 ([M+H]$^+$, theor. 1458.6). HPLC: $t_R$: 8.3 min (Gradient A); $C_{62}H_{92}N_{18}O_{21}S$ (1457.6).

[Structure: sugar moiety with thiol attached to peptide]
Ac-Leu Tyr Arg Ala His-His Ser Cys Gly Tyr Ser-NH$_2$ (SEQ ID NO:31 corresponds to the unmodified amino acids).
Yield: 27%. MALDI-TOF (m/z): 1612.4 ([M+H]$^+$, theor. 1612.8). HPLC: $t_R$: 8.1 min (Gradient A); $C_{68}H_{99}N_{20}O_{22}S_2$ (1611.8).

[Structure: sugar moiety attached to peptide]
Ac-Leu Tyr Arg Ala His-His Ser Cys Gly Tyr Ser-NH$_2$ (SEQ ID NO:31 corresponds to the unmodified amino acids).
Yield: >95%. MALDI-TOF (m/z): 1538.0 ([M+H]$^+$, theor. 1538.7). HPLC: $t_R$: 7.6 min (Gradient A); $C_{66}H_{96}N_{20}O_{21}S$ (1537.7).

[Structure: sugar moiety with thiol attached to peptide]
Ac-Leu Tyr Arg Ala Gly-Asp Ser Cys Gly Tyr Ser-NH$_2$ (SEQ ID NO:32 corresponds to the unmodified amino acids).
Yield: 38%. MALDI-TOF (m/z): 1509.3 ([M+H]$^+$, theor. 1510.6). HPLC: $t_R$: 9.3 min (Gradient A); $C_{62}H_{92}N_{16}O_{24}S_2$ (1509.6).

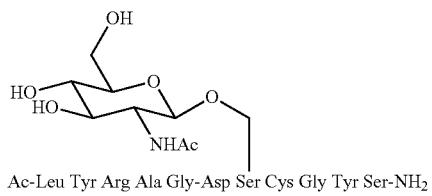

Ac-Leu Tyr Arg Ala Gly-Asp Ser Cys Gly Tyr Ser-NH$_2$ (SEQ ID NO:32 corresponds to the unmodified amino acids).
Yield: >95%. MALDI-TOF (m/z): 1435.9 ([M+H]$^+$, theor. 1436.5). HPLC: t$_R$: 8.2 min (Gradient A); C$_{60}$H$_{90}$N$_{16}$O$_{23}$S (1435.5).

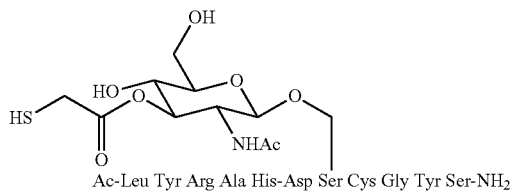

Ac-Leu Tyr Arg Ala His-Asp Ser Cys Gly Tyr Ser-NH$_2$ (SEQ ID NO:33 corresponds to the unmodified amino acids).
Yield: 22%. MALDI-TOF (m/z): 1590.5 ([M+H]$^+$, theor. 1590.7). HPLC: t$_R$: 8.3 min (Gradient A); C$_{66}$H$_{97}$N$_{18}$O$_{24}$S$_2$ (1589.7).

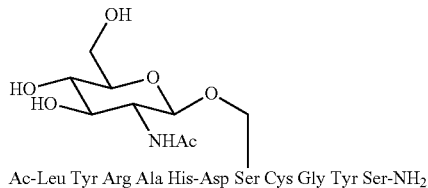

Ac-Leu Tyr Arg Ala His-Asp Ser Cys Gly Tyr Ser-NH$_2$ (SEQ ID NO:33 corresponds to the unmodified amino acids).
Yield: >95%. MALDI-TOF (m/z): 1514.6 ([M+H]$^+$, theor. 1516.6). HPLC: t$_R$: 8.3 min (Gradient A); C$_{64}$H$_{94}$N$_{18}$O$_{23}$S (1515.6).

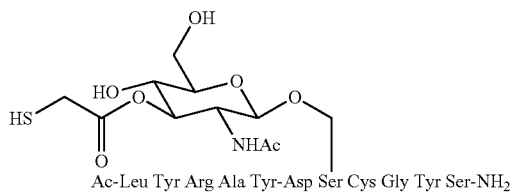

Ac-Leu Tyr Arg Ala Tyr-Asp Ser Cys Gly Tyr Ser-NH$_2$ (SEQ ID NO:34 corresponds to the unmodified amino acids).
Yield: 40%. MALDI-TOF (m/z): 1616.4 ([M+H]$^+$, theor. 1616.7). HPLC: t$_R$: 9.9 min (Gradient A); C$_{69}$H$_{98}$N$_{16}$O$_{25}$S$_2$ (1615.7).

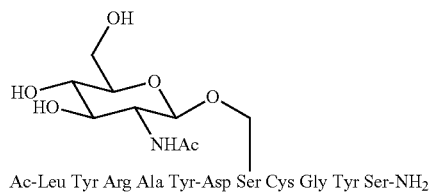

Ac-Leu Tyr Arg Ala Tyr-Asp Ser Cys Gly Tyr Ser-NH$_2$ (SEQ ID NO:34 corresponds to the unmodified amino acids).
Yield: >95%. MALDI-TOF (m/z): 1541.8 ([M+H]$^+$, theor. 1542.6). HPLC: t$_R$: 8.8 min (Gradient A); C$_{67}$H$_{96}$N$_{16}$O$_{24}$S (1541.6).

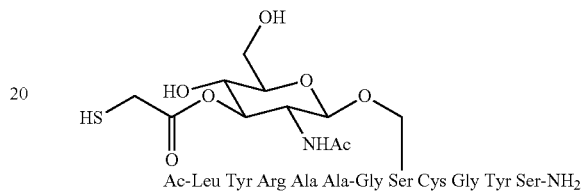

Ac-Leu Tyr Arg Ala Ala-Gly Ser Cys Gly Tyr Ser-NH$_2$ (SEQ ID NO:35 corresponds to the unmodified amino acids).
Yield: 28%. MALDI-TOF (m/z): 1466.2 ([M+H]$^+$, theor. 1466.6). HPLC: t$_R$: 9.8 min (Gradient A); C$_{61}$H$_{92}$N$_{16}$O$_{22}$S$_2$ (1465.6).

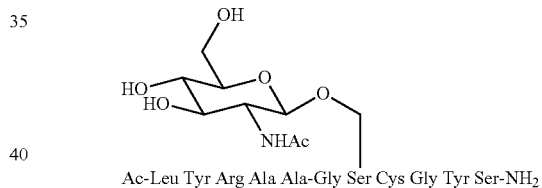

Ac-Leu Tyr Arg Ala Ala-Gly Ser Cys Gly Tyr Ser-NH$_2$ (SEQ ID NO:35 corresponds to the unmodified amino acids).
Yield: >95%. MALDI-TOF (m/z): 1392.5 ([M+H]$^+$, theor. 1392.5). HPLC: t$_R$: 8.6 min (Gradient A); C$_{59}$H$_{90}$N$_{16}$O$_{21}$S (1391.5).

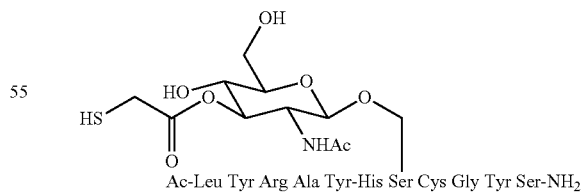

Ac-Leu Tyr Arg Ala Tyr-His Ser Cys Gly Tyr Ser-NH$_2$ (SEQ ID NO:36 corresponds to the unmodified amino acids).
Yield: 32%. MALDI-TOF (m/z): 1637.5 ([M+H]$^+$, theor. 1638.8). HPLC: t$_R$: 9.6 min (Gradient A); C$_{71}$H$_{100}$N$_{18}$O$_{23}$S$_2$ (1637.8).

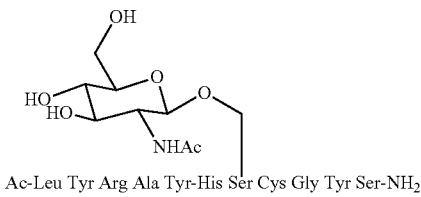 [SMILES: CCOC1OC(CO)C(O)C(O)C1NC(C)=O]

Ac-Leu Tyr Arg Ala Tyr-His Ser Cys Gly Tyr Ser-NH$_2$ (SEQ ID NO:36 corresponds to the unmodified amino acids).
Yield: >95%. MALDI-TOF (m/z): 1564.6 ([M+H]$^+$, theor. 1564.7). HPLC: $t_R$: 8.4 min (Gradient A); C$_{69}$H$_{98}$N$_{18}$O$_{22}$S (1563.7).

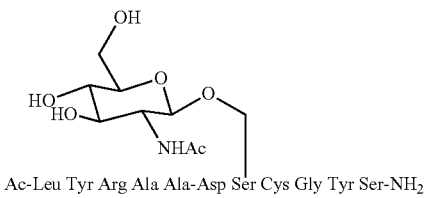

Ac-Leu Tyr Arg Ala Ala-Asp Ser Cys Gly Tyr Ser-NH$_2$ (SEQ ID NO:38 corresponds to the unmodified amino acids).
Yield: >95%. MALDI-TOF (m/z): 1450.8 ([M+H]$^+$, theor. 1450.5). HPLC: $t_R$: 8.2 min (Gradient A); C$_{61}$H$_{92}$N$_{16}$O$_{23}$S (1449.5).

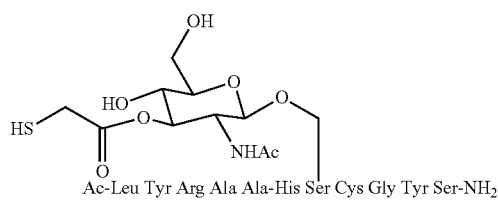 [SMILES: CCOC1OC(CO)C(O)C(OC(=O)CS)C1NC(C)=O]

Ac-Leu Tyr Arg Ala Ala-His Ser Cys Gly Tyr Ser-NH$_2$ (SEQ ID NO:37 corresponds to the unmodified amino acids).
Yield: 40%. MALDI-TOF (m/z): 1548.2 ([M+H]$^+$, theor. 1546.7). HPLC: $t_R$: 9.6 min (Gradient A); C$_{65}$H$_{96}$N$_{18}$O$_{22}$S$_2$ (1545.7).

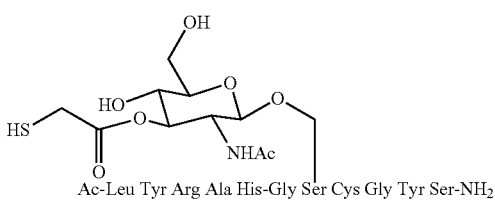

Ac-Leu Tyr Arg Ala His-Gly Ser Cys Gly Tyr Ser-NH$_2$ (SEQ ID NO:39 corresponds to the unmodified amino acids).
Yield: 62%. MALDI-TOF (m/z): 1531.3 ([M+H]$^+$, theor. 1532.7). HPLC: $t_R$: 9.2 min (Gradient A); C$_{64}$H$_{94}$N$_{18}$O$_{22}$S$_2$ (1531.7).

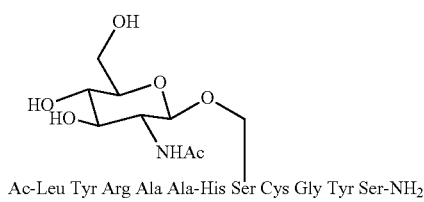 [SMILES: CCOC1OC(CO)C(O)C(O)C1NC(C)=O]

Ac-Leu Tyr Arg Ala Ala-His Ser Cys Gly Tyr Ser-NH$_2$ (SEQ ID NO:37 corresponds to the unmodified amino acids).
Yield: >95%. MALDI-TOF (m/z): 1472.6 ([M+H]$^+$, theor. 1472.6). HPLC: $t_R$: 8.2 min (Gradient A); C$_{63}$H$_{94}$N$_{18}$O$_{21}$S (1471.6).

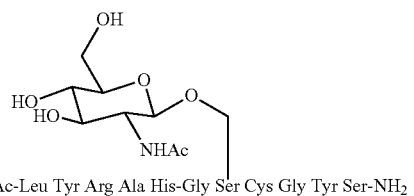

Ac-Leu Tyr Arg Ala His-Gly Ser Cys Gly Tyr Ser-NH$_2$ (SEQ ID NO:39 corresponds to the unmodified amino acids).
Yield: >95%. MALDI-TOF (m/z): 1459.7 ([M+H]$^+$, theor. 1458.6). HPLC: $t_R$: 7.8 min (Gradient A); C$_{62}$H$_{92}$N$_{18}$O$_{21}$S (1457.6).

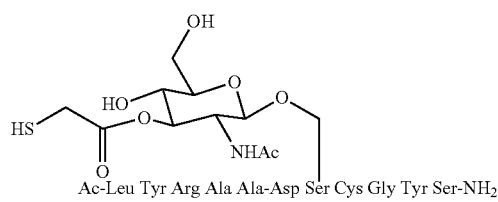 [SMILES: CCOC1OC(CO)C(O)C(OC(=O)CS)C1NC(C)=O]

Ac-Leu Tyr Arg Ala Ala-Asp Ser Cys Gly Tyr Ser-NH$_2$ (SEQ ID NO:38 corresponds to the unmodified amino acids).
Yield: 59%. MALDI-TOF (m/z): 1524.8 ([M+H]$^+$, theor. 1524.7). HPLC: $t_R$: 9.8 min (Gradient A); C$_{63}$H$_{94}$N$_{16}$O$_{24}$S$_2$ (1523.6).

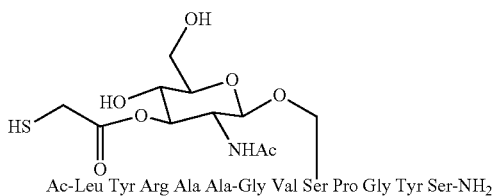

Ac-Leu Tyr Arg Ala Ala-Gly Val Ser Pro Gly Tyr Ser-NH$_2$ (SEQ ID NO:40 corresponds to the unmodified amino acids).
Yield: 65%. MALDI-TOF (m/z): 1559.6 ([M+H]$^+$, theor. 1559.7). HPLC: $t_R$: 9.8 min (Gradient A); C$_{68}$H$_{103}$N$_{17}$O$_{23}$S (1558.7).

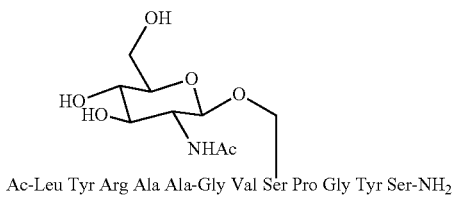

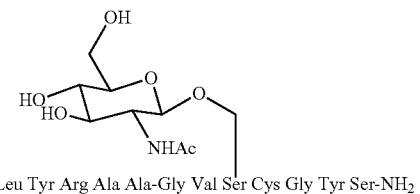 [SMILES: CCOC1OC(CO)C(O)C(O)C1NC(C)=O]

(SEQ ID NO:40 corresponds to the unmodified amino acids).
Yield: >95%. MALDI-TOF (m/z): 1485.2 ([M+H]$^+$, theor. 1485.6). HPLC: $t_R$: 8.9 min (Gradient A); $C_{66}H_{103}N_{17}O_{22}$ (1484.6).

(SEQ ID NO:42 corresponds to the unmodified amino acids).
Yield: >95%. MALDI-TOF (m/z): 1491.7 ([M+H]$^+$, theor. 1491.6). HPLC: $t_R$: 9.0 min (Gradient A); $C_6H_{99}N_{17}O_{22}S$ (1490.6).

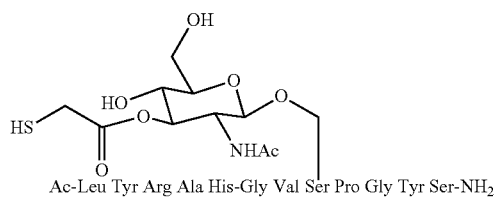 [SMILES: CCOC1OC(CO)C(O)C(OC(=O)CS)C1NC(C)=O]

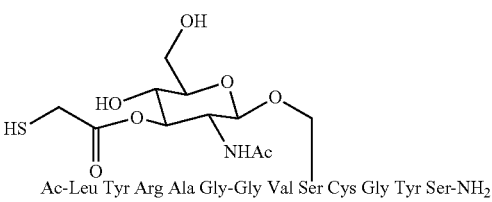 [SMILES: CCOC1OC(CO)C(O)C(OC(=O)CS)C1NC(C)=O]

(SEQ ID NO:43 corresponds to the unmodified amino acids).
Yield: 66%. MALDI-TOF (m/z): 1550.8 ([M+H]$^+$, theor. 1551.7). HPLC: $t_R$: 9.4 min (Gradient A); $C_{65}H_{99}N_{17}O_{23}S_2$ (1550.7).

(SEQ ID NO:41 corresponds to the unmodified amino acids).
Yield: 58%. MALDI-TOF (m/z): 1625.7 ([M+H]$^+$, theor. 1625.8). HPLC: $t_R$: 9.3 min (Gradient A); $C_{71}H_{105}N_{19}O_{23}S$ (1624.8).

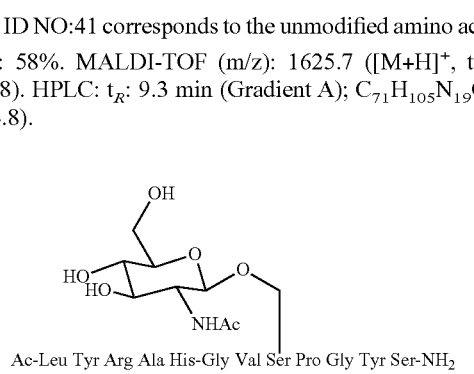

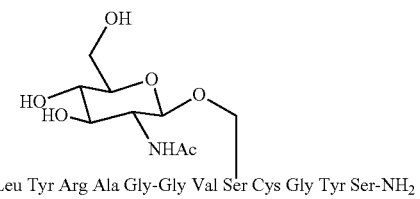

(SEQ ID NO:43 corresponds to the unmodified amino acids).
Yield: >95%. MALDI-TOF (m/z): 1477.3 ([M+H]$^+$, theor. 1477.6). HPLC: $t_R$: 8.4 min (Gradient A); $C_{63}H_{97}N_{17}O_{22}S$ (1476.6).

(SEQ ID NO:41 corresponds to the unmodified amino acids).
Yield: >95%. MALDI-TOF (m/z): 1551.7 ([M+H]$^+$, theor. 1551.7). HPLC: $t_R$: 8.2 min (Gradient A); $C_{69}H_{104}N_{19}O_{22}$ (1550.7).

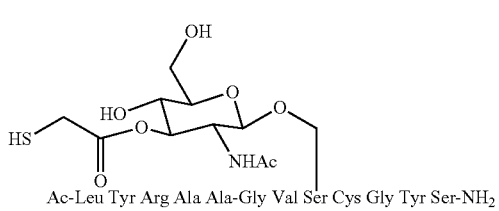

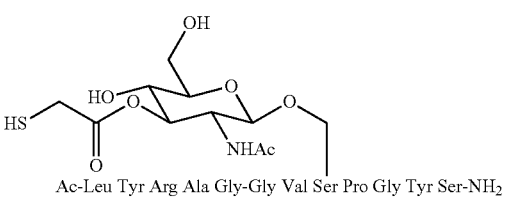

(SEQ ID NO:42 corresponds to the unmodified amino acids).
Yield: 48%. MALDI-TOF (m/z): 1565.4 ([M+H]$^+$, theor. 1565.7). HPLC: $t_R$: 10.0 min (Gradient A); $C_{66}H_{w1}N_{17}O_{23}S_2$ (1564.7).

(SEQ ID NO:44 corresponds to the unmodified amino acids).
Yield: 68%. MALDI-TOF (m/z): 1545.5 ([M+H]$^+$, theor. 1545.7). HPLC: $t_R$: 9.9 min (Gradient A); $C_{67}H_{101}N_{17}O_{23}S$ (1544.7).

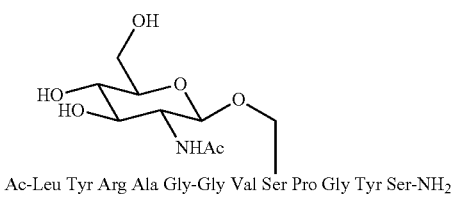

Ac-Leu Tyr Arg Ala Gly-Gly Val Ser Pro Gly Tyr Ser-NH₂

(SEQ ID NO:44 corresponds to the unmodified amino acids).
Yield: >95%. MALDI-TOF (m/z): 1471.7 ([M+H]⁺, theor. 1471.6). HPLC: $t_R$: 8.5 min (Gradient A); $C_{65}H_{99}N_{17}O_{22}$ (1470.6).

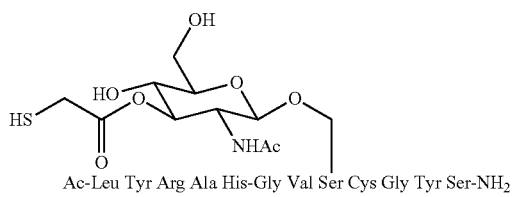

Ac-Leu Tyr Arg Ala His-Gly Val Ser Cys Gly Tyr Ser-NH₂

(SEQ ID NO:45 corresponds to the unmodified amino acids).
Yield: 60%. MALDI-TOF (m/z): 1632.2 ([M+H]⁺, theor. 1631.8). HPLC: $t_R$: 9.3 min (Gradient A); $C_{69}H_{103}N_{19}O_{23}S_2$ (1630.8).

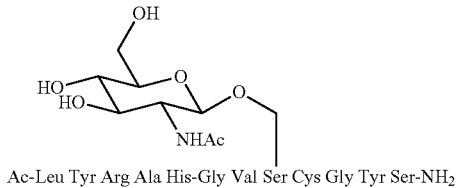

Ac-Leu Tyr Arg Ala His-Gly Val Ser Cys Gly Tyr Ser-NH₂

(SEQ ID NO:45 corresponds to the unmodified amino acids).
Yield: >95%. MALDI-TOF (m/z): 1557.9 ([M+H]⁺, theor. 1557.7). HPLC: $t_R$: 8.3 min (Gradient A); $C_{67}H_{101}N_{19}O_{22}S$ (1556.7).

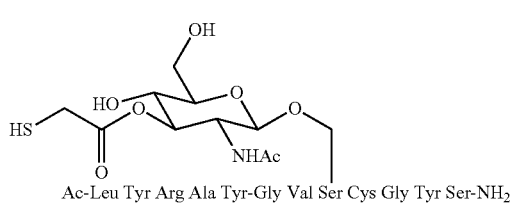

Ac-Leu Tyr Arg Ala Tyr-Gly Val Ser Cys Gly Tyr Ser-NH₂

(SEQ ID NO:46 corresponds to the unmodified amino acids).
Yield: 45%. MALDI-TOF (m/z): 1657.5 ([M+H]⁺, theor. 1657.8). HPLC: $t_R$: 10.6 min (Gradient A); $C_{72}H_{105}N_{17}O_{24}S_2$ (1656.8).

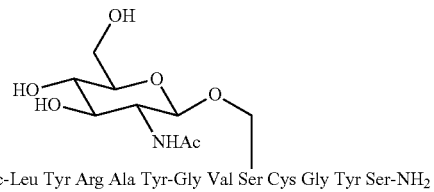

Ac-Leu Tyr Arg Ala Tyr-Gly Val Ser Cys Gly Tyr Ser-NH₂

(SEQ ID NO:46 corresponds to the unmodified amino acids).
Yield: >95%. MALDI-TOF (m/z): 1583.1 ([M+H]⁺, theor. 1583.7). HPLC: $t_R$: 9.6 min (Gradient A); $C_{70}H_{103}N_{17}O_{23}S$ (1582.7).

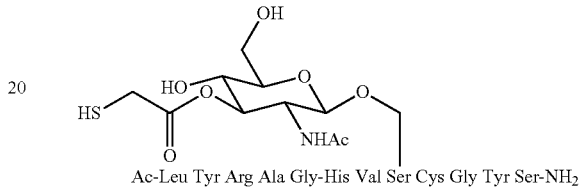

Ac-Leu Tyr Arg Ala Gly-His Val Ser Cys Gly Tyr Ser-NH₂

(SEQ ID NO:47 corresponds to the unmodified amino acids).
Yield: 55%. MALDI-TOF (m/z): 1630.3 ([M+H]⁺, theor. 1631.8). HPLC: $t_R$: 9.0 min (Gradient A); $C_{69}H_{103}N_{19}O_{23}S_2$ (1630.8).

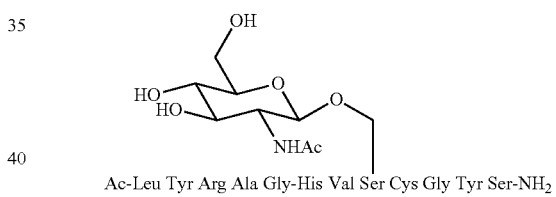

Ac-Leu Tyr Arg Ala Gly-His Val Ser Cys Gly Tyr Ser-NH₂

(SEQ ID NO:47 corresponds to the unmodified amino acids).
Yield: >95%. MALDI-TOF (m/z): 1558.3 ([M+H]⁺, theor. 1557.7). HPLC: $t_R$: 8.2 min (Gradient A); $C_{67}H_{101}N_{19}O_{22}S$ (1556.7).

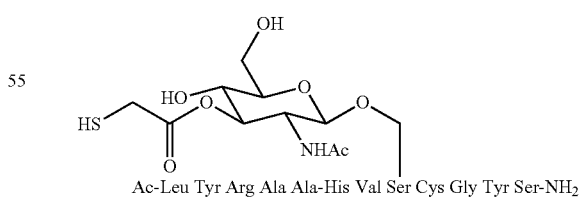

Ac-Leu Tyr Arg Ala Ala-His Val Ser Cys Gly Tyr Ser-NH₂

(SEQ ID NO:48 corresponds to the unmodified amino acids).
Yield: 23%. MALDI-TOF (m/z): 1647.3 ([M+H]⁺, theor. 1645.8). HPLC: $t_R$: 10.2 min (Gradient A); $C_{70}H_{105}N_{19}O_{23}S_2$ (1644.8).

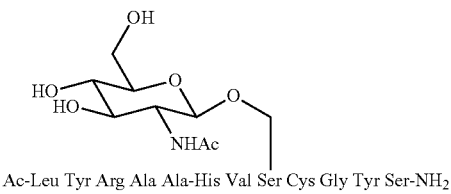
Ac-Leu Tyr Arg Ala Ala-His Val Ser Cys Gly Tyr Ser-NH$_2$ (SEQ ID NO:48 corresponds to the unmodified amino acids).
Yield: >95%. MALDI-TOF (m/z): 1571.0 ([M+H]$^+$, theor. 1571.7). HPLC: t$_R$: 9.5 min (Gradient A); C$_{68}$H$_{103}$N$_{19}$O$_{22}$S (1570.7).

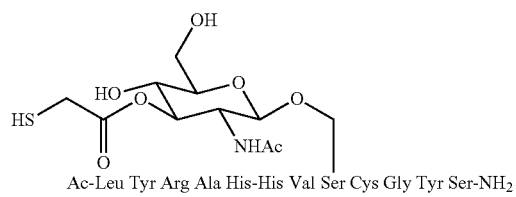
Ac-Leu Tyr Arg Ala His-His Val Ser Cys Gly Tyr Ser-NH$_2$ (SEQ ID NO:49 corresponds to the unmodified amino acids).
Yield: 40%. MALDI-TOF (m/z): 1712.4 ([M+H]$^+$, theor. 1711.9). HPLC: t$_R$: 8.5 min (Gradient A); C$_{73}$H$_{107}$N$_{21}$O$_{23}$S$_2$ (1710.9).

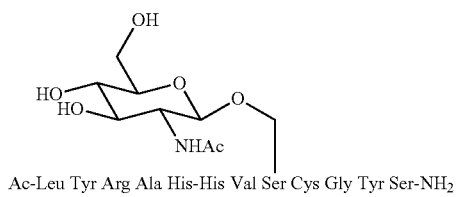
Ac-Leu Tyr Arg Ala His-His Val Ser Cys Gly Tyr Ser-NH$_2$ (SEQ ID NO:49 corresponds to the unmodified amino acids).
Yield: >95%. MALDI-TOF (m/z): 1638.6 ([M+H]$^+$, theor. 1637.8). HPLC: t$_R$: 8.6 min (Gradient A); C$_{71}$H$_{105}$N$_{21}$O$_{22}$S (1636.8).

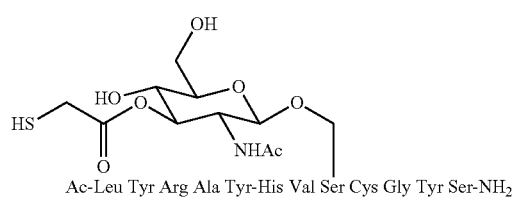
Ac-Leu Tyr Arg Ala Tyr-His Val Ser Cys Gly Tyr Ser-NH$_2$ (SEQ ID NO:50 corresponds to the unmodified amino acids).
Yield: 39%. MALDI-TOF (m/z): 1737.5 ([M+H]$^+$, theor. 1737.9). HPLC: t$_R$: 10.4 min (Gradient A); C$_{76}$H$_{109}$N$_{19}$O$_{24}$S$_2$ (1736.9).

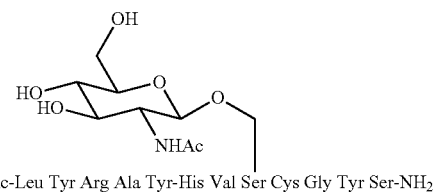
Ac-Leu Tyr Arg Ala Tyr-His Val Ser Cys Gly Tyr Ser-NH$_2$ (SEQ ID NO:50 corresponds to the unmodified amino acids).
Yield: >95%. MALDI-TOF (m/z): 1663.4 ([M+H]$^+$, theor. 1663.8). HPLC: t$_R$: 9.5 min (Gradient A); C$_{74}$H$_{107}$N$_{19}$O$_{23}$S (1662.8).

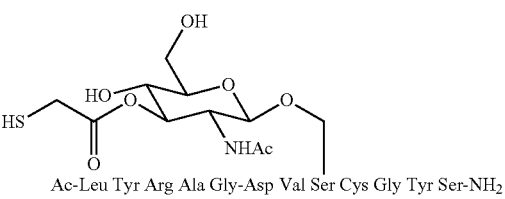
Ac-Leu Tyr Arg Ala Gly-Asp Val Ser Cys Gly Tyr Ser-NH$_2$ (SEQ ID NO:51 corresponds to the unmodified amino acids).
Yield: 81%. MALDI-TOF (m/z): 1608.5 ([M+H]$^+$, theor. 1609.8). HPLC: t$_R$: 9.8 min (Gradient A); C$_{67}$H$_{101}$N$_{17}$O$_{25}$S$_2$ (1608.7).

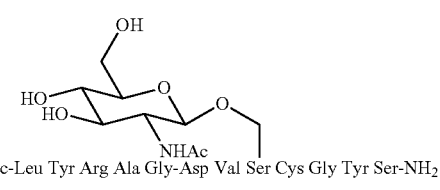
Ac-Leu Tyr Arg Ala Gly-Asp Val Ser Cys Gly Tyr Ser-NH$_2$ (SEQ ID NO:51 corresponds to the unmodified amino acids).
Yield: >95%. MALDI-TOF (m/z): 1535.2 ([M+H]$^+$, theor. 1535.7). HPLC: t$_R$: 9.0 min (Gradient A); C$_{65}$H$_{99}$N$_{17}$O$_{24}$S (1534.6).

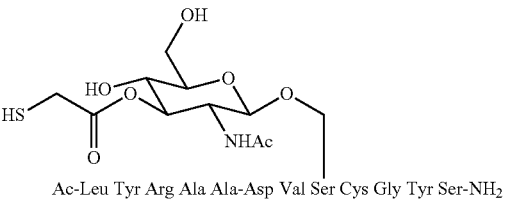
Ac-Leu Tyr Arg Ala Ala-Asp Val Ser Cys Gly Tyr Ser-NH$_2$ (SEQ ID NO:52 corresponds to the unmodified amino acids).
Yield: 50%. MALDI-TOF (m/z): 1623.3 ([M+H]$^+$, theor. 1623.8). HPLC: t$_R$: 10.2 min (Gradient A); C$_{68}$H$_{103}$N$_{17}$O$_{25}$S$_2$ (1622.8).

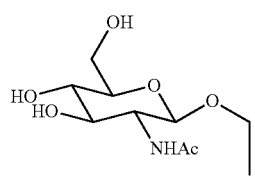
Ac-Leu Tyr Arg Ala Ala-Asp Val Ser Cys Gly Tyr Ser-NH$_2$ (SEQ ID NO:52 corresponds to the unmodified amino acids). Yield: >95%. MALDI-TOF (m/z): 1548.8 ([M+H]$^+$, theor. 1549.7). HPLC: $t_R$: 9.3 min (Gradient A); C$_{66}$H$_{101}$N$_{17}$O$_{24}$S (1548.7).

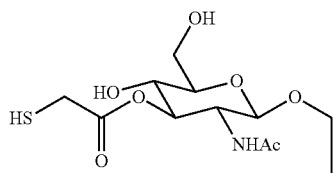
Ac-Leu Tyr Arg Ala His-Asp Val Ser Cys Gly Tyr Ser-NH$_2$ (SEQ ID NO:53 corresponds to the unmodified amino acids). Yield: 60%. MALDI-TOF (m/z): 1687.8 ([M+H]$^+$, theor. 1689.8). HPLC: $t_R$: 9.4 min (Gradient A); C$_{71}$H$_{105}$N$_{19}$O$_{25}$S$_2$ (1688.8).

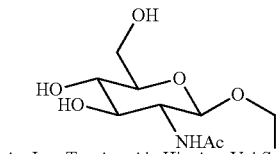
Ac-Leu Tyr Arg Ala His-Asp Val Ser Cys Gly Tyr Ser-NH$_2$ (SEQ ID NO:53 corresponds to the unmodified amino acids). Yield: >95%. MALDI-TOF (m/z): 1616.0 ([M+H]$^+$, theor. 1615.7). HPLC: $t_R$: 8.6 min (Gradient A); C$_{69}$H$_{103}$N$_{19}$O$_{24}$S (1614.7).

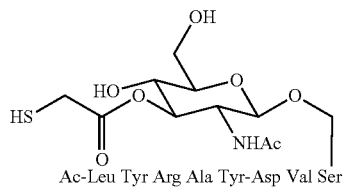
Ac-Leu Tyr Arg Ala Tyr-Asp Val Ser Cys Gly Tyr Ser-NH$_2$ (SEQ ID NO:54 corresponds to the unmodified amino acids). Yield: 37%. MALDI-TOF (m/z): 1714.9 ([M+H]$^+$, theor. 1715.9). HPLC: $t_R$: 10.6 min (Gradient A); C$_{74}$H$_{107}$N$_{17}$O$_{26}$S$_2$ (1714.9).

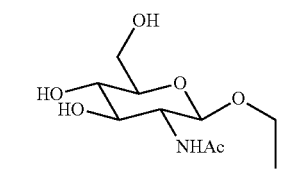
Ac-Leu Tyr Arg Ala Tyr-Asp Val Ser Cys Gly Tyr Ser-NH$_2$ (SEQ ID NO:54 corresponds to the unmodified amino acids). Yield: >95%. MALDI-TOF (m/z): 1640.8 ([M+H]$^+$, theor. 1641.8). HPLC: $t_R$: 9.9 min (Gradient A); C$_{72}$H$_{105}$N$_{17}$O$_{25}$S (1640.8).

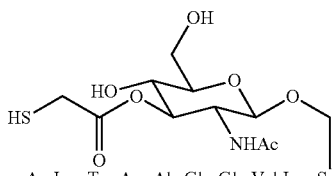
Ac-Leu Tyr Arg Ala Gly-Gly Val Leu Ser Cys Gly Tyr Ser-NH$_2$ (SEQ ID NO:55 corresponds to the unmodified amino acids). Yield: 62%. MALDI-TOF (m/z): 1664.0 ([M+H]$^+$, theor. 1664.9). HPLC: $t_R$: 11.3 min (Gradient A); C$_{71}$H$_{101}$N$_{18}$O$_{24}$S$_2$ (1663.9).

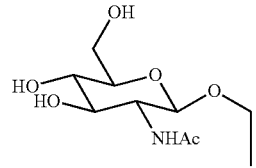
Ac-Leu Tyr Arg Ala Gly-Gly Val Leu Ser Cys Gly Tyr Ser-NH$_2$ (SEQ ID NO:55 corresponds to the unmodified amino acids). Yield: >95%. MALDI-TOF (m/z): 1588.7 ([M+H]$^+$, theor. 1590.8). HPLC: $t_R$: 11.0 min (Gradient A); C$_{69}$H$_{108}$N$_{18}$O$_{23}$S (1589.8).

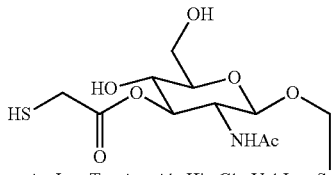
Ac-Leu Tyr Arg Ala His-Gly Val Leu Ser Cys Gly Tyr Ser-NH$_2$ (SEQ ID NO:56 corresponds to the unmodified amino acids). Yield: 81%. MALDI-TOF (m/z): 1745.2 ([M+H]$^+$, theor. 1745.0). HPLC: $t_R$: 10.8 min (Gradient A); C$_{75}$H$_{114}$N$_{20}$O$_{24}$S$_2$ (1744.0).

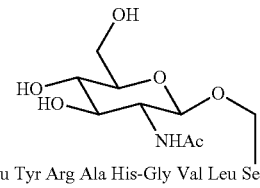
Ac-Leu Tyr Arg Ala His-Gly Val Leu Ser Cys Gly Tyr Ser-NH$_2$ (SEQ ID NO:56 corresponds to the unmodified amino acids). Yield: >95%. MALDI-TOF (m/z): 1670.0 ([M+H]$^+$, theor. 1670.9). HPLC: $t_R$: 9.5 min (Gradient A); C$_{73}$H$_{112}$N$_{20}$O$_{23}$S (1669.9).

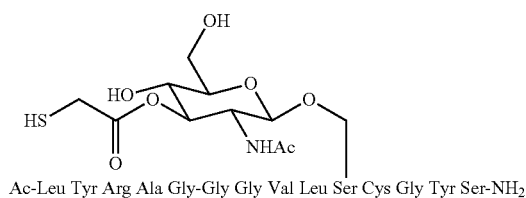
Ac-Leu Tyr Arg Ala Gly-Gly Gly Val Leu Ser Cys Gly Tyr Ser-NH$_2$ (SEQ ID NO:57 corresponds to the unmodified amino acids). Yield: 56%. MALDI-TOF (m/z): 1722.0 ([M+H]$^+$, theor. 1721.9). HPLC: $t_R$: 11.4 min (Gradient A); $C_{73}H_{113}N_{19}O_{25}S_2$ (1720.9).

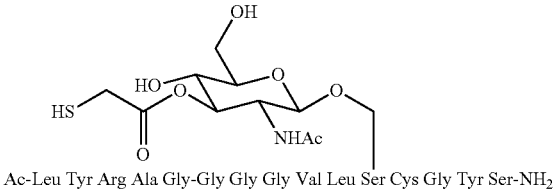
Ac-Leu Tyr Arg Ala Gly-Gly Gly Val Leu Ser Cys Gly Tyr Ser-NH$_2$ (SEQ ID NO:58 corresponds to the unmodified amino acids). Yield: 62%. MALDI-TOF (m/z): 1778.8 ([M+H]$^+$, theor. 1779.0). HPLC: $t_R$: 10.8 min (Gradient A); $C_{75}H_{116}N_{20}O_{26}S_2$ (1778).

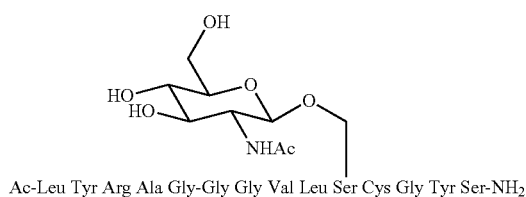
Ac-Leu Tyr Arg Ala Gly-Gly Gly Val Leu Ser Cys Gly Tyr Ser-NH$_2$

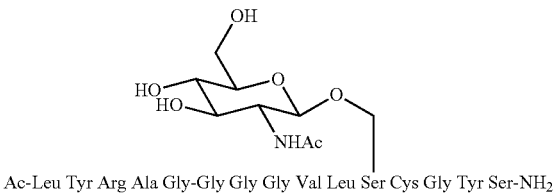
Ac-Leu Tyr Arg Ala Gly-Gly Gly Val Leu Ser Cys Gly Tyr Ser-NH$_2$ (SEQ ID NO:57 corresponds to the unmodified amino acids). Yield: >95%. MALDI-TOF (m/z): 1647.5 ([M+H]$^+$, theor. 1647.8). HPLC: $t_R$: 10.0 min (Gradient A); $C_{71}H_{111}N_{19}O_{24}S$ (1646.8).

(SEQ ID NO:58 corresponds to the unmodified amino acids). Yield: >95%. MALDI-TOF (m/z): 1704.9 ([M+H]$^+$, theor. 1704.9). HPLC: $t_R$: 10.4 min (Gradient A); $C_{73}H_{114}N_{20}O_{25}S$ (1703.9).

Example 41

Synthesis of N-terminal Extended Glycopeptide Reagents

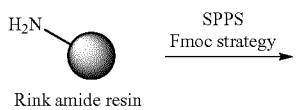

Rink amide resin

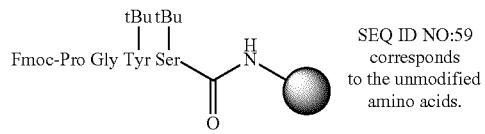

SEQ ID NO:59 corresponds to the unmodified amino acids.

1. DMF/Pip 10%
2. PyBOP, NMM, DMF

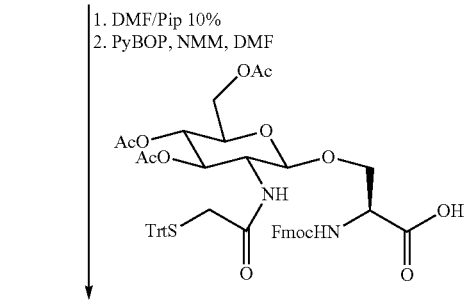

Synthesis of N-terminal Extended Glycopeptide Reagents

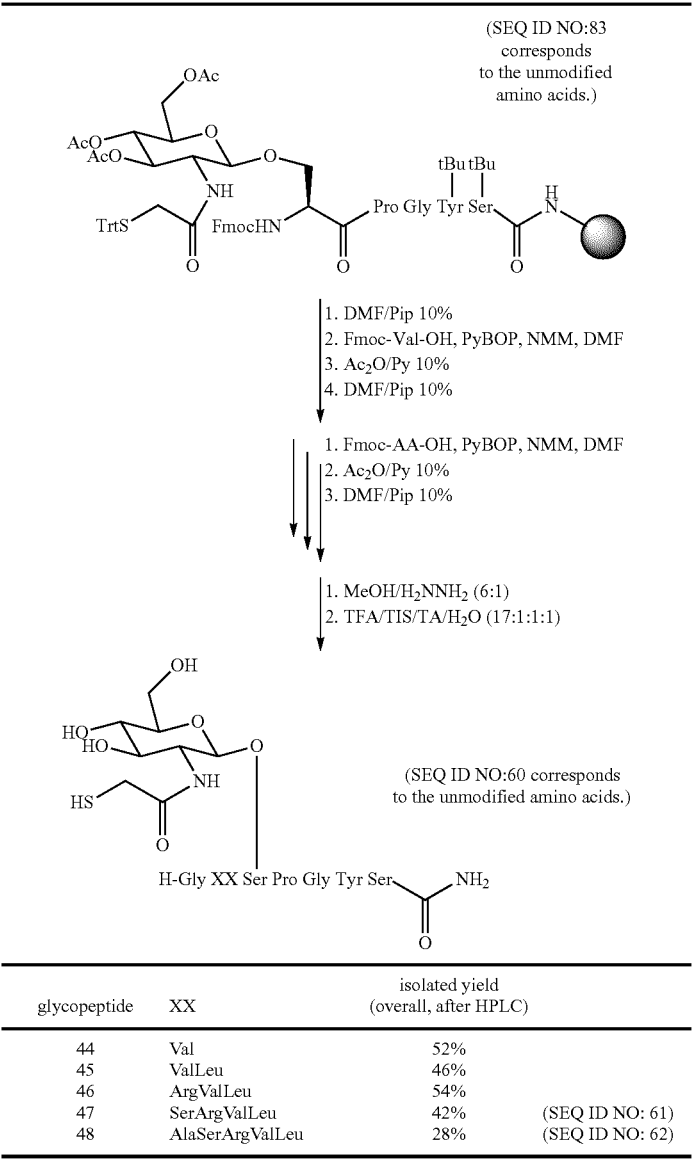

| glycopeptide | XX | isolated yield (overall, after HPLC) | |
|---|---|---|---|
| 44 | Val | 52% | |
| 45 | ValLeu | 46% | |
| 46 | ArgValLeu | 54% | |
| 47 | SerArgValLeu | 42% | (SEQ ID NO: 61) |
| 48 | AlaSerArgValLeu | 28% | (SEQ ID NO: 62) |

Solid Phase Peptide Synthesis of Glycopeptides

Synthesis of the N-terminal extended glycopeptides 44-48 was achieved by solid phase peptide synthesis (SPPS) following the Fmoc-strategy, starting from Fmoc-protected Rink amide resin. To avoid unnecessary expenditure of monomer, only one equivalent was used and the reaction time was increased to 6 h. The UV absorption of the Fmoc/piperidine adduct at 302 nm suggested that these conditions provided acceptable coupling yields. Amino acids possessing sterically hindered side chains were incorporated N-terminal to the glycosylated amino acid to demonstrate the applicability of the method to challenging glycoprotein sequences. For example, glycopeptide 48 contains the sequence Ala-Ser-Arg-Val-Leu (SEQ ID NO:63) before incorporation of an N-terminal glycine. After the desired amino acid sequence was coupled, acetate groups were first removed using hydrazine and the resin was treated with trifluoroacetic acid/thio-anisole/triisopropylsilane/water (85:5:5:5) to cleave the trityl protecting group, the side chain protecting groups and to release the oligomers from the solid support. After purification by HPLC, glycopeptides 44-48 were obtained in yields between 46 and 52%.

Example 42

Extended Sugar-Assisted Ligations

Thioesters bearing the amino acids glycine, histidine, alanine and tyrosine on the C-terminus were synthesized using SPPS via the Boc-strategy.

Initial ligation reactions of the N-terminal extended glycopeptides and the thioester bearing a C-terminal glycine residue were conducted under the standard ligation conditions (6M Gn.HCl 100 mM potassium dihydrogen phosphate, 2% PhSH, 37° C.). In our hands, these conditions caused significant quantities of hydrolyzed thioester, leading to diminished ligation yields. In order to circumvent this problem a range of mixed solvent ligation conditions were analyzed. The most effective solvent system proved to be a mixture of N-methylpyrrolidinone and HEPES buffer (4:1 v/v NMP:6M Gn.HCl 1M HEPES pH 8.5, 2% PhSH, 37° C.) which allowed for facile ligation reactions coupled with a minimal loss of thioester by hydrolysis. reaction of all extended glycopeptides (44-48) and thioester (49) under these conditions gave ligated products which were isolated in good yields. The terms "extended SAL" (exSAL), "double" (dexSAL), "triple" (texSAL), "quadruple" (qexSAL), and "penta-extended" SAL (pexSAL) refer to the number of amino acid residues between the residue bearing the sugar group and the residue with the free N-terminal amino group. In SAL, there is a Gly attached to the amino acid, e.g., serine, bearing the sugar. In exSAL there is one additional intervening amino acid residue, in dexSAL two additional intervening amino acid residues, and so forth. The extended SAL (exSAL) gave an isolated yield of 86%, which was significantly higher than the double-extended SAL (dexSAL) and triple-extended SAL (texSAL) which reacted in 70% and 60% yields respectively. The quadruple-extended and penta-extended SAL (qexSAL and pexSAL) reactions proceeded in even lower yields (38% and 49% respectively).

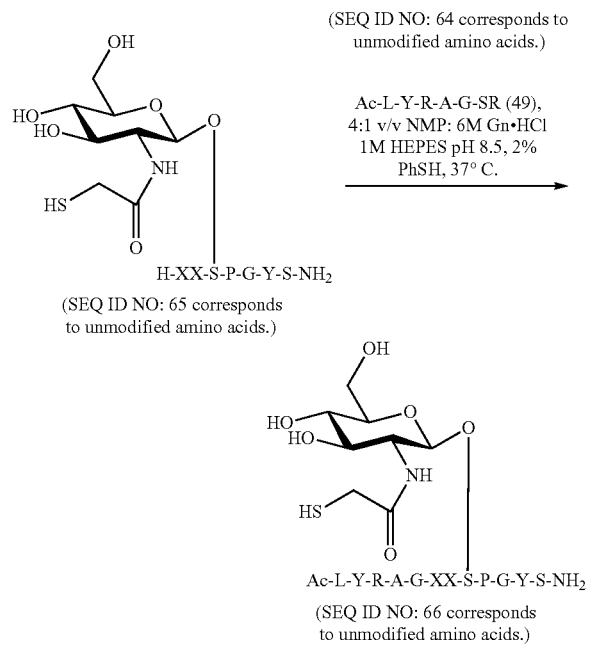

| Ligation method | Glycopeptide XX | Ligation Junction $-AA_2,-AA_1-$ | Isolated ligation yield |
|---|---|---|---|
| exSAL | 44: GlyVal | Gly-Gly | 86% |
| dexSAL | 45: GlyValLeu | Gly-Gly | 70% |
| texSAL | 46: GlyArgValLeu SEQ ID NO: 67 | Gly-Gly | 60% |
| qexSAL | 47: GlySerArgValLeu SEQ ID NO: 68 | Gly-Gly | 38%* |
| pexSAL | 48: GlyAlaSerArgValLeu SEQ ID NO: 69 | Gly-Gly | 49% |

Isolated yields of extended sugar-assisted ligation reactions of glycopeptides 44-48 plus C-terminal glycine thioester 49; conditions: 4:1 v/v NMP:6M Gn.HCl 1M HEPES pH 8.5, 2% PhSH, 37° C. * The HPLC yield of this ligation was similar to the texSAL. The reduced isolated yield is a result of difficult product isolation by HPLC.

Kinetic Studies

It is clear from these studies that there is a significant reduction in ligation yield as amino acids are added to the N-terminus of the glycopeptides. The next phase of the research involved analyzing the kinetics of the reactions, in the hope that this would shed some light on the isolated yields obtained. To this end, a comparison of the rates of the extended SAL methods with the SAL method reported previously was conducted. The rate of product formation was monitored by HPLC every two hours for the first 11 hours and an endpoint was determined after 24 hours. The half life of the SAL reaction was 9 h, slightly faster than the exSAL reaction which displayed a half life of 12 h. Ligations rates became more sluggish as additional amino acids were added to the N-terminus. Interestingly, dexSAL, texSAL and qexSAL reactions exhibited similar rates of ligation with half lives of 19 h. Addition of a sixth amino acid residue in pexSAL resulted in a significant drop in ligation rate, whereby the reaction had only proceeded 42% after 24 h. These kinetic studies clearly indicate that SAL is more facile than its extended counterparts, however, these rates do not differ by an order of magnitude, and as such, all of these extended methods (exSAL, dexSAL, texSAL, qexSAL and pexSAL) should be synthetically useful.

Example 43

Scope of exSAL

To study the effect of other amino acid residues at the ligation junction in exSAL, the glycopeptide-peptide thioester pairs shown below were examined. Glycopeptides containing N-terminal histidine and aspartic acid residues were synthesized by SPPS (Fmoc strategy). These were reacted with peptide thioesters containing C-terminal glycine, histidine and alanine residues under the mixed solvent system. The ligation between glycopeptide 44 and the peptide thioester 49 bearing a C-terminal glycine gave an isolated yield of 86% (entry 1 above). The peptide thioester containing a C-terminal histidine residue ligated in good yield (70%, entry 2 below) in accord with the previously reported SAL method. By increasing the steric bulk of the C-terminal amino acid of the thioester component, the ligation efficiency substantially decreased (44% for Ala-Gly, entry 3 below). Remarkable ligation yields were achieved for glycopeptides which bear an N-terminal aspartic acid residue. The isolated ligation yield which utilized this glycopeptide exceeded those for the glycine glycopeptide 44 (64-91% yield, entries 7-9 below). Suprisingly, even sterically challenging ligation junctions such as His-His (73%, entry 5 below), Ala-His (77%, entry 6 below) and His-Asp (91%, entry 8 below) gave excellent yields.

Scope of the extended sugar-assisted ligation (exSAL); conditions: 4:1 v/v NMP:6M Gn.HCl 1M HEPES pH 8.5, 2% PhSH, 37° C.

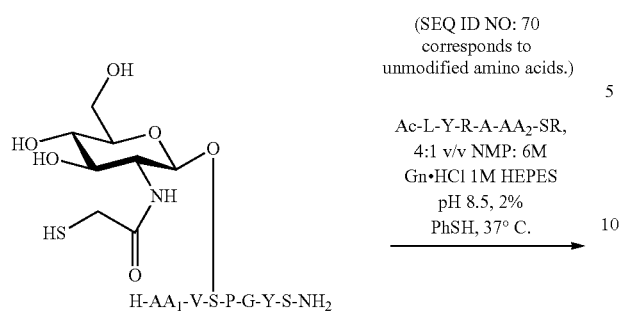

(SEQ ID NO: 70 corresponds to unmodified amino acids.)

Ac-L-Y-R-A-AA$_2$-SR,
4:1 v/v NMP: 6M
Gn•HCl 1M HEPES
pH 8.5, 2%
PhSH, 37° C.

H-AA$_1$-V-S-P-G-Y-S-NH$_2$
(SEQ ID NO: 71 corresponds to unmodified amino acids.)

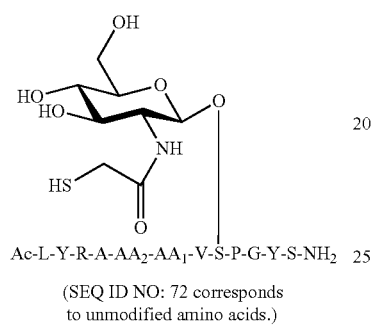

Ac-L-Y-R-A-AA$_2$-AA$_1$-V-S-P-G-Y-S-NH$_2$
(SEQ ID NO: 72 corresponds to unmodified amino acids.)

| Entry | Thioester | Glycopeptide | Ligation Junction -AA$_2$-AA$_1$- | Isolated ligation yield |
|---|---|---|---|---|
| 1 | Gly | Gly | Gly-Gly | 86% |
| 2 | His | Gly | His-Gly | 70% |
| 3 | Ala | Gly | Ala-Gly | 44% |
| 4 | Gly | His | Gly-His | 77% |
| 5 | His | His | His-His | 73% |
| 6 | Ala | His | Ala-His | 77% |
| 7 | Gly | Asp | Gly-Asp | 91% |
| 8 | His | Asp | His-Asp | 91% |
| 9 | Ala | Asp | Ala-Asp | 64% |

Subsequent desulfurization of the ligated products furnished glycopeptides containing the native N-acetyl functionality at the 2-position. This was achieved by hydrogenation conditions using palladium on alumina. Products were generally isolated (after HPLC purification) in quantitative yields (see below).

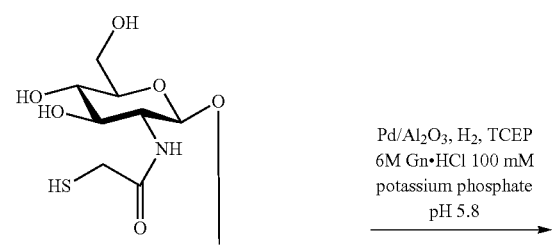

Ac-L-Y-R-A-AA$_2$-AA$_1$-V-S-P-G-Y-S-NH$_2$
(SEQ ID NO: 72 corresponds to unmodified amino acids.)

Pd/Al$_2$O$_3$, H$_2$, TCEP
6M Gn•HCl 100 mM
potassium phosphate
pH 5.8

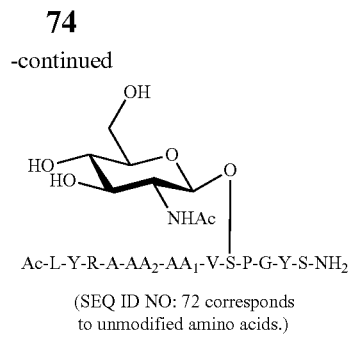

Ac-L-Y-R-A-AA$_2$-AA$_1$-V-S-P-G-Y-S-NH$_2$
(SEQ ID NO: 72 corresponds to unmodified amino acids.)

Desulfurization of exSAL ligation products.

| Entry | Ligation Junction -AA$_2$-AA$_1$- | Isolated desulfurization yield |
|---|---|---|
| 1 | Gly-Gly | 97% |
| 2 | His-Gly | 89% |
| 3 | Ala-Gly | 71% |
| 4 | Gly-His | quant. |
| 5 | His-His | quant. |
| 6 | Ala-His | quant. |
| 7 | Gly-Asp | quant. |
| 8 | His-Asp | 98% |
| 9 | Ala-Asp | quant. |

Scope of dexSAL

We examined the scope of a further extension by application of the dexSAL method to a variety of amino acids at the ligation junction (see below). The glycopeptides were synthesized via SPPS (Fmoc strategy). These glycopeptides were reacted with peptide thioesters bearing C-terminal glycine, alanine, histidine and tyrosine residues using the mixed solvent system described above. Reactions using glycine glycopeptides gave the ligated products in good yields (44-70%). In contrast, glycopeptides containing an N-terminal histidine residue ligated in significantly lower yields when compared to the extended SAL method (24-48%). Gly-His and His-His ligations were isolated in satisfactory yields, however, incorporation of sterically encumbered alanine and tyrosine peptide thioesters resulted in a significant drop in yield (28% and 24% respectively). Aspartate extended glycopeptides ligated in good yields (49-76%) for all cases.

H-AA$_1$-V-L-S-P-G-Y-S-NH$_2$
(SEQ ID NO: 73 corresponds to unmodified amino acids.)

Ac-L-Y-R-A-AA$_2$-SR,
4:1 v/v NMP: 6M
Gn•HCl 1M HEPES
pH 8.5, 2%
PhSH, 37° C.

(SEQ ID NO: 70 corresponds to unmodified amino acids.)

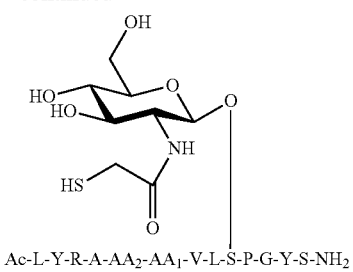

Ac-L-Y-R-A-AA$_2$-AA$_1$-V-L-S-P-G-Y-S-NH$_2$ (SEQ ID NO: 74 corresponds to unmodified amino acids.)

Scope of the double extended sugar-assisted ligation (dexSAL); conditions: 4:1 v/v NMP:6M Gn.HCl 1M HEPES pH 8.5, 2% PhSH, 37° C.

| Entry | Thioester | Glycopeptide | Ligation Junction -AA$_2$-AA$_1$- | Isolated ligation yield |
|---|---|---|---|---|
| 1 | Gly | Gly | Gly-Gly | 70% |
| 2 | His | Gly | His-Gly | 65% |
| 3 | Ala | Gly | Ala-Gly | 53% |
| 4 | Tyr | Gly | Tyr-Gly | 44% |
| 5 | Gly | His | Gly-His | 48% |
| 6 | His | His | His-His | 44% |
| 7 | Ala | His | Ala-His | 28% |
| 8 | Tyr | His | Tyr-His | 24% |
| 9 | Gly | Asp | Gly-Asp | 76% |
| 10 | His | Asp | His-Asp | 60% |
| 11 | Ala | Asp | Ala-Asp | 49% |
| 12 | Tyr | Asp | Tyr-Asp | 68% |

The observed flexibility of the exSAL and dexSAL methods with a variety of amino acids at the ligation junction was extended to ligation of sterically challenging peptide thioesters with glycopeptides 46-48 via texSAL, qexSAL and pexSAL respectively. These glycopeptides ligated in satisfactory yields with this thioester (49, 48 and 31% for texSAL, qexSAL and pexSAL respectively).

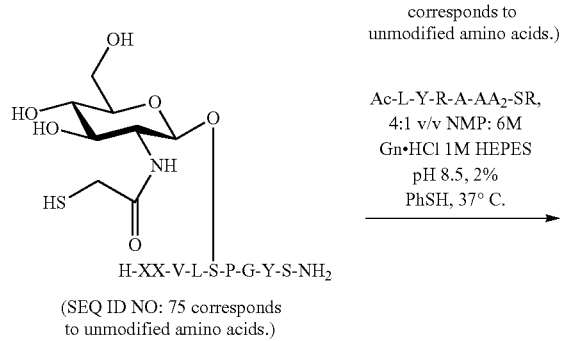

(SEQ ID NO: 75 corresponds to unmodified amino acids.)

(SEQ ID NO: 70 corresponds to unmodified amino acids.)

Ac-L-Y-R-A-AA$_2$-SR, 4:1 v/v NMP: 6M Gn•HCl 1M HEPES pH 8.5, 2% PhSH, 37° C.

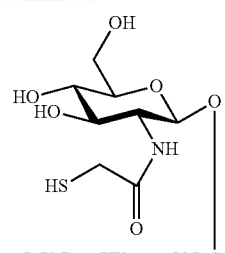

Ac-L-Y-R-A-XX-AA$_1$-V-L-S-P-G-Y-S-NH$_2$ (SEQ ID NO: 76 corresponds to unmodified amino acids.)

Triple-, quadrupal- and penta-extended sugar-assisted ligations of glycopeptides X-X with C-terminal glycine and alanine peptide thioesters

| Entry | Thioester | Glycopeptide XX | Ligation Junction -AA$_2$-AA$_1$- | Isolated ligation yield |
|---|---|---|---|---|
| 1 | Gly | GlyArg | Gly-Gly | 60% |
| 2 | Gly | GlySerArg | Gly-Gly | 38% |
| 3 | Gly | GlyAlaSerArg SEQ ID NO: 77 | Gly-Gly | 49% |
| 4 | Ala | GlyArg | Ala-Gly | 48% |
| 5 | Ala | GlySerArg | Ala-Gly | 31% |
| 6 | Ala | GlyAlaSerArg SEQ ID NO: 77 | Ala-Gly | 34% |

Example 44

Ligation with Asn-Linked Sugar Moiety

A)

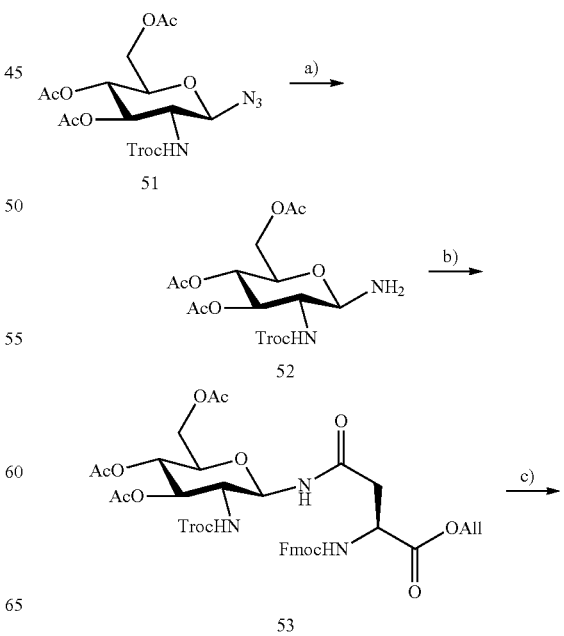

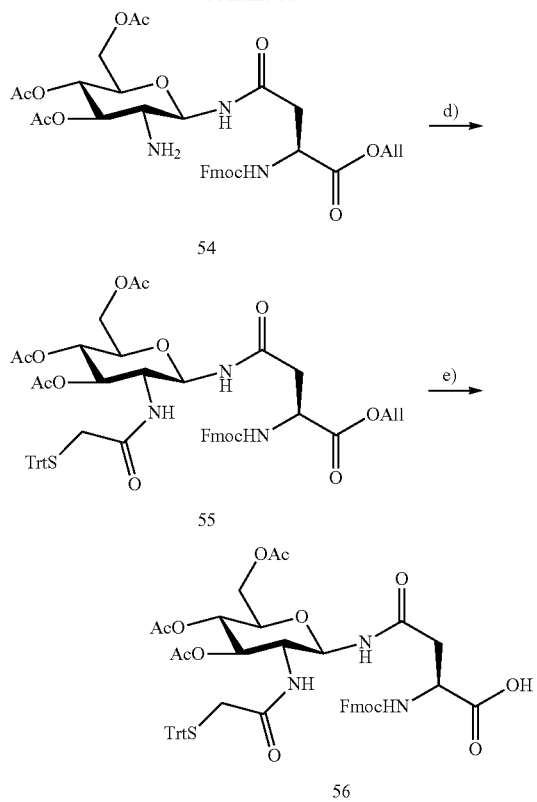

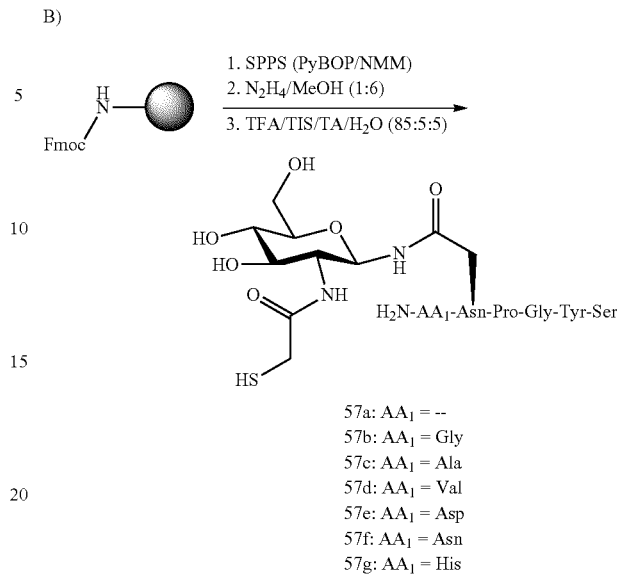

57a: AA₁ = --
57b: AA₁ = Gly
57c: AA₁ = Ala
57d: AA₁ = Val
57e: AA₁ = Asp
57f: AA₁ = Asn
57g: AA₁ = His (SEQ ID NO:78 corresponds to the unmodified amino acids.)

A) Synthesis of the building block 56: Reagents and conditions: a) propanedithiol, DIEA, MeOH, 4 h, rt, b) Fmoc-(Asp)-OAll, HBTU, DIEA, DMF, 12 h, 90%; c) Zn, AcOH, rt, 12 h, 85%; d) TrtS-CH₂—COOH, HBTU, DIEA, DMF, 4 h, rt, 78%; e) Pd(PPh₃)₄, NMA, THF, 1 h, rt, 90%.

B) SPPS synthesis of glycopeptides on Fmoc-Rink amide polystyrene resin.

---

What is claimed is:

1. A method of preparing a compound of Formula (I):

(I)

including any stereoisomers, tautomers, solvates, hydrates, or salts thereof;
wherein
 m is 0 to about 10;
 n is 1 to about 4;
 $R^a$ and $R^b$ are each independently at each occurrence H or alkyl, or $R^a$ and $R^b$ together are oxo (=O);
 p is 1, 2, or 3;
 X is O or $CHR^3$;
 each $R^3$ is independently at each occurrence hydrogen, $(C_1-C_3)$alkyl, hydroxy, or hydroxy$(C_1-C_3)$alkyl, wherein any hydroxy or hydroxyalkyl can be O-substituted with a monosaccharide, a disaccharide, an oligosaccharide, or a hydroxy-protecting group; provided that one $R^3$ comprises —OC(=O)(CH($R^s$))$_s$SH or —NHC(=O)(CH($R^s$))$_s$SH, wherein $R^s$ is independently at each occurrence hydrogen or $(C_1-C_6)$alkyl wherein any carbon atom of the $(C_1-C_6)$alkyl can be substituted with J, and s is 1 to about 6;
 Y is $C(R^4R^5)$, O, NH or S;
 $R^4$ and $R^5$ are each independently H, alkyl, or J;
 the carbon atom bearing X and Y is in the R or the S configuration;
 each NR is independently NH or $N(C_1-C_3)$alkyl, or an NR, together with an $R^c$ or $R^e$ bonded to a carbon atom bearing the NR, can form a 4-7 membered ring, or
 each $R^c$, $R^{c\prime}$, $R^e$, and $R^{e\prime}$ is independently at each occurrence H, alkyl, aryl, heteroaryl, cycloalkyl, or heterocyclyl, or a sidechain of a naturally occurring amino acid which can be unblocked or blocked with a protecting group; or $R^c$ and $R^{c\prime}$ or $R^e$ and $R^{e\prime}$, or both, together with a carbon atom to which they are attached, form a cycloalkyl or heterocycloalkyl; wherein any alkyl, aryl, heteroaryl, cycloalkyl, or heterocyclyl is substituted with 0-3 J;
 J is halogen, trifluoromethyl, cyano, nitro, $(C_{1-6})$alkyl, $(C_{1-6})$alkoxy, cycloalkyl, carboxy; acetamido, hydroxy, hydroxy$(C_{1-6})$alkyl, trifluoromethoxy, sulfamoyl, carbamoyl, sulfonamido, alkylsulfonyl, or arylsulfonyl; and
 $R^1$ and $R^2$ are each independently a peptide residue or a glycopeptide residue;
 the method comprising: contacting a compound of Formula (II):

(II)

and a compound of Formula (III):

(III)

wherein $R^d$ is alkyl, aryl, aralkyl, carboxyalkyl or carboxamidoalkyl; to provide the compound of formula (I).

2. The method of claim 1 wherein $R^s$ is H and s is 1.

3. The method of claim 1 wherein n is 1, Y is O, and $R^a$ is H or methyl and $R^b$ is H.

4. The method of claim 1 wherein Y is NH, and $(CR^aR^b)_n$ is —$CH_2C(O)$— or $(CH_2)_2C(O)$—.

5. The method of claim 1 wherein $R^d$ is methyl, phenyl, or —$(CH_2)_2C(O)NH_2$.

6. The method of claim 1 wherein m is 1, 2, 3, 4, 5, or 6.

7. The method of claim 1 wherein the carbon atom bearing X and Y is in the R configuration.

8. The method of claim 1 wherein the carbon atom bearing X and Y is in the S configuration.

9. The method of claim 1 wherein $R^2$ is phenylalaninamide.

10. The method of claim 1 wherein $R^1$ is N-acetyl-Leu-Tyr-Arg-Ala (SEQ ID NO:1).

11. The method of claim 1 wherein $R^e$ and $R^{e'}$ of the N-terminal amino acid residue of the compound of formula (II) are both H.

12. The method of claim 1 wherein X is O.

13. The method of claim 1 wherein X is CHOH.

14. The method of claim 1 wherein the contacting comprises contacting in an aqueous solution.

15. The method of claim 1 wherein the contacting comprises contacting in an alkaline aqueous solution.

16. The method of claim 1 wherein the contacting comprises contacting in an alkaline aqueous solution comprising guanidine.

17. The method of claim 1 wherein the contacting comprises contacting in an alkaline aqueous solution comprising a thiol.

18. The method of claim 1 wherein the contacting comprises contacting in an alkaline aqueous solution comprising thiophenol.

19. The method of claim 1 wherein the contacting is carried out at about 35° C. to about 40° C.

20. The method of claim 1 wherein the concentration of the compound of formula (III) is about 5 mM to about 20 mM.

21. The method of claim 1 wherein the concentration of the compound of formula (III) is about 7.5 mM to about 15 mM.

22. The method of claim 1 wherein the compound of formula (II) and the compound of formula (III) are employed in a molar ratio of about 0.8 to about 1.2.

23. The method of claim 1 wherein the compound of formula (I) is obtained in a yield of at least about 70 molar percent.

24. The method of claim 1 wherein the compound of formula (I) is obtained in a purity of greater than about 90%.

25. The method of claim 1 wherein the contacting is carried out for a time period of about 6 hours to about 24 hours.

26. The method of claim 1 wherein the contacting is carried out for a time period of about 6 hours to about 18 hours.

27. The method of claim 1 further comprising purifying the compound of formula (I) by HPLC.

28. A method of desulfurizing a compound of Formula (I):

(I)

including any stereoisomers, tautomers, solvates, hydrates, or salts thereof;
wherein
m is 0 to about 10;
n is 1 to about 4;
$R^a$ and $R^b$ are each independently at each occurrence H or alkyl, or $R^a$ and $R^b$ together are oxo (=O);
p is 1, 2, or 3;
X is O or $CHR^3$;
each $R^3$ is independently at each occurrence hydrogen, $(C_1-C_3)$alkyl, hydroxy, or hydroxy$(C_1-C_3)$alkyl, wherein any hydroxy or hydroxyalkyl can be O-substituted with a monosaccharide, a disaccharide, an oligosaccharide, or a hydroxy-protecting group; provided that one $R^3$ comprises $-OC(=O)(CH(R^s))_sSH$ or $-NHC(=O)(CH(R^s))_sSH$, wherein $R^s$ is independently at each occurrence hydrogen or $(C_1-C_6)$alkyl wherein any carbon atom of the $(C_1-C_6)$alkyl can be substituted with J, and s is 1 to about 6;
Y is $C(R^4R^5)$, O, NH or S;
$R^4$ and $R^5$ are each independently H, alkyl, or J;
the carbon atom bearing X and Y is in the R or the S configuration;
each NR is independently NH or $N(C_1-C_3)$alkyl, or an NR, together with an $R^c$ or $R^e$ bonded to a carbon atom bearing the NR, can form a 4-7 membered ring, or
each $R^c$, $R^{c'}$, $R^e$, and $R^{e'}$ is independently at each occurrence H, alkyl, aryl, heteroaryl, cycloalkyl, or heterocyclyl, or a sidechain of a naturally occurring amino acid which can be unblocked or blocked with a protecting group; or $R^c$ and $R^{c'}$ or $R^e$ and $R^{e'}$, or both, together with a carbon atom to which they are attached, form a cycloalkyl or heterocycloalkyl; wherein any alkyl, aryl, heteroaryl, cycloalkyl, or heterocyclyl is substituted with 0-3 J;
J is halogen, trifluoromethyl, cyano, nitro, $(C_{1-6})$alkyl, $(C_{1-6})$alkoxy, cycloalkyl, carboxy; acetamido, hydroxy, hydroxy$(C_{1-6})$alkyl, trifluoromethoxy, sulfamoyl, carbamoyl, sulfonamido, alkylsulfonyl, or arylsulfonyl; and
$R^1$ and $R^2$ are each independently a peptide residue or a glycopeptide residue;
the method comprising:
contacting a compound of Formula (II):

(II)

and a compound of Formula (III):

(III)

wherein $R^d$ is alkyl, aryl, aralkyl, carboxyalkyl or carboxamidoalkyl; to provide the compound of formula (I); and desulfurizing said compound of Formula (I) by contacting the compound with a source of hydrogen in the presence of a catalyst.

29. The method of claim 28 wherein the source of hydrogen is hydrogen gas.

30. The method of claim 28 wherein the catalyst is a palladium group metal.

31. The method of claim 28 wherein the catalyst is palladium metal.

32. The method of claim 28 wherein the source of hydrogen is a borohydride salt.

33. The method of claim 28 wherein the source of hydrogen is sodium borohydride.

34. The method of claim 28 wherein the catalyst is Raney nickel.

35. The method of claim 28 wherein the contacting comprises contacting in aqueous solution.

36. The method of claim 28 wherein the contacting comprises contacting in an aqueous solution comprising guanidine.

* * * * *

UNITED STATES PATENT AND TRADEMARK OFFICE
CERTIFICATE OF CORRECTION

PATENT NO. : 8,816,050 B2
APPLICATION NO. : 12/293793
DATED : August 26, 2014
INVENTOR(S) : Wong et al.

Page 1 of 1

It is certified that error appears in the above-identified patent and that said Letters Patent is hereby corrected as shown below:

In the Specification

Column 1, Lines 12-17, the paragraph GOVERNMENT FUNDING STATEMENT should be changed to:
-- STATEMENT OF GOVERNMENT LICENSE RIGHTS
This invention was made with government support under grant numbers GM044154 and GM048870 awarded by the National Institutes of Health. The government has certain rights in the invention. --

Signed and Sealed this
Seventh Day of April, 2020

Andrei Iancu
*Director of the United States Patent and Trademark Office*

SEQUENCE LISTING

<160> NUMBER OF SEQ ID NOS: 83

<210> SEQ ID NO 1
<211> LENGTH: 4
<212> TYPE: PRT
<213> ORGANISM: Artificial Sequence
<220> FEATURE:
<223> OTHER INFORMATION: A synthetic peptide

<400> SEQUENCE: 1

Leu Tyr Arg Ala
1

<210> SEQ ID NO 2
<211> LENGTH: 4
<212> TYPE: PRT
<213> ORGANISM: Artificial Sequence
<220> FEATURE:
<223> OTHER INFORMATION: A synthetic peptide

<400> SEQUENCE: 2

Pro Tyr Gly Ser
1

<210> SEQ ID NO 3
<211> LENGTH: 5
<212> TYPE: PRT
<213> ORGANISM: Artificial Sequence
<220> FEATURE:
<223> OTHER INFORMATION: A synthetic peptide

<400> SEQUENCE: 3

```
Leu Tyr Arg Ala Gly
1               5

<210> SEQ ID NO 4
<211> LENGTH: 5
<212> TYPE: PRT
<213> ORGANISM: Artificial Sequence
<220> FEATURE:
<223> OTHER INFORMATION: A synthetic peptide

<400> SEQUENCE: 4

Leu Tyr Arg Ala Ala
1               5

<210> SEQ ID NO 5
<211> LENGTH: 5
<212> TYPE: PRT
<213> ORGANISM: Artificial Sequence
<220> FEATURE:
<223> OTHER INFORMATION: A synthetic peptide

<400> SEQUENCE: 5

Leu Tyr Arg Ala Val
1               5

<210> SEQ ID NO 6
<211> LENGTH: 5
<212> TYPE: PRT
<213> ORGANISM: Artificial Sequence
<220> FEATURE:
<223> OTHER INFORMATION: A synthetic peptide

<400> SEQUENCE: 6

Leu Tyr Arg Ala His
1               5

<210> SEQ ID NO 7
<211> LENGTH: 5
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 7

Leu Tyr Arg Ala Xaa
1               5

<210> SEQ ID NO 8
<211> LENGTH: 8
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 8

Leu Tyr Arg Ala Xaa Gly Ser Phe
1               5

<210> SEQ ID NO 9
```

```
<211> LENGTH: 8
<212> TYPE: PRT
<213> ORGANISM: Artificial Sequence
<220> FEATURE:
<223> OTHER INFORMATION: A synthetic peptide

<400> SEQUENCE: 9

Leu Tyr Arg Ala Gly Gly Ser Phe
1               5

<210> SEQ ID NO 10
<211> LENGTH: 6
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 10

Xaa Xaa Pro Gly Tyr Ser
1               5

<210> SEQ ID NO 11
<211> LENGTH: 22
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (17)..(18)
<223> OTHER INFORMATION: Xaa can be any naturally occurring amino acid

<400> SEQUENCE: 11

Cys Leu Asn Leu Gln Gly Gly Gly Gly Gln Arg Gly Asp Gly Gly
1               5                   10                  15

Xaa Xaa Pro Gly Tyr Ser
            20

<210> SEQ ID NO 12
<211> LENGTH: 6
<212> TYPE: PRT
<213> ORGANISM: Artificial Sequence
<220> FEATURE:
<223> OTHER INFORMATION: A synthetic peptide

<400> SEQUENCE: 12

Gly Ser Pro Gly Tyr Ser
1               5

<210> SEQ ID NO 13
<211> LENGTH: 6
<212> TYPE: PRT
<213> ORGANISM: Artificial Sequence
<220> FEATURE:
<223> OTHER INFORMATION: A synthetic peptide

<400> SEQUENCE: 13

Gly Ser Cys Gly Tyr Ser
1               5

<210> SEQ ID NO 14
<211> LENGTH: 6
<212> TYPE: PRT
<213> ORGANISM: Artificial Sequence
```

```
<220> FEATURE:
<223> OTHER INFORMATION: A synthetic peptide

<400> SEQUENCE: 14

Asp Ser Cys Gly Tyr Ser
1               5

<210> SEQ ID NO 15
<211> LENGTH: 6
<212> TYPE: PRT
<213> ORGANISM: Artificial Sequence
<220> FEATURE:
<223> OTHER INFORMATION: A synthetic peptide

<400> SEQUENCE: 15

His Ser Cys Gly Tyr Ser
1               5

<210> SEQ ID NO 16
<211> LENGTH: 7
<212> TYPE: PRT
<213> ORGANISM: Artificial Sequence
<220> FEATURE:
<223> OTHER INFORMATION: A synthetic peptide

<400> SEQUENCE: 16

Gly Val Ser Pro Gly Tyr Ser
1               5

<210> SEQ ID NO 17
<211> LENGTH: 7
<212> TYPE: PRT
<213> ORGANISM: Artificial Sequence
<220> FEATURE:
<223> OTHER INFORMATION: A synthetic peptide

<400> SEQUENCE: 17

Gly Val Ser Cys Gly Tyr Ser
1               5

<210> SEQ ID NO 18
<211> LENGTH: 7
<212> TYPE: PRT
<213> ORGANISM: Artificial Sequence
<220> FEATURE:
<223> OTHER INFORMATION: A synthetic peptide

<400> SEQUENCE: 18

Asp Val Ser Cys Gly Tyr Ser
1               5

<210> SEQ ID NO 19
<211> LENGTH: 7
<212> TYPE: PRT
<213> ORGANISM: Artificial Sequence
<220> FEATURE:
<223> OTHER INFORMATION: A synthetic peptide

<400> SEQUENCE: 19

His Val Ser Cys Gly Tyr Ser
1               5

<210> SEQ ID NO 20
<211> LENGTH: 8
<212> TYPE: PRT
<213> ORGANISM: Artificial Sequence
<220> FEATURE:
```

```
<223> OTHER INFORMATION: A synthetic peptide

<400> SEQUENCE: 20

Gly Val Leu Ser Cys Gly Tyr Ser
1               5

<210> SEQ ID NO 21
<211> LENGTH: 9
<212> TYPE: PRT
<213> ORGANISM: Artificial Sequence
<220> FEATURE:
<223> OTHER INFORMATION: A synthetic peptide

<400> SEQUENCE: 21

Gly Gly Val Leu Ser Cys Gly Tyr Ser
1               5

<210> SEQ ID NO 22
<211> LENGTH: 10
<212> TYPE: PRT
<213> ORGANISM: Artificial Sequence
<220> FEATURE:
<223> OTHER INFORMATION: A synthetic peptide

<400> SEQUENCE: 22

Gly Gly Gly Val Leu Ser Cys Gly Tyr Ser
1               5                   10

<210> SEQ ID NO 23
<211> LENGTH: 5
<212> TYPE: PRT
<213> ORGANISM: Artificial Sequence
<220> FEATURE:
<223> OTHER INFORMATION: A synthetic peptide

<400> SEQUENCE: 23

Leu Tyr Arg Ala Gly
1               5

<210> SEQ ID NO 24
<211> LENGTH: 5
<212> TYPE: PRT
<213> ORGANISM: Artificial Sequence
<220> FEATURE:
<223> OTHER INFORMATION: A synthetic peptide

<400> SEQUENCE: 24

Leu Tyr Arg Ala Ala
1               5

<210> SEQ ID NO 25
<211> LENGTH: 5
<212> TYPE: PRT
<213> ORGANISM: Artificial Sequence
<220> FEATURE:
<223> OTHER INFORMATION: A synthetic peptide

<400> SEQUENCE: 25

Leu Tyr Arg Ala Tyr
1               5

<210> SEQ ID NO 26
<211> LENGTH: 5
<212> TYPE: PRT
<213> ORGANISM: Artificial Sequence
<220> FEATURE:
<223> OTHER INFORMATION: A synthetic peptide
```

```
<400> SEQUENCE: 26

Leu Tyr Arg Ala His
1               5

<210> SEQ ID NO 27
<211> LENGTH: 5
<212> TYPE: PRT
<213> ORGANISM: Artificial Sequence
<220> FEATURE:
<223> OTHER INFORMATION: A synthetic peptide

<400> SEQUENCE: 27

Leu Tyr Arg Ala Phe
1               5

<210> SEQ ID NO 28
<211> LENGTH: 11
<212> TYPE: PRT
<213> ORGANISM: Artificial Sequence
<220> FEATURE:
<223> OTHER INFORMATION: A synthetic peptide

<400> SEQUENCE: 28

Leu Tyr Arg Ala Gly Gly Ser Pro Gly Tyr Ser
1               5                   10

<210> SEQ ID NO 29
<211> LENGTH: 11
<212> TYPE: PRT
<213> ORGANISM: Artificial Sequence
<220> FEATURE:
<223> OTHER INFORMATION: A synthetic peptide

<400> SEQUENCE: 29

Leu Tyr Arg Ala Gly Gly Ser Cys Gly Tyr Ser
1               5                   10

<210> SEQ ID NO 30
<211> LENGTH: 11
<212> TYPE: PRT
<213> ORGANISM: Artificial Sequence
<220> FEATURE:
<223> OTHER INFORMATION: A synthetic peptide

<400> SEQUENCE: 30

Leu Tyr Arg Ala Gly His Ser Cys Gly Tyr Ser
1               5                   10

<210> SEQ ID NO 31
<211> LENGTH: 11
<212> TYPE: PRT
<213> ORGANISM: Artificial Sequence
<220> FEATURE:
<223> OTHER INFORMATION: A synthetic peptide

<400> SEQUENCE: 31

Leu Tyr Arg Ala His His Ser Cys Gly Tyr Ser
1               5                   10

<210> SEQ ID NO 32
<211> LENGTH: 11
<212> TYPE: PRT
<213> ORGANISM: Artificial Sequence
<220> FEATURE:
<223> OTHER INFORMATION: A synthetic peptide
```

```
<400> SEQUENCE: 32

Leu Tyr Arg Ala Gly Asp Ser Cys Gly Tyr Ser
1               5                   10

<210> SEQ ID NO 33
<211> LENGTH: 11
<212> TYPE: PRT
<213> ORGANISM: Artificial Sequence
<220> FEATURE:
<223> OTHER INFORMATION: A synthetic peptide

<400> SEQUENCE: 33

Leu Tyr Arg Ala His Asp Ser Cys Gly Tyr Ser
1               5                   10

<210> SEQ ID NO 34
<211> LENGTH: 11
<212> TYPE: PRT
<213> ORGANISM: Artificial Sequence
<220> FEATURE:
<223> OTHER INFORMATION: A synthetic peptide

<400> SEQUENCE: 34

Leu Tyr Arg Ala Tyr Asp Ser Cys Gly Tyr Ser
1               5                   10

<210> SEQ ID NO 35
<211> LENGTH: 11
<212> TYPE: PRT
<213> ORGANISM: Artificial Sequence
<220> FEATURE:
<223> OTHER INFORMATION: A synthetic peptide

<400> SEQUENCE: 35

Leu Tyr Arg Ala Ala Gly Ser Cys Gly Tyr Ser
1               5                   10

<210> SEQ ID NO 36
<211> LENGTH: 11
<212> TYPE: PRT
<213> ORGANISM: Artificial Sequence
<220> FEATURE:
<223> OTHER INFORMATION: A synthetic peptide

<400> SEQUENCE: 36

Leu Tyr Arg Ala Tyr His Ser Cys Gly Tyr Ser
1               5                   10

<210> SEQ ID NO 37
<211> LENGTH: 11
<212> TYPE: PRT
<213> ORGANISM: Artificial Sequence
<220> FEATURE:
<223> OTHER INFORMATION: A synthetic peptide

<400> SEQUENCE: 37

Leu Tyr Arg Ala Ala His Ser Cys Gly Tyr Ser
1               5                   10

<210> SEQ ID NO 38
<211> LENGTH: 11
<212> TYPE: PRT
<213> ORGANISM: Artificial Sequence
<220> FEATURE:
<223> OTHER INFORMATION: A synthetic peptide

<400> SEQUENCE: 38
```

```
Leu Tyr Arg Ala Ala Asp Ser Cys Gly Tyr Ser
1               5                   10

<210> SEQ ID NO 39
<211> LENGTH: 11
<212> TYPE: PRT
<213> ORGANISM: Artificial Sequence
<220> FEATURE:
<223> OTHER INFORMATION: A synthetic peptide

<400> SEQUENCE: 39

Leu Tyr Arg Ala His Gly Ser Cys Gly Tyr Ser
1               5                   10

<210> SEQ ID NO 40
<211> LENGTH: 12
<212> TYPE: PRT
<213> ORGANISM: Artificial Sequence
<220> FEATURE:
<223> OTHER INFORMATION: A synthetic peptide

<400> SEQUENCE: 40

Leu Tyr Arg Ala Ala Gly Val Ser Pro Gly Tyr Ser
1               5                   10

<210> SEQ ID NO 41
<211> LENGTH: 12
<212> TYPE: PRT
<213> ORGANISM: Artificial Sequence
<220> FEATURE:
<223> OTHER INFORMATION: A synthetic peptide

<400> SEQUENCE: 41

Leu Tyr Arg Ala His Gly Val Ser Pro Gly Tyr Ser
1               5                   10

<210> SEQ ID NO 42
<211> LENGTH: 12
<212> TYPE: PRT
<213> ORGANISM: Artificial Sequence
<220> FEATURE:
<223> OTHER INFORMATION: A synthetic peptide

<400> SEQUENCE: 42

Leu Tyr Arg Ala Ala Gly Val Ser Cys Gly Tyr Ser
1               5                   10

<210> SEQ ID NO 43
<211> LENGTH: 12
<212> TYPE: PRT
<213> ORGANISM: Artificial Sequence
<220> FEATURE:
<223> OTHER INFORMATION: A synthetic peptide

<400> SEQUENCE: 43

Leu Tyr Arg Ala Gly Gly Val Ser Cys Gly Tyr Ser
1               5                   10

<210> SEQ ID NO 44
<211> LENGTH: 12
<212> TYPE: PRT
<213> ORGANISM: Artificial Sequence
<220> FEATURE:
<223> OTHER INFORMATION: A synthetic peptide

<400> SEQUENCE: 44
```

```
Leu Tyr Arg Ala Gly Gly Val Ser Pro Gly Tyr Ser
1               5                   10
```

<210> SEQ ID NO 45
<211> LENGTH: 12
<212> TYPE: PRT
<213> ORGANISM: Artificial Sequence
<220> FEATURE:
<223> OTHER INFORMATION: A synthetic peptide

<400> SEQUENCE: 45

```
Leu Tyr Arg Ala His Gly Val Ser Cys Gly Tyr Ser
1               5                   10
```

<210> SEQ ID NO 46
<211> LENGTH: 12
<212> TYPE: PRT
<213> ORGANISM: Artificial Sequence
<220> FEATURE:
<223> OTHER INFORMATION: A synthetic peptide

<400> SEQUENCE: 46

```
Leu Tyr Arg Ala Tyr Gly Val Ser Cys Gly Tyr Ser
1               5                   10
```

<210> SEQ ID NO 47
<211> LENGTH: 12
<212> TYPE: PRT
<213> ORGANISM: Artificial Sequence
<220> FEATURE:
<223> OTHER INFORMATION: A synthetic peptide

<400> SEQUENCE: 47

```
Leu Tyr Arg Ala Gly His Val Ser Cys Gly Tyr Ser
1               5                   10
```

<210> SEQ ID NO 48
<211> LENGTH: 12
<212> TYPE: PRT
<213> ORGANISM: Artificial Sequence
<220> FEATURE:
<223> OTHER INFORMATION: A synthetic peptide

<400> SEQUENCE: 48

```
Leu Tyr Arg Ala Ala His Val Ser Cys Gly Tyr Ser
1               5                   10
```

<210> SEQ ID NO 49
<211> LENGTH: 12
<212> TYPE: PRT
<213> ORGANISM: Artificial Sequence
<220> FEATURE:
<223> OTHER INFORMATION: A synthetic peptide

<400> SEQUENCE: 49

```
Leu Tyr Arg Ala His His Val Ser Cys Gly Tyr Ser
1               5                   10
```

<210> SEQ ID NO 50
<211> LENGTH: 12
<212> TYPE: PRT
<213> ORGANISM: Artificial Sequence
<220> FEATURE:
<223> OTHER INFORMATION: A synthetic peptide

<400> SEQUENCE: 50

```
Leu Tyr Arg Ala Tyr His Val Ser Cys Gly Tyr Ser
```

```
<210> SEQ ID NO 51
<211> LENGTH: 12
<212> TYPE: PRT
<213> ORGANISM: Artificial Sequence
<220> FEATURE:
<223> OTHER INFORMATION: A synthetic peptide

<400> SEQUENCE: 51

Leu Tyr Arg Ala Gly Asp Val Ser Cys Gly Tyr Ser
1               5                   10

<210> SEQ ID NO 52
<211> LENGTH: 12
<212> TYPE: PRT
<213> ORGANISM: Artificial Sequence
<220> FEATURE:
<223> OTHER INFORMATION: A synthetic peptide

<400> SEQUENCE: 52

Leu Tyr Arg Ala Ala Asp Val Ser Cys Gly Tyr Ser
1               5                   10

<210> SEQ ID NO 53
<211> LENGTH: 12
<212> TYPE: PRT
<213> ORGANISM: Artificial Sequence
<220> FEATURE:
<223> OTHER INFORMATION: A synthetic peptide

<400> SEQUENCE: 53

Leu Tyr Arg Ala His Asp Val Ser Cys Gly Tyr Ser
1               5                   10

<210> SEQ ID NO 54
<211> LENGTH: 12
<212> TYPE: PRT
<213> ORGANISM: Artificial Sequence
<220> FEATURE:
<223> OTHER INFORMATION: A synthetic peptide

<400> SEQUENCE: 54

Leu Tyr Arg Ala Tyr Asp Val Ser Cys Gly Tyr Ser
1               5                   10

<210> SEQ ID NO 55
<211> LENGTH: 13
<212> TYPE: PRT
<213> ORGANISM: Artificial Sequence
<220> FEATURE:
<223> OTHER INFORMATION: A synthetic peptide

<400> SEQUENCE: 55

Leu Tyr Arg Ala Gly Gly Val Leu Ser Cys Gly Tyr Ser
1               5                   10

<210> SEQ ID NO 56
<211> LENGTH: 13
<212> TYPE: PRT
<213> ORGANISM: Artificial Sequence
<220> FEATURE:
<223> OTHER INFORMATION: A synthetic peptide

<400> SEQUENCE: 56

Leu Tyr Arg Ala His Gly Val Leu Ser Cys Gly Tyr Ser
1               5                   10
```

<210> SEQ ID NO 57
<211> LENGTH: 14
<212> TYPE: PRT
<213> ORGANISM: Artificial Sequence
<220> FEATURE:
<223> OTHER INFORMATION: A synthetic peptide

<400> SEQUENCE: 57

Leu Tyr Arg Ala Gly Gly Gly Val Leu Ser Cys Gly Tyr Ser
1               5                   10

<210> SEQ ID NO 58
<211> LENGTH: 15
<212> TYPE: PRT
<213> ORGANISM: Artificial Sequence
<220> FEATURE:
<223> OTHER INFORMATION: A synthetic peptide

<400> SEQUENCE: 58

Leu Tyr Arg Ala Gly Gly Gly Gly Val Leu Ser Cys Gly Tyr Ser
1               5                   10                  15

<210> SEQ ID NO 59
<211> LENGTH: 4
<212> TYPE: PRT
<213> ORGANISM: Artificial Sequence
<220> FEATURE:
<223> OTHER INFORMATION: A synthetic peptide

<400> SEQUENCE: 59

Pro Gly Tyr Ser
1

<210> SEQ ID NO 60
<211> LENGTH: 11
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (2)..(6)
<223> OTHER INFORMATION: Xaa can be any naturally occurring amino acid

<400> SEQUENCE: 60

Gly Xaa Xaa Xaa Xaa Xaa Ser Pro Gly Tyr Ser
1               5                   10

<210> SEQ ID NO 61
<211> LENGTH: 4
<212> TYPE: PRT
<213> ORGANISM: Artificial Sequence
<220> FEATURE:
<223> OTHER INFORMATION: A synthetic peptide

<400> SEQUENCE: 61

Ser Arg Val Leu
1

<210> SEQ ID NO 62
<211> LENGTH: 5
<212> TYPE: PRT
<213> ORGANISM: Artificial Sequence
<220> FEATURE:
<223> OTHER INFORMATION: A synthetic peptide

<400> SEQUENCE: 62

```
Ala Ser Arg Val Leu
1               5

<210> SEQ ID NO 63
<211> LENGTH: 5
<212> TYPE: PRT
<213> ORGANISM: Artificial Sequence
<220> FEATURE:
<223> OTHER INFORMATION: A synthetic peptide

<400> SEQUENCE: 63

Ala Ser Arg Val Leu
1               5

<210> SEQ ID NO 64
<211> LENGTH: 5
<212> TYPE: PRT
<213> ORGANISM: Artificial Sequence
<220> FEATURE:
<223> OTHER INFORMATION: A synthetic peptide

<400> SEQUENCE: 64

Leu Tyr Arg Ala Gly
1               5

<210> SEQ ID NO 65
<211> LENGTH: 11
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (1)..(6)
<223> OTHER INFORMATION: Xaa can be any naturally occurring amino acid

<400> SEQUENCE: 65

Xaa Xaa Xaa Xaa Xaa Xaa Ser Pro Gly Tyr Ser
1               5                   10

<210> SEQ ID NO 66
<211> LENGTH: 16
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (6)..(11)
<223> OTHER INFORMATION: Xaa can be any naturally occurring amino acid

<400> SEQUENCE: 66

Leu Tyr Arg Ala Gly Xaa Xaa Xaa Xaa Xaa Xaa Ser Pro Gly Tyr Ser
1               5                   10                  15

<210> SEQ ID NO 67
<211> LENGTH: 4
<212> TYPE: PRT
<213> ORGANISM: Artificial Sequence
<220> FEATURE:
<223> OTHER INFORMATION: A synthetic peptide

<400> SEQUENCE: 67

Gly Arg Val Leu
1

<210> SEQ ID NO 68
```

```
<211> LENGTH: 5
<212> TYPE: PRT
<213> ORGANISM: Artificial Sequence
<220> FEATURE:
<223> OTHER INFORMATION: A synthetic peptide

<400> SEQUENCE: 68

Gly Ser Arg Val Leu
1               5

<210> SEQ ID NO 69
<211> LENGTH: 6
<212> TYPE: PRT
<213> ORGANISM: Artificial Sequence
<220> FEATURE:
<223> OTHER INFORMATION: A synthetic peptide

<400> SEQUENCE: 69

Gly Ala Ser Arg Val Leu
1               5

<210> SEQ ID NO 70
<211> LENGTH: 5
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 70

Leu Tyr Arg Ala Xaa
1               5

<210> SEQ ID NO 71
<211> LENGTH: 7
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 71

Xaa Val Ser Pro Gly Tyr Ser
1               5

<210> SEQ ID NO 72
<211> LENGTH: 12
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 72

Leu Tyr Arg Ala Xaa Xaa Val Ser Pro Gly Tyr Ser
1               5                   10

<210> SEQ ID NO 73
<211> LENGTH: 8
<212> TYPE: PRT
```

```
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 73

Xaa Val Leu Ser Pro Gly Tyr Ser
1               5

<210> SEQ ID NO 74
<211> LENGTH: 13
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 74

Leu Tyr Arg Ala Xaa Xaa Val Leu Ser Pro Gly Tyr Ser
1               5                   10

<210> SEQ ID NO 75
<211> LENGTH: 11
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (1)..(4)
<223> OTHER INFORMATION: Xaa can be any naturally occurring amino acid

<400> SEQUENCE: 75

Xaa Xaa Xaa Xaa Val Leu Ser Pro Gly Tyr Ser
1               5                   10

<210> SEQ ID NO 76
<211> LENGTH: 16
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (5)..(9)
<223> OTHER INFORMATION: Xaa can be any naturally occurring amino acid

<400> SEQUENCE: 76

Leu Tyr Arg Ala Xaa Xaa Xaa Xaa Xaa Val Leu Ser Pro Gly Tyr Ser
1               5                   10                  15

<210> SEQ ID NO 77
<211> LENGTH: 4
<212> TYPE: PRT
<213> ORGANISM: Artificial Sequence
<220> FEATURE:
<223> OTHER INFORMATION: A synthetic peptide

<400> SEQUENCE: 77

Gly Ala Ser Arg
1

<210> SEQ ID NO 78
```

```
<211> LENGTH: 6
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 78

Xaa Asn Pro Gly Tyr Ser
1               5

<210> SEQ ID NO 79
<211> LENGTH: 8
<212> TYPE: PRT
<213> ORGANISM: Artificial Sequence
<220> FEATURE:
<223> OTHER INFORMATION: A synthetic peptide

<400> SEQUENCE: 79

Leu Tyr Arg Ala Gly Gly Ser Phe
1               5

<210> SEQ ID NO 80
<211> LENGTH: 8
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 80

Leu Tyr Arg Ala Xaa Gly Ser Phe
1               5

<210> SEQ ID NO 81
<211> LENGTH: 5
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 81

Leu Tyr Arg Ala Xaa
1               5

<210> SEQ ID NO 82
<211> LENGTH: 6
<212> TYPE: PRT
<213> ORGANISM: Artificial Sequence
<220> FEATURE:
<223> OTHER INFORMATION: A synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 82
```

```
Xaa Ser Xaa Gly Tyr Ser
1               5

<210> SEQ ID NO 83
<211> LENGTH: 5
<212> TYPE: PRT
<213> ORGANISM: Artificial Sequence
<220> FEATURE:
<223> OTHER INFORMATION: A synthetic peptide

<400> SEQUENCE: 83

Ser Pro Gly Tyr Ser
1               5
```